US011136392B2

(12) United States Patent
Brentjens et al.

(10) Patent No.: US 11,136,392 B2
(45) Date of Patent: Oct. 5, 2021

(54) PD-1 IMMUNE MODULATING AGENTS

(71) Applicants: MEMORIAL SLOAN-KETTERING CANCER CENTER, New York, NY (US); EUREKA THERAPEUTICS, INC., Emeryville, CA (US)

(72) Inventors: Renier J. Brentjens, Short Hills, NJ (US); Hollie Jaine Jackson, Hoboken, NJ (US); Cheng Liu, Emeryville, CA (US)

(73) Assignees: MEMORIAL SLOAN-KETTERING CANCER CENTER, New York, NY (US); EUREKA THERAPEUTICS, INC., Emeryville, CA (US)

(*) Notice: Subject to any disclaimer, the term of this patent is extended or adjusted under 35 U.S.C. 154(b) by 536 days.

(21) Appl. No.: 15/849,107

(22) Filed: Dec. 20, 2017

(65) Prior Publication Data
US 2018/0127502 A1 May 10, 2018

Related U.S. Application Data

(63) Continuation of application No. PCT/US2016/039015, filed on Jun. 23, 2016.

(60) Provisional application No. 62/266,398, filed on Dec. 11, 2015, provisional application No. 62/183,297, filed on Jun. 23, 2015.

(51) Int. Cl.
| | | |
|---|---|---|
| *C07K 16/28* | (2006.01) | |
| *A61K 39/395* | (2006.01) | |
| *A61K 35/17* | (2015.01) | |
| *A61K 48/00* | (2006.01) | |
| *C07K 14/705* | (2006.01) | |
| *C07K 14/725* | (2006.01) | |
| *A61K 47/68* | (2017.01) | |
| *A61P 35/00* | (2006.01) | |
| *C07K 16/30* | (2006.01) | |
| *A61K 39/00* | (2006.01) | |
| *A61K 38/00* | (2006.01) | |
| *A61K 35/12* | (2015.01) | |

(52) U.S. Cl.
CPC .......... *C07K 16/2818* (2013.01); *A61K 35/17* (2013.01); *A61K 39/39558* (2013.01); *A61K 47/6849* (2017.08); *A61K 48/00* (2013.01); *A61P 35/00* (2018.01); *C07K 14/7051* (2013.01); *C07K 14/70503* (2013.01); *C07K 16/2803* (2013.01); *C07K 16/30* (2013.01); *A61K 38/00* (2013.01); *A61K 2035/124* (2013.01); *A61K 2039/505* (2013.01); *A61K 2039/507* (2013.01); *C07K 2317/21* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/73* (2013.01); *C07K 2317/75* (2013.01); *C07K 2317/76* (2013.01); *C07K 2319/03* (2013.01); *C12N 2740/10043* (2013.01)

(58) Field of Classification Search
None
See application file for complete search history.

(56) References Cited

U.S. PATENT DOCUMENTS

| | | | | |
|---|---|---|---|---|
| 4,834,976 A | * | 5/1989 | Rosok | C07K 16/1214 424/142.1 |
| 7,488,802 B2 | | 2/2009 | Collins | |
| 8,354,509 B2 | * | 1/2013 | Carven | C07K 16/2818 530/388.1 |
| 10,913,796 B2 | * | 2/2021 | Brentjens | A61K 47/6425 |
| 2010/0150918 A1 | * | 6/2010 | Kufer | C07K 16/4291 424/133.1 |
| 2014/0219975 A1 | * | 8/2014 | June | A61P 37/04 424/93.21 |
| 2014/0242077 A1 | | 8/2014 | Choi et al. | |
| 2016/0045551 A1 | * | 2/2016 | Brentjens | C07K 14/7051 424/93.71 |
| 2017/0275362 A1 | * | 9/2017 | Brentjens | C07K 14/7056 |
| 2018/0118829 A1 | * | 5/2018 | Mabry, III | C07K 16/2818 |
| 2018/0148503 A1 | * | 5/2018 | Scheinberg | C07K 16/2833 |
| 2019/0284262 A1 | * | 9/2019 | Scheinberg | A61P 43/00 |
| 2020/0281974 A1 | * | 9/2020 | Barber | C12N 15/63 |

FOREIGN PATENT DOCUMENTS

| | | |
|---|---|---|
| CN | 101213297 A | 7/2008 |
| WO | 2014134165 | 9/2014 |

OTHER PUBLICATIONS

Fedorov et al. PD-1- and CTLA-4-based inhibitory chimeric antigen receptors (iCARs) divert off-target immunotherapy responses. Science Translational Medicine 5, 215ra172 (2013).*
Cherkassky et al., "Human CAR T cells with cell-intrinsic PD-1 checkpoint blockade resist tumor-mediated inhibition," J. Clin. Invest. 126, 3130-44, 2016.*
Chong et al., "PD-1 blockade modulates chimeric antigen receptor (CAR)-modified T cells: refueling the CAR," Blood. 129(8), 1039-41, 2017.*
John et al., "Blockade of PD-1 immunosuppression boosts CAR T-cell therapy," OncoImmunology 2, e26286, 3 pages, 2013.*
Philips G.K. & Atkins M., Therapeutic uses of anti-PD-1 and anti-PD-L1 antibodies. Int Immunol, Oct. 16, 2014, vol. 27, No. 1, pp. 39-46.

(Continued)

*Primary Examiner* — Ilia I Ouspenski
(74) *Attorney, Agent, or Firm* — Heslin Rothenberg Farley & Mesiti P.C.

(57) ABSTRACT

The present application provides anti-PD-1 antigen-binding proteins or a fragment thereof, as well as nucleic acids encoding anti-PD-1 antigen-binding proteins or CAR T cells expressing such antigen-binding protein or fragment. Also provided are methods of regulating T cells or treating patients using such constructs or cells.

36 Claims, 35 Drawing Sheets

Specification includes a Sequence Listing.

(56) References Cited

OTHER PUBLICATIONS

Mihara et al. "Synergistic and persistent effect of T-cell immunotherapy with anti-CD19 or anti-CD38 chimeric receptor in conjunction with rituximab on B-cell non-Hodgkin lymphoma," British Journal of Haematology, vol. 151, No. 1, pp. 37-46, Oct. 1, 2010.
John et al. "Anti-PD-1 antibody therapy potently enhances the eradication of established tumors by gene-modified T cells," Clinical Cancer Research, The American Association for Cancer Research, US, vol. 19, No. 20, pp. 5636-5646, Oct. 15, 2013.
International Search Report and Written Opinion of the International Searching Authority for PCT/US2016/039015, dated Sep. 28, 2016, 12 pages.
International Preliminary Report on Patentability for PCT/US2016/039015, dated Dec. 26, 2017, 8 pages.
Examination Report, dated Aug. 23, 2021, issued by Intellectual Property India in connection with IN application No. 201817001999, a National Stage Entry of PCT/US2016/039015.

\* cited by examiner

|  | LV | | | | HV | | | |
|---|---|---|---|---|---|---|---|---|
|  | CDR1 | | CDR2 | CDR3 | | CDR1 | | CDR2 | | CDR3 | |
| #16 | QSISSY | 1 | AAS | QQSYSTPLT | 2 | GFTSSSYW | 3 | IKQDGSEK | 4 | ARGGWSYDM | 5 |
| #18 | SSNIGAGYA | 12 | TNN | QSYDSLSGVI | 13 | GYTLTELS | 14 | FDPEDGET | 15 | ARAYYGFDQ | 16 |
| #23 | SSNIGNWA | 23 | YND | AAWDDSLNGYV | 24 | GYTFTRKG | 25 | ISVNNGNT | 26 | ARYMYGRRDS | 27 |
| #25 | NIGSKS | 34 | YDS | QVWDNHSDVV | 35 | RMKFSSYA | 36 | ISGSGGT | 37 | ARWYSSYYDV | 38 |
| #27 | NIGSKS | 34 | YDS | QVWDSSSDYV | 45 | GFTFSSYA | 46 | ISGSGGST | 47 | ARNYISMFDS | 48 |
| #31 | NIGSKS | 34 | YDS | QVWDSSSDHV | 55 | GFTFSSYA | 46 | ISGSGGST | 47 | ARGYSSYDA | 56 |
| #40 | RSNIGENT | 63 | SNN | AAWDDRLNGYV | 64 | GYTFTNYG | 65 | IGAQKGDT | 66 | ARSQGVPFDS | 67 |
| #36 | RSNIGSNT | 74 | NNN | ATWDDSLNEYV | 75 | GYTFTRYG | 76 | ISGYNGNT | 77 | ARHGYGYHGD | 78 |
| #37 | SSNIGAGYV | 85 | HNN | QSYDSLSGWV | 86 | GFTFKDYY | 87 | ISTSGNSV | 88 | ARSPQHSQYDS | 89 |
| #19 | NIGDKS | 96 | YDS | QVWASGTDHPYVI | 97 | GFTFSSYA | 46 | ISGSGGST | 47 | ARMYGSYTDM | 98 |
| #14 | SSNIGYNY | 105 | RNN | TSWDDSLSGYV | 106 | GNAFTNFY | 107 | INPSGTDLT | 108 | ARQYAYGYSGFDM | 109 |
| #47 | QSVSNW | 116 | AAS | QQSYSTPIT | 117 | GYTFTSYY | 118 | INPNTGGS | 119 | ARGDVTYDE | 120 |
| #46 | NIGSKS | 34 | YDD | QVWDINDHYV | 127 | GFTFSSYA | 46 | ISGSGGST | 47 | ARSQASFMDI | 128 |
| #42 | NIGSKS | 34 | DDS | QVWDSSSDQGV | 135 | GFTFSSYA | 46 | IGTGGGT | 136 | ARGTGVGDGQ | 137 |

FIGURE 9

PD-1 IMMUNE MODULATING AGENTS

CROSS REFERENCE TO RELATED APPLICATIONS

This application is a continuation of PCT/US2016/039015 filed Jun. 23, 2016 and published on Dec. 29, 2016 as WO 2016/210129, which claims priority to U.S. Provisional Application No. 62/183,297 filed Jun. 23, 2015 and U.S. Provisional Application No. 62/266,398 filed Dec. 11, 2015; the entire contents of each are hereby incorporated by reference in their entirety into the present disclosure.

SEQUENCE LISTING

This application contains a Sequence Listing, created on Jun. 16, 2016; the file, in ASCII format, is designated 3314070AWO_SequenceListing_ST25.txt and is 104 kilobytes in size. The file is hereby incorporated by reference in its entirety into the present application.

TECHNICAL FIELD

The present disclosure relates generally to antigen-binding proteins involved in immune function. More particularly, the present disclosure relates to recombinant antibodies, chimeric antigen receptors and fragments thereof with specificity for PD-1.

BACKGROUND OF THE DISCLOSURE

The goal of cancer immunotherapy is to treat malignant disease by modulating cancer specific immune responses. A prime target is the programmed cell death (PD-1) receptor, which is expressed on the surface of activated T cells and leads to an intracellular inhibitory signal when bound to one of its ligands, PD-L1 and PD-L2.

PD-1 has been shown to play a role in cancer. In humans, expression of PD-1 and/or PD-L1 has been found in a number of primary tumor biopsies assessed by immunohistochemistry. Such tissues include cancers of the lung, liver, ovary, cervix, skin, colon, glioma, bladder, breast, kidney, esophagus, stomach, oral squamous cell, urothelial cell, and pancreas as well as tumors of the head and neck. Furthermore, PD-ligand expression on tumor cells has been correlated to poor prognosis of cancer patients across multiple tumor types.

There is an ongoing need for new therapeutics, including antibodies and other antigen-binding proteins that target PD-1 and function either as agonists of PD-1 or antagonists thereof.

SUMMARY OF THE DISCLOSURE

The present disclosure describes antigen-binding proteins such as antibodies and chimeric antigen receptors that are able to specifically bind a protein receptor associated with programmed cell death, PD-1, on T cells, thereby modulating immune response by the T cells. By inhibiting the binding of PD-1 to its ligand, PD-L1, blockade of the PD-1 signaling pathway inhibits apoptosis of the T cells.

In one aspect, therefore, the disclosure relates to recombinant antigen-binding proteins, antibodies and chimeric antigen receptors or antigen-binding portions thereof that bind specifically to PD-1 and prevent binding of its ligand.

In one aspect, therefore, the disclosure relates to a recombinant antigen-binding protein or antigen-binding fragment thereof comprising one of:

(A) an antigen binding region having an amino acid sequence selected from the group consisting of SEQ ID NO: 10, SEQ ID NO: 21, SEQ ID NO: 32, SEQ ID NO: 43, SEQ ID NO: 53, SEQ ID NO: 61, SEQ ID NO: 72, SEQ ID NO: 83, SEQ ID NO: 94, SEQ ID NO: 103, SEQ ID NO: 114, SEQ ID NO: 125, SEQ ID NO: 133, SEQ ID NO: 142; a fragment thereof, and a homologous sequence thereof;

(B) an antigen binding region comprising a variable light chain (VL) and variable heavy chain (VH), respectively, with amino acid sequences selected from SEQ ID NOS: 6 and 8; SEQ ID NOS: 17 and 19; SEQ ID NOS: 28 and 30; SEQ ID NOS: 39 and 41; SEQ ID NOS: 49 and 51; SEQ ID NOS: 57 and 59; SEQ ID NOS: 68 and 70; SEQ ID NOS: 79 and 81; SEQ ID NOS: 90 and 92; SEQ ID NOS: 99 and 101; SEQ ID NOS: 110 and 112; SEQ ID NOS: 121 and 123; SEQ ID NOS: 129 and 131; SEQ ID NOS: 138 and 140; fragments thereof, and homologous sequences thereof; or (C) an antigen binding region comprising:

(i) a light chain (LC) comprising light chain complementarity determining regions (LCCDR) LCCDR1, LCCDR2 and LCCDR3 respectively, having the amino acid sequence QSISSY (SEQ ID NO: 1), AAS and QQSYSTPLT (SEQ ID NO: 2) and a heavy chain (HC) comprising heavy chain complementarity determining regions (HCCDR) HCCDR1, HCCDR2 and HCCDR3 respectively, having amino acid sequences GFTSSSYW (SEQ ID NO: 4), IKQDGSEK (SEQ ID NO. 5) and ARGGWSYDM (SEQ ID NO: 6); fragments thereof or homologous sequences thereof;

(ii) a light chain (LC) comprising LCCDR1, LCCDR2 and LCCDR3 respectively, having the amino acid sequence SSNIGAGYA (SEQ ID NO: 12), TNN and QSYDSSLSGVI (SEQ ID NO: 13) and a heavy chain (HC) comprising HCCDR1, HCCDR2 and HCCDR3 respectively, having amino acid sequences GYTLTELS (SEQ ID NO: 14), FDPEDGET (SEQ ID NO. 15) and ARAYYGFDQ (SEQ ID NO: 16); fragments thereof or homologous sequences thereof;

(iii) a light chain (LC) comprising LCCDR1, LCCDR2 and LCCDR3 respectively, having the amino acid sequence SSNIGNNA (SEQ ID NO: 23), YND and AAWDDSVNGYV (SEQ ID NO: 24) and a heavy chain (HC) comprising HCCDR1, HCCDR2 and HCCDR3 respectively, having amino acid sequences GYTFTRFG (SEQ ID NO: 25), ISVNNGNT (SEQ ID NO. 26) and ARYMYGRRDS (SEQ ID NO: 27); fragments thereof or homologous sequences thereof;

(iv) a light chain (LC) comprising LCCDR1, LCCDR2 and LCCDR3 respectively, having the amino acid sequence NIGSKS (SEQ ID NO: 34), YDS and QVWDNHSDW (SEQ ID NO: 35) and a heavy chain (HC) comprising HCCDR1, HCCDR2 and HCCDR3 respectively, having amino acid sequences RNKFSSYA (SEQ ID NO: 36), ISGSGGTT (SEQ ID NO. 37) and ARWYSSYYDV (SEQ ID NO: 38); fragments thereof or homologous sequences thereof;

(v) a light chain (LC) comprising LCCDR1, LCCDR2 and LCCDR3 respectively, having the amino acid sequence NIGSKS (SEQ ID NO: 34), YDS and QVWDSSSDYV (SEQ ID NO: 45) and a heavy chain (HC) comprising HCCDR1, HCCDR2 and HCCDR3 respectively, having amino acid sequences GFTFSSYA (SEQ ID NO: 46), ISGSGGST (SEQ ID NO. 47) and ARNYISMFDS (SEQ ID NO: 48); fragments thereof or homologous sequences thereof;

(vi) a light chain (LC) comprising LCCDR1, LCCDR2 and LCCDR3 respectively, having the amino acid sequence NIGSKS (SEQ ID NO: 34), YDS and QVWDSSSDHV (SEQ ID NO: 55) and a heavy chain (HC) comprising HCCDR1, HCCDR2 and HCCDR3 respectively, having amino acid sequences GFTFSSYA (SEQ ID NO: 46), ISGSGGST (SEQ ID NO. 47) and ARGYSSYYDA (SEQ ID NO: 56); fragments thereof or homologous sequences thereof;

(vii) a light chain (LC) comprising LCCDR1, LCCDR2 and LCCDR3 respectively, having the amino acid sequence RSNIGENT (SEQ ID NO: 63), SNN and AAWDDRLNGYV (SEQ ID NO: 64) and a heavy chain (HC) comprising HCCDR1, HCCDR2 and HCCDR3 respectively, having amino acid sequences GYTFTNYG (SEQ ID NO: 65), IGAQKGDT (SEQ ID NO. 66) and ARSQGVPFDS (SEQ ID NO: 67); fragments thereof or homologous sequences thereof;

(viii) a light chain (LC) comprising LCCDR1, LCCDR2 and LCCDR3 respectively, having the amino acid sequence RSNIGSNT (SEQ ID NO: 74), NNN and ATWDDSLNEYV (SEQ ID NO: 75) and a heavy chain (HC) comprising HCCDR1, HCCDR2 and HCCDR3 respectively, having amino acid sequences GYTFTRYG (SEQ ID NO: 76), ISGYNGNT (SEQ ID NO. 77) and ARHGYGYHGD (SEQ ID NO: 78); fragments thereof or homologous sequences thereof;

(ix) a light chain (LC) comprising LCCDR1, LCCDR2 and LCCDR3 respectively, having the amino acid sequence SSNIGAGYV (SEQ ID NO: 85), HNN and QSYDSSLSGWV (SEQ ID NO: 86) and a heavy chain (HC) comprising HCCDR1, HCCDR2 and HCCDR3 respectively, having amino acid sequences GFTFKDYY (SEQ ID NO: 87), ISTSGNSV (SEQ ID NO. 88) and ARSPGHSDYDS (SEQ ID NO: 89); fragments thereof or homologous sequences thereof;

(x) a light chain (LC) comprising LCCDR1, LCCDR2 and LCCDR3 respectively, having the amino acid sequence NIGDKS (SEQ ID NO: 96), YDS and QVWASGTDHPYVI (SEQ ID NO: 97) and a heavy chain (HC) comprising HCCDR1, HCCDR2 and HCCDR3 respectively, having amino acid sequences GFTFSSYA (SEQ ID NO: 46), ISGSGGST (SEQ ID NO. 47) and ARMYGSYTDM (SEQ ID NO: 98); and a fragment or homologous sequence thereof;

(xi) a light chain (LC) comprising LCCDR1, LCCDR2 and LCCDR3 respectively, having the amino acid sequence SSNIGYNY (SEQ ID NO: 105), RNN and TSWDDSLSGYV (SEQ ID NO: 106) and a heavy chain (HC) comprising HCCDR1, HCCDR2 and HCCDR3 respectively, having amino acid sequences GNAFTNFY (SEQ ID NO: 107), INPSGTDLT (SEQ ID NO. 108) and ARQYAYGYSGFDM (SEQ ID NO: 109); fragments thereof or homologous sequences thereof;

(xii) a light chain (LC) comprising LCCDR1, LCCDR2 and LCCDR3 respectively, having the amino acid sequence QSVSNW (SEQ ID NO: 116), AAS and QQSYSTPIT (SEQ ID NO: 117) and a heavy chain (HC) comprising HCCDR1, HCCDR2 and HCCDR3 respectively, having amino acid sequences GYTFTSYY (SEQ ID NO: 118), INPNTGGS (SEQ ID NO. 119) and ARGDVTYDE (SEQ ID NO: 120); fragments thereof or homologous sequences thereof;

(xiii) a light chain (LC) comprising LCCDR1, LCCDR2 and LCCDR3 respectively, having the amino acid sequence NIGSKS (SEQ ID NO: 34), YDD and QVWDINDHYV (SEQ ID NO: 127) and a heavy chain (HC) comprising HCCDR1, HCCDR2 and HCCDR3 respectively, having amino acid sequences GFTFSSYA (SEQ ID NO: 46), ISGSGGST (SEQ ID NO. 47) and ARSQASFMDI (SEQ ID NO: 128); fragments thereof or homologous sequences thereof; or (xiv) a light chain (LC) comprising LCCDR1, LCCDR2 and LCCDR3 respectively, having the amino acid sequence NIGSKS (SEQ ID NO: 34), DDS and QVWDSSSDQGV (SEQ ID NO: 135) and a heavy chain (HC) comprising HCCDR1, HCCDR2 and HCCDR3 respectively, having amino acid sequences GFTFSSYA (SEQ ID NO: 46), IGTGGGT (SEQ ID NO. 136) and ARGTGYDGDQ (SEQ ID NO: 137) and fragments thereof or homologous sequences thereof.

In some embodiments, the recombinant antigen-binding protein or antigen-binding fragment thereof comprises a fragment of at least one of the recited SEQ ID NOS that is at least 40%, 45%, 50%, 55%, 60%, 65%, 70%, 75%, 80%, 85%, 90%, 91%, 92%, 93%, 94%, 95%, 96%, 97%, 98%, or 99% of the entire length of the at least one recited SEQ ID NO. In some embodiments, the recombinant antigen-binding protein or antigen-binding fragment thereof comprises a sequence homologous to at least one of the recited SEQ ID NOS that has at least 60%, 65%, 70%, 75%, 80%, 85%, 90%, 91%, 92%, 93%, 94%, 95%, 96%, 97%, 98%, 99%, 99.5%, or 99.9% identity to the at least one recited SEQ ID NO.

In a related aspect, the disclosure relates to recombinant antigen-binding proteins or antigen-binding fragments thereof, wherein the recombinant antigen-binding protein is an antibody, chimeric antigen receptor (CAR), fusion protein or conjugate thereof. In an embodiment, the recombinant antigen-binding protein or antigen-binding fragment thereof is conjugated to a therapeutic agent, for example, a drug, toxin or cytotoxic moiety, radioisotope, protein or peptide.

An antibody of the disclosure is a full-length antibody, an intact antibody, fragments and homologous sequences thereof, including but not limited to, an Fab fragment, an F(ab')$_2$ fragment or a single chain variable fragment (scFv).

In the recombinant antigen-binding protein, the antigen-binding region specifically binds to an epitope of human PD-1 and blocks binding of PD-1 to its ligand(s).

In a related aspect, the disclosure relates to nucleic acids encoding an antigen-binding protein of the disclosure as well as vectors and cells comprising such nucleic acids or antigen-binding proteins.

In yet another aspect, the disclosure relates to a method of increasing a T cell response in a subject comprising administering a therapeutically effective amount of an antigen-binding protein or an antigen binding fragment thereof. The administration of a therapeutically effective amount of the antigen-binding protein or antigen binding fragment thereof inhibits, reduces, modulates or abolishes signal transduction mediated by PD-1.

In yet another related aspect, the disclosure relates to a method for treatment of a subject having a PD1-positive disease comprising administering to the subject a therapeutically effective amount of an antigen-binding protein or antigen binding fragment thereof. In an embodiment, a pharmaceutical composition comprising the antigen-binding protein or antigen binding fragment thereof is administered.

In another aspect of the invention, the disclosure relates to a vector comprising a nucleic acid encoding a recombinant anti-PD-1 antigen-binding protein and a nucleic acid encoding a chimeric antigen receptor, wherein said recombinant anti-PD-1 antigen-binding protein is not identical to said chimeric antigen receptor.

In yet another aspect, the disclosure relates to a cell comprising the vector described herein. In a related aspect, the disclosure relates to a cell comprising a nucleic acid encoding a recombinant anti-PD-1 antigen-binding protein and a nucleic acid encoding a chimeric antigen receptor, wherein said recombinant anti-PD-1 antigen-binding protein is not identical to said chimeric antigen receptor. In another related aspect, the disclosure relates to a cell comprising a recombinant anti-PD-1 antigen-binding protein and a chimeric antigen receptor, wherein said recombinant anti-PD-1 antigen-binding protein is not identical to said chimeric antigen receptor.

In some embodiments of the vectors or the cells described herein, the chimeric antigen receptor does not specifically bind to PD-1.

In another aspect of the invention, the disclosure provides a method of increasing a T cell response in a subject comprising administering to the subject a therapeutically effective amount of a recombinant anti-PD-1 antigen-binding protein, a vector, a cell, or a pharmaceutical composition described herein, wherein the recombinant anti-PD-1 antigen-binding protein is a PD-1 antagonist.

In yet another aspect of the invention, the disclosure provides a method of decreasing a T cell response in a subject comprising administering to the subject a therapeutically effective amount of a recombinant anti-PD-1 antigen-binding protein, a vector, a cell, or a pharmaceutical composition described herein, wherein the recombinant anti-PD-1 antigen-binding protein is a PD-1 agonist.

In another aspect of the invention, the disclosure provides a method for treatment of a subject having a PD1-positive disease, comprising administering to the subject a therapeutically effective amount of a recombinant anti-PD-1 antigen-binding protein, a vector, a cell, or a pharmaceutical composition described herein.

In a related aspect, the disclosure provides a method for treatment of a subject having a PD1-positive disease, comprising transducing at least one T cell of the subject with a nucleic acid encoding a recombinant anti-PD-1 antigen-binding protein and a nucleic acid encoding a chimeric antigen receptor, wherein said recombinant anti-PD-1 antigen-binding protein is not identical to said chimeric antigen receptor.

In some embodiments of the methods described herein, the chimeric antigen receptor does not specifically bind to PD-1. In some embodiments, the PD1-positive disease is a cancer. In some embodiments, the PD1-positive disease is an autoimmune disease.

BRIEF DESCRIPTION OF THE DRAWINGS

FIG. 9 shows the amino acid sequences for the complementarity determining regions (CDR) for light and heavy variable chains of some antigen-binding proteins of the disclosure.

DETAILED DESCRIPTION OF THE DISCLOSURE

Figure 1:
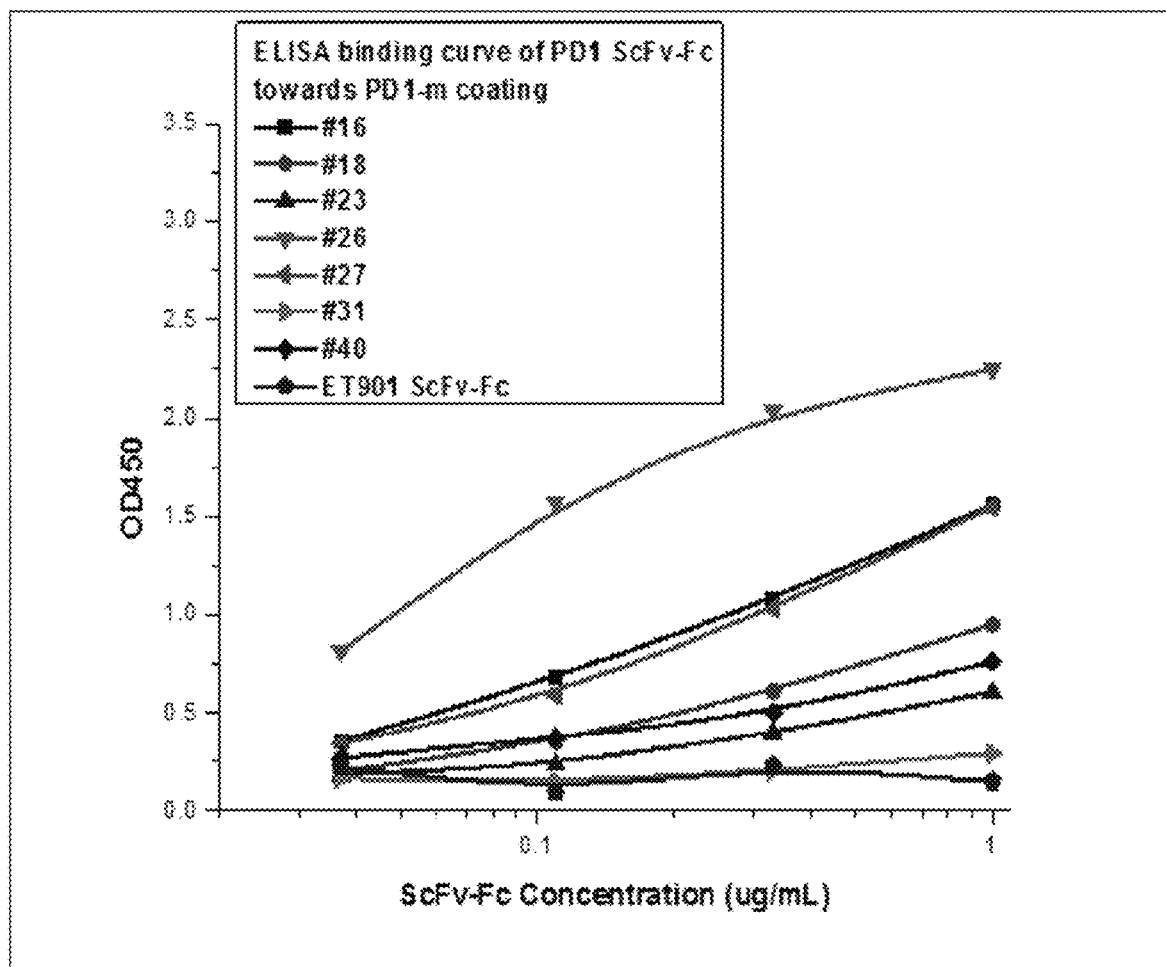
FIG. 1 shows relative binding affinity of scFv-Fc clones to PD-1 monomer. The ability of scFv-Fc clones to bind PD-1 was determined by detecting level of binding to PD-1 monomer. Binding affinity of the scFv-Fc clones was ranked where clone 31 bound weakly and clones 26 and 27 bound the most (31<23<40<18<16=27<26.)

All publications, patents and other references cited herein are incorporated by reference in their entirety into the present disclosure.

In practicing the present disclosure, many conventional techniques in molecular biology, microbiology, cell biology, biochemistry, and immunology are used, which are within the skill of the art. These techniques are described in greater detail in, for example, Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure.

In the description that follows, certain conventions will be followed as regards the usage of terminology. Generally, terms used herein are intended to be interpreted consistently with the meaning of those terms as they are known to those of skill in the art.

An "antigen-binding protein" is a protein or polypeptide that comprises an antigen-binding region or antigen-binding portion, that is, has a strong affinity to another molecule to which it binds. Antigen-binding proteins encompass antibodies, chimeric antigen receptors and fusion proteins.

"Antibody" and "antibodies" as those terms are known in the art refer to antigen binding proteins of the immune system. The term "antibody" as referred to herein includes whole, full length antibodies and any fragment thereof in which the "antigen-binding portion" or "antigen-binding region" is retained, or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant (CH) region. The heavy chain constant region is comprised of three domains, CH1, CH2 and CH3. Each light chain is comprised of a light chain variable region (abbreviated herein as VL) and a light chain constant CL region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" or "antigen-binding region" of an antibody, as used herein, refers to that region or portion of the antibody that confers antigen specificity; fragments of antigen-binding proteins, for example, antibodies therefore, includes one or more fragments of an antibody that retain the ability to specifically bind to an antigen (e.g., an HLA-peptide complex). It has been shown that the antigen-binding function of an antibody can be performed by fragments of a full-length antibody. Examples of antigen-binding fragments encompassed within the term "antibody fragments" of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a Fab fragment (Ward et al., 1989 Nature 341:544-546), which consists of a VH domain; and an isolated complementarity determining region (CDR).

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules. These are known as single chain Fv (scFv); see e.g., Bird et al., 1988 Science 242:423-426; and Huston et al., 1988 Proc. Natl. Acad. Sci. 85:5879-5883. Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

A "recombinant antibody" or "recombinant antigen-binding protein" is one which has an antigen binding portion that has been identified and selected based on binding characteristics for inclusion in a recombinantly generated antigen-binding protein, for example an antibody.

The term "homologous sequence thereof" refers to amino acid and nucleotide sequences that are between 60 and 99.9% identical to the sequences shown in Tables 1-14. In some embodiments, a homologous sequence has at least 60%, 65%, 70%, 75%, 80%, 85%, 90%, 91%, 92%, 93%, 94%, 95%, 96%, 97%, 98%, 99%, 99.5%, or 99.9% identity. In an embodiment, a homologous sequence has 95-99.9% identity; in another embodiment the homologous sequence has 98-99.9%.

In one embodiment, single chain variable fragments (scFv) that specifically bind to human PD-1 were selected and tested. scFvs were isolated from a phage display library that is a proprietary fully human antibody scFv phage library (Eureka Therapeutics, Emeryville Calif.). The library is composed of human antibody repertoires from more than 100 Caucasian and Asian healthy donors, and from donors with autoimmune disease, such as systemic lupus erythematosus, scleroderma, etc.

The antigen used for antibody phage panning was a recombinant fusion protein, PD-1 extracellular domain fused to human IgG1 Fc (PD-1 ECD-Fc domain. DNA sequences encoding PD-1 ECD and hIgG1 Fc were synthesized by Genewiz, Inc. (South Plainfield, N.J.). The DNA sequences were then subcloned into Eureka's proprietary mammalian expression vector, which was then transfected into HEK293 cells for fusion protein expression. PD-1 ECD-Fc fusion protein was purified by standard FPLC method from HEK293 cell culture medium after the cells died off.

A human scFv antibody phage display library is used for the selection of mAb clones. In brief, biotinylated antigens (PD-1 ECD-Fc fusion protein) can be first mixed with the human scFv phage library, then the antigen-scFv antibody complexes can be pulled down by streptavidin-conjugated Dynabeads M-280 through a magnetic rack. Bound clones can then be eluted and used to infect *E. Coli* XL1-Blue. The scFv phage clones expressed in the bacteria can be purified (Yasmina N A, et al. *Probing the binding mechanism and affinity of tanezumab, a recombinant humanized anti-NGF monoclonal antibody, using a repertoire of biosensors*. Protein Science 2008; 17(8): 1326-1335; Roberts W K, et al. *Vaccination with CD20 peptides induces a biologically active, specific immune response in mice*. Blood 2002: 99 (10): 3748-3755). Panning can be performed for 3-4 cycles to enrich scFv phage clones that bind to PD-1 specifically. Positive clones can be determined by standard ELISA method against biotinylated single chain PD-1. Positive clones can be further tested for their binding to PD-1 on live cell surfaces by flow cytometry, using a PD-1$^+$ cell line, for example a 3T3 cell line.

Some clones encompassed by the disclosure are referred to herein as clones 14, 16, 18, 19, 23, 26, 27, 31, 36, 37, 40, 42, 46, and 47. Variable light (VL) and variable heavy (VH) chain amino acid sequences and the nucleotide sequences that code for these embodiments are shown in Tables 1-14 below. In some embodiments, the VL and VH sequences were linked with a serine glycine linker to form an scFv. In some embodiments, a HA/His tag can be included to allow for detection of the scFv.

In some embodiments, the disclosure includes anti-bodies that have the scFv sequence fused to one or more constant domains of the heavy chain to form an antibody with an Fc region of a human immunoglobulin to yield a bivalent protein, increasing the overall avididty and stability of the antibody. In addition, the Fc portion allows the direct conjugation of other molecules, including but not limited to fluorescent dyes, cytotoxins, radioisotopes etc. to the antibody for example, for use in antigen quantitation studies, to immobilize the antibody for affinity measurements, for targeted delivery of a therapeutic agent, to test for Fc-mediated cytotoxicity using immune effector cells and many other applications.

In some embodiments, the anti-PD-1 antigen-binding proteins may comprise one or more framework region amino acid substitutions designed to improve protein stability, antibody binding, expression levels or to introduce a site for conjugation of therapeutic agents. These scFv are then used to produce recombinant human monoclonal Igs in accordance with methods known to those of skill in the art.

In some embodiments, the antigen-binding protein is a chimeric antigen receptor (CAR). Chimeric antigen receptor therapy (CAR-T therapy) is a new form of targeted immunotherapy. It merges the exquisite targeting specificity of monoclonal antibodies with the potent cytotoxicity and long-term persistence provided by cytotoxic T cells. This technology enables T cells to acquire long-term novel antigenic specificity independent of the endogenous TCR. Clinical trials have shown clinically significant antitumor activity of CAR-T therapy in neuroblastoma (Louis C. U. et al., *Blood* 118(23):6050-6056), B-ALL (Maude S. L. et al., *N. Engl. J. Med.* 371(16):1507-1517, 2014), CLL (Brentjens R. J. et al., *Blood* 118(18):4817-4828, 2011), and B cell lymphoma (Kochenderfer J. N. et al., *Blood.* 116(20):4099-4102, 2010). In one study, a 90% complete remission rate in 30 patients with B-ALL treated with CD19-CAR T therapy was reported (Maude S. L. et al., supra).

In some embodiments, the chimeric antigen receptor comprises an extracellular domain comprising the antibody moiety, a transmembrane domain, and an intracellular signaling domain. In some embodiments, the intracellular signaling domain comprises a CD3ζ intracellular signaling sequence and a co-stimulatory signaling sequence. In some embodiments, the co-stimulatory signaling sequence is a CD28 intracellular signaling sequence.

Other aspects of the disclosure include without limitation, the use of antigen-binding proteins and nucleic acids that encode them for treatment of PD1 associated disease, for diagnostic and prognostic applications as well use as research tools for the detection of PD1 in cells and tissues. Pharmaceutical compositions comprising the disclosed antigen-binding proteins and nucleic acids are encompassed by the disclosure. Vectors comprising the nucleic acids of the disclosure for antibody-based treatment by vectored immunotherapy are also contemplated by the present disclosure. Vectors include expression vectors which enable the expression and secretion of antibodies, as well as vectors which are directed to cell surface expression of the antigen binding proteins, such as chimeric antigen receptors (CAR).

Cells comprising the nucleic acids, for example cells that have been transfected with the vectors of the disclosure are also encompassed by the disclosure.

For use in diagnostic and research applications, kits are also provided that contain a PD1 antibody or nucleic acids of the disclosure, assay reagents, buffers, and the like.

TABLE 1

| | PD1-16 | | |
|---|---|---|---|
| Antigen | PD1 ECD-hIgG1 Fc fusion | | |
| CDRs: | 1 | 2 | 3 |
| VL | QSISSY (SEQ ID NO: 1) | AAS | QQSYSTPLT (SEQ ID NO: 2) |
| VH | GFTSSSYW (SEQ ID NO: 3) | IKQDGSEK (SEQ ID NO: 4) | ARGGWSYDM (SEQ ID NO: 5) |
| Full VL | DIQMTQSPSSLSASVGDRVTITCRASQSISSYLNWYQQKPGKAPKLLIYAASSLQS GVPSRFSGSGSGTDFTLTISSLQPEDFATYYCQQSYSTPLTFGGGTKVEIKRSR (SEQ ID NO: 6) | | |
| DNA | gacatccagatgacccagtctccatcctccctgtctgcatctgtaggagacagagtcaccatcacttgccgggcaag tcagagcattagcagctatttaaattggtatcagcagaaaccagggaaagcccctaagctcctgatctatgctgcatc cagtttgcaaagtggggtcccatcaaggttcagtggcagtggatctgggacagatttcactctcaccatcagcagtct gcaacctgaagattttgcaacttactactgtcaacagagttacagtacccccgctcactttcggcggagggaccaagg tggagatcaaacgt (SEQ ID NO: 7) | | |
| Full VH | EVQLVESGGGLVQPGGSLRLSCAASGFTSSSYWMSWWVRQAPGRGLEWVANIKQ DGSEKYYVDSVKGRFTISRDNAKNSLYLQMNSLRAEDTAVYYCARGGWSYDMW GQGTLVTVSS (SEQ ID NO: 8) | | |
| DNA | gaggtgcagctggtggagtctgggggaggcttggtccagcctgggggtccctgagactctcctgtgcagcctctgg attcacctctagtagctattggatgagctgggtccgccaggctccagggagagggctggagtgggtggccaacata aagcaagatggaagtgagaagtactatgtggactctgtgaagggccgattcaccatctccagagacaacgccaa gaactcactgtatctgcaaatgaacagcctgagagccgaggacactgccgtgtattactgtgcgcgcggtggttggt cttacgatatgtggggtcaaggtactctggtgaccgtctcctca (SEQ ID NO: 9) | | |
| scFv PD1-16 | DIQMTQSPSSLSASVGDRVTITCRASQSISSYLNWYQQKPGKAPKLLIYAASSLQS GVPSRFSGSGSGTDFTLTISSLQPEDFATYYCQQSYSTPLTFGGGTKVEIKRSRG GGGSGGGGSGGGGSEVQLVESGGGLVQPGGSLRLSCAASGFTSSSYWMSWVR QAPGRGLEWVANIKQDGSEKYYVDSVKGRFTISRDNAKNSLYLQMNSLRAEDTA VYYCARGGWSYDMWGQGTLVTVSS HHHHHHGAYPYDVPDYAS* | | |

TABLE 1-continued

PD1-16

(SEQ ID NO: 10)

DNA (5'-3')
gacatccagatgacccagtctccatcctccctgtctgcatctgtaggagacagagtcaccatcacttgccgggcaag
tcagagcattagcagctatttaaattggtatcagcagaaaccagggaaagcccctaagctcctgatctatgctgcatc
cagtttgcaaagtggggtcccatcaaggttcagtggcagtggatctgggacagatttcactctcaccatcagcagtct
gcaacctgaagattttgcaacttactactgtcaacagagttacagtaccccgctcactttcggcggagggaccaagg
tggagatcaaacgtggtggtggtggtagcggcggcggcggctctggtggtggtggatccgaggtgcagctggtgga
gtctggggaggcttggtccagcctgggggggtccctgagactctcctgtgcagcctctggattcacctctagtagctatt
ggatgagctgggtccgccaggctccaggagagggctggagtgggtggccaacataaagcaagatggaagtga
gaagtactatgtggactctgtgaagggccgattcaccatctccagagacaacgccaagaactcactgtatctgcaa
atgaacagcctgagagccgaggacactgccgtgtattactgtgcgcgcggtggttggtcttacgatatgggggtca
aggtactctggtgaccgtctcctca
(SEQ ID NO: 11)

TABLE 2

PD1-18

| Antigen | PD1 ECD-hIgG1 Fc fusion | | |
|---|---|---|---|
| CDRs: | 1 | 2 | 3 |
| VL | SSNIGAGYA<br>(SEQ ID NO: 12) | TNN | QSYDSSLSGVI<br>SEQ ID NO: 13) |
| VH | GYTLTELS<br>(SEQ ID NO: 14) | FDPEDGET<br>(SEQ ID NO: 15) | ARAYYGFDQ<br>(SEQ ID NO: 16) |

Full VL
QSVLTQPPSVSGAPGQRVTISCTGSSSNIGAGYAVNWYQLLPGTAPKLLISTNNNR
PSGVPDRFSGSQFGASASLAITGLQAEDEADYYCQSYDSSLSGVIFGGGTKLTVLG
(SEQ ID NO: 17)

DNA
cagtctgtgttgacgcagccgccctcagtgtctggggcccagggcagagggtcaccatctcctgcactgggagcag
ctccaacatcggggcaggttatgctgtaaattggtaccagcttcttccaggaacagccccaaactcctcatctctacta
acaacaatcggccctcaggggtccctgaccgattctctggctcccagtttggcgcctctgcctccctggccatcactgg
actccaggctgaggatgaggctgattattactgccagtcctatgacagtagtctgagtggtgtgatattcggcggaggg
accaagctgaccgtcctaggt (SEQ ID NO: 18)

Full VH
EVQLVQSGAEVKKPGASVKVSCKVSGYTLTELSMHWVRQAPGKGLEWMGGFDP
EDGETIYAQKFQGRVTMTEDTSTDTAYMELSSLRSEDTAVYYCARAYYGFDQWG
QGTLVTVSS (SEQ ID NO: 19)

DNA
gaagtgcagctggtgcagtctggggctgaggtgaagaagcctggggcctcagtgaaggtctcctgcaaggtttccgg
atacaccctcactgaattatccatgcactgggtgcgacaggctcctggaaaagggcttgagtggatgggaggttttgat
cctgaagatggtgaaacaatctacgcacagaagttccagggcagagtcaccatgaccgaggacacatctacagac
acagcctacatggagctgagcagcctgaggtctgaggacactgccgtgtattactgtgcgcgcgcttactacggtttcg
atcagtggggtcaaggtactctggtgaccgtctcctca (SEQ ID NO: 20)

scFv
PD-1-18
DIQMTQSPSSLSASVGDRVTITCRASQSISSYLNWYQQKPGKAPKLLIYAASSLQSG
VPSRFSGSGSGTDFTLTISSLQPEDFATYYCQQSYSTPLTFGGGTKVEIKR
GGGGSGGGGSGGGGS
EVQLVQSGAEVKKPGASVKVSCKVSGYTLTELSMHWVRQAPGKGLEWMGGFDP
EDGETIYAQKFQGRVTMTEDTSTDTAYMELSSLRSEDTAVYYCARAYYGFDQWG
QGTLVTVSSHHHHHHGAYPYDVPDYAS*
(SEQ ID NO: 21)

DNA (5'-3')
cagtctgtgttgacgcagccgccctcagtgtctggggcccagggcagagggtcaccatctcctgcactgggagcag
ctccaacatcggggcaggttatgctgtaaattggtaccagcttcttccaggaacagccccaaactcctcatctctacta
acaacaatcggccctcaggggtccctgaccgattctctggctcccagtttggcgcctctgcctccctggccatcactgg
actccaggctgaggatgaggctgattattactgccagtcctatgacagtagtctgagtggtgtgatattcggcggaggg
accaagctgaccgtcctaggtggtggtggtggtagcggcggcggcggctctggtggtggtggatcc
gaagtgcagctggtgcagtctggggctgaggtgaagaagcctggggcctcagtgaaggtctcctgcaaggtttccgg
atacaccctcactgaattatccatgcactgggtgcgacaggctcctggaaaagggcttgagtggatgggaggttttgat
cctgaagatggtgaaacaatctacgcacagaagttccagggcagagtcaccatgaccgaggacacatctacagac
acagcctacatggagctgagcagcctgaggtctgaggacactgccgtgtattactgtgcgcgcgcttactacggtttcg
atcagtggggtcaaggtactctggtgaccgtctcctca
(SEQ ID NO: 22)

TABLE 3

PD1-23

| Antigen | PD1 ECD-hIgG1 Fc fusion | | |
|---|---|---|---|
| CDRs: | 1 | 2 | 3 |
| VL | SSNIGNNA (SEQ ID NO: 23) | YND | AAWDDSVNGYV (SEQ ID NO: 24) |
| VH | GYTFTRFG (SEQ ID NO: 25) | ISVNNGNT (SEQ ID NO: 26) | ARYMYGRRDS (SEQ ID NO: 27) |

Full VL QAVLTQPPSMSEAPRQRVTISCSGSSSNIGNNAVNWYQQLPGKAPKLLIYYNDLLSS
GVSDRFSGSKSGTSASLAISGLQSEDEADYYCAAWDDSVNGYVFGTGTKVTVLG
(SEQ ID NO: 28)

DNA caggctgtgctgactcagccaccctcgatgtctgaagcccccaggcagagggtcaccatctcctgttctggaagcagc
tccaacatcggaaataatgctgtaaactggtaccagcagctcccaggaaaggctcccaaactcctcatctattataatg
atctgctgtcctcaggggtctctgaccgattctctggctccaagtctggcacctcagcctcccctggccatcagtgggctcc
agtctgaggatgaggctgattattactgtgcagcatgggatgacagtgtgaatggttatgtcttcggaactgggaccaag
gtcaccgtcctaggt (SEQ ID NO: 29)

Full VH EVQLVQSGAEVKKPGDSVKVSCKASGYTFTRFGFSWVRQAPGQGLEWMGWISVN
NGNTKYAQKYQGRVTMTTDTSTSTAYMELRSLRSDDTAVYYCARYMYGRRDSWG
QGTLVTVSS (SEQ ID NO: 30)

DNA Gaggtccagctggtgcagtctggagctgaggtgaagaagcctggggactcagtgaaggtctcctgcaaggcttctgg
ttacaccttaccagatttggtttcagctgggtgcgacaggcccctggacaagggcttgagtggatgggatggatcagc
gttaataatggtaacacaaagtatgcacagaagtaccagggcagagtcaccatgaccacagacacatccacgagc
acagcctacatggagctgaggagcctgaggtctgacgacactgccgtgtattactgtgcgcgctacatgtacggtcgtc
gtgattcttggggtcaaggtactctggtgaccgtctcctca
(SEQ ID NO: 31)

scFv PD-1-23
QAVLTQPPSMSEAPRQRVTISCSGSSSNIGNNAVNWYQQLPGKAPKLLIYYNDLLSS
GVSDRFSGSKSGTSASLAISGLQSEDEADYYCAAWDDSVNGYVFGTGTKVTVLG
GSRGGGGSGGGGSGGGGS
EVQLVQSGAEVKKPGDSVKVSCKASGYTFTRFGFSWVRQAPGQGLEWMGWISVN
NGNTKYAQKYQGRVTMTTDTSTSTAYMELRSLRSDDTAVYYCARYMYGRRDSWG
QGTLVTVSS GQHHHHHHGAYPYDVPDYAS*
(SEQ ID NO: 32)

DNA (5'-3') caggctgtgctgactcagccaccctcgatgtctgaagcccccaggcagagggtcaccatctcctgttctggaagcagc
tccaacatcggaaataatgctgtaaactggtaccagcagctcccaggaaaggctcccaaactcctcatctattataatg
atctgctgtcctcaggggtctctgaccgattctctggctccaagtctggcacctcagcctcccctggccatcagtgggctcc
agtctgaggatgaggctgattattactgtgcagcatgggatgacagtgtgaatggttatgtcttcggaactgggaccaag
gtcaccgtcctaggtctagaggtggtggtggtagcggcggcggcctctggtggtggtggatccgagtccag
ctggtgcagtctggagctgaggtgaagaagcctggggactcagtgaaggtctcctgcaaggcttctggttacacctttac
cagatttggtttcagctgggtgcgacaggcccctggacaagggcttgagtggatgggatggatcagcgttaataatggt
aacacaaagtatgcacagaagtaccagggcagagtcaccatgaccacagacacatccacgagcacagcctacat
ggagctgaggagcctgaggtctgacgacactgccgtgtattactgtgcgcgctacatgtacggtcgtcgtgattcttggg
gtcaaggtactctggtgaccgtctcctcagcggccagcaccatcaccatcaccatggcgcataccgtacgacgttc
cggactacgcttcttag (SEQ ID NO: 33)

TABLE 4

PD1-26

| Antigen | PD1 ECD-hIgG1 Fc fusion | | |
|---|---|---|---|
| CDRs: | 1 | 2 | 3 |
| VL | NIGSKS (SEQ ID NO: 34) | YDS | QVWDNHSDVV (SEQ ID NO: 35) |
| VH | RNKFSSYA (SEQ ID NO: 36) | ISGSGGTT (SEQ ID NO: 37) | ARWYSSYYDV (SEQ ID NO: 38) |

Full VL QSVLTQPPSVSVAPGKTARITCGGNNIGSKSVHWYQQKPGQAPVLVIYYDSDRPSG
IPERFSGSNSGNTATLTISRVEAGDEADYYCQVWDNHSDVVFGGGTKLTVLG
(SEQ ID NO: 39)

DNA Cagtctgtgctgactcagccaccctcagtgtcagtggccccaggaaagacggccaggattaccgtggggaaaca
acattggaagtaaaagtgtgcactggtaccagcagaagccaggccaggcccctgtgctggtcatctattatgatagcg
accggccctcagggatccctgagcgattctctggctccaactctgggaacacggccaccctgaccatcagcagggtc
gaagccggggatgaggccgactattactgtcaggtctgggataatcatagtgatgtggtattcggcggagggaccaag
ctgaccgtcctaggt (SEQ ID NO: 40)

TABLE 4-continued

PD1-26

| | |
|---|---|
| Full VH | QVQLVESGGGLVQPGGSLRLSCAASGYTRNKFSSYAMSWVRQAPGKGLEWVSGI<br>SGSGGTTYYADSVKGRFTISRDNSKNTQYLQLDSLRAEDTAVYYCARWYSSYYDV<br>WGQGTLVTVSS (SEQ ID NO: 41) |
| DNA | Caggtgcagctggtggagtctggggggaggcttggtacagcctggggggtccctgagactctcctgtgcagcctctgga<br>tacacccgtaacaaatttagcagctatgccatgagctgggtccgccaggctccagggaagggcctggaatgggtctc<br>aggtattagtggtagtggtggtactacatactatgcagactccgtgaagggccggttcaccatctccagagacaattcca<br>agaacacgcagtatctgcaattggacagcctgagagccgaggacacggccgtatattactgtgcgcgctggtactctt<br>cttactacgatgtttggggtcaaggtactctggtgaccgtctcctca<br>(SEQ ID NO: 42) |
| scFv<br>PD1-26 | QSVLTQPPSVSVAPGKTARITCGGNNIGSKSVHWYQQKPGQAPVLVIYYDSDRPSG<br>IPERFSGSNSGNTATLTISRVEAGDEADYYCQVWDNHSDVVFGGGTKLTVLGGGG<br>GSGGGGSGGGGS<br>QVQLVESGGGLVQPGGSLRLSCAASGYTRNKFSSYAMSWVRQAPGKGLEWVSGI<br>SGSGGTTYYADSVKGRFTISRDNSKNTQYLQLDSLRAEDTAVYYCARWYSSYYDV<br>WGQGTLVTVSS HHHHHHGAYPYDVPDYAS*<br>(SEQ ID NO: 43) |
| DNA<br>(5'-3') | cagtctgtgctgactcagccaccctcagtgtcagtggccccaggaaagacggccaggattacctgtgggggaaaca<br>acattggaagtaaaagtgtgcactggtaccagcagaagccaggccaggcccctgtgctggtcatctattatgatagcg<br>accggccctcagggatccctgagcgattctctggctccaactctgggaacacggccaccctgaccatcagcagggtc<br>gaagccggggatgaggccgactattactgtcaggtctgggataatcatagtgatgtggtattcggcggagggaccaag<br>ctgaccgtcctaggtggtggtggtggtagcggcggcggcggctctggtggtggtggatccaggtgcagctggtggag<br>tctggggggaggcttggtacagcctggggggtccctgagactctcctgtgcagcctctggatacacccgtaacaaattta<br>gcagctatgccatgagctgggtccgccaggctccagggaagggcctggaatgggtctcaggtattagtggtagtggtg<br>gtactacatactatgcagactccgtgaagggccggttcaccatctccagagacaattccaagaacacgcagtatctgc<br>aattggacagcctgagagccgaggacacggccgtatattactgtgcgcgctggtactcttcttactacgatgtttggggtc<br>aaggtactctggtgaccgtctcctcacaccatcaccatcaccatggcgcataccgtacgacgttccggactacgcttct<br>tag (SEQ ID NO: 44) |

TABLE 5

PD-1-27

| Antigen | PD1 ECD-hIgG1 Fc fusion | | |
|---|---|---|---|
| CDRs: | 1 | 2 | 3 |
| VL | NIGSKS<br>(SEQ ID NO: 34) | YDS | QVWDSSSDYV<br>(SEQ ID NO: 45) |
| VH | GFTFSSYA<br>(SEQ ID NO: 46) | ISGSGGST<br>(SEQ ID NO: 47) | ARNYISMFDS<br>(SEQ ID NO: 48) |

| | |
|---|---|
| Full VL | QSVLTQPPSVSVAPGKTARITCGGNNIGSKSVHWYQQRPGQAPVLVIYYDSDRPS<br>GIPERFSGSNSGNTATLTISRVEAGDEADYYCQVWDSSSDYVFGIGTKVTVLG<br>(SEQ ID NO: 49) |
| DNA | cagtctgtgctgactcagccaccctcagtgtcagtggccccaggaaagacggccaggattacctgtgggggaaaca<br>acattggaagtaaaagtgtgcactggtaccagcagaggccaggccaggcccctgtgctggtcatctattatgatagc<br>gaccggccctcagggatccctgagcgattctctggctccaactctgggaacacggccaccctgaccatcagcaggg<br>tcgaagccggggatgaggccgactattactgtcaggtgtgggatagtagtagtgattatgtcttcggaattgggaccaa<br>ggtcaccgtcctaggt (SEQ ID NO: 50) |
| Full VH | EVQLVESGGGLIQPGGSLRLSCAASGFTFSSYAMSWVRQAPGKGLEWVSAISGSG<br>GSTYYADSVKGRFTISRDNSKNTLYLQMNSLRAEDTAVYYCARNYISMFDSWGQG<br>TLVTVSS (SEQ ID NO: 51) |
| DNA | gaggtgcagctggtggagtctggaggaggcttgatccagcctggggggtccctgagactctcctgtgcagcctctgg<br>attcacctttagcagctatgccatgagctgggtccgccaggctccaggaagggggctggagtgggtctcagctattag<br>tggtagtggtagcacatactacgcagactccgtgaagggccggttcaccatctccagagacaattccaagaaca<br>cgctgtatctgcaaatgaacagcctgagagccgaggacacggccgtatattactgtgcgcgcaactacatctctatgtt<br>cgattcttggggtcaaggtactctggtgaccgtctcctca (SEQ ID NO: 52) |
| scFv<br>PD1-27 | QSVLTQPPSVSVAPGKTARITCGGNNIGSKSVHWYQQRPGQAPVLVIYYDSDRPS<br>GIPERFSGSNSGNTATLTISRVEAGDEADYYCQVWDSSSDYVFGIGTKVTVLG<br>GGGGSGGGGSGGGGS<br>EVQLVESGGGLIQPGGSLRLSCAASGFTFSSYAMSWVRQAPGKGLEWVSAISGSG<br>GSTYYADSVKGRFTISRDNSKNTLYLQMNSLRAEDTAVYYCARNYISMFDSWGQG<br>TLVTVSSHHHHHHGAYPYDVPDYAS*(SEQ ID NO: 53) |

TABLE 5-continued

PD-1-27

| | |
|---|---|
| DNA (5'-3') | cagtctgtgctgactcagccaccctcagtgtcagtggccccaggaaagacggccaggattacctgtgggggaaaca acattggaagtaaaagtgtgcactggtaccagcagaggccaggccaggcccctgtgctggtcatctattatgatagc gaccggccctcagggatccctgagcgattctctggctccaactctgggaacacggccaccctgaccatcagcaggg tcgaagccggggatgaggccgactattactgtcaggtgtgggatagtagtagtgattatgtcttcggaattgggaccaa ggtcaccgtcctaggtggtggtggtggtagcggcggcggcggctctggtggtggtggatccgaggtgcagctggtgg agtctggaggaggcttgatccagcctgggggtccctgagactctcctgtgcagcctctggattcacctttagcagctat gccatgagctgggtccgccaggctccagggaaggggctggagtgggtctcagctattagtggtagtggtggtagcac atactacgcagactccgtgaagggccggttcaccatctccagagacaattccaagaacacgctgtatctgcaaatga acagcctgagagccgaggacacggccgtatattactgtgcgcgcaactacatctctatgttcgattcttggggtcaagg tactctggtgaccgtctcctcacaccatcaccatcaccatggcgcatacccgtacgacgttccggactacgcttcttag (SEQ ID NO: 54) |

TABLE 6

PD-1-31

| Antigen | PD1 ECD hIgG1 Fc fusion | | |
|---|---|---|---|
| CDRs: | 1 | 2 | 3 |
| VL | NIGSKS<br>(SEQ ID NO: 34) | YDS | QVWDSSSDHV<br>(SEQ ID NO: 55) |
| VH | GFTFSSYA<br>(SEQ ID NO: 46) | ISGSGGST<br>(SEQ ID NO: 47) | ARGYSSYYDA<br>(SEQ ID NO: 56) |

| | |
|---|---|
| Full VL | QAVLTQPPSVSVAPGKTARITCGGNNIGSKSVHWYQQKPGQAPVLVIYYDSDRPS<br>GIPERFSGSNSGNTATLTISRVEAGDEADYYCQVWDSSSDHVFGTGTKVTVLG<br>(SEQ ID NO: 57) |
| DNA | caggctgtgctgactcagccaccctcagtgtcagtggccccaggaaagacggccaggattacctgtggggaaac aacattggaagtaaaagtgtgcactggtaccagcagaagccaggccaggcccctgtgctggtcatctattatgatag cgaccggccctcagggatccctgagcgattctctggctccaactctgggaacacggccaccctgaccatcagcagg gtcgaagccggggatgaggccgactattactgtcaggtgtgggatagtagtagtgatcatgtcttcggaactgggacc aaggtcaccgtcctaggt (SEQ ID NO: 58) |
| Full VH | QVQLVESGGGLVQPGGSLRLSCAASGFTFSSYAMSWVRQAPGKGLEWVSAISGS<br>GGSTYYADSVKGRFTISRDNSKNTLYLQMNSLRAEDTAVYYCARGYSSYYDAWG<br>QGTLVTVSS (SEQ ID NO: 59) |
| DNA | caggtgcagctggtggagtctggggggaggcttggtacagcctggggggtccctgagactctcctgtgcagcctctgg attcacctttagcagctatgccatgagctgggtccgccaggctccagggaaggggctggagtgggtctcagctattag tggtagtggtggtagcacatactacgcagactccgtgaagggccggttcaccatctccagagacaattccaagaaca cgctgtatctgcaaatgaacagcctgagagccgaggacacggccgtatattactgtgcgcgcggttactcttcttacta cgatgcttggggtcaaggtactctggtgaccgtctcctca (SEQ ID NO: 60) |
| scFv PD-1-31 | QAVLTQPPSVSVAPGKTARITCGGNNIGSKSVHWYQQKPGQAPVLVIYYDSDRPS<br>GIPERFSGSNSGNTATLTISRVEAGDEADYYCQVWDSSSDHVFGTGTKVTVLGGG<br>GGSGGGGSGGGGS<br>QVQLVESGGGLVQPGGSLRLSCAASGFTFSSYAMSWVRQAPGKGLEWVSAISGS<br>GGSTYYADSVKGRFTISRDNSKNTLYLQMNSLRAEDTAVYYCARGYSSYYDAWG<br>QGTLVTVSS HHHHHHGAYPYDVPDYAS*<br>(SEQ ID NO: 61) |
| DNA (5'-3') | caggctgtgctgactcagccaccctcagtgtcagtggccccaggaaagacggccaggattacctgtggggaaac aacattggaagtaaaagtgtgcactggtaccagcagaagccaggccaggcccctgtgctggtcatctattatgatag cgaccggccctcagggatccctgagcgattctctggctccaactctgggaacacggccaccctgaccatcagcagg gtcgaagccggggatgaggccgactattactgtcaggtgtgggatagtagtagtgatcatgtcttcggaactgggacc aaggtcaccgtcctaggtggtggtggtggtagcggcggcggcggctctggtggtggtggatcccaggtgcagctggt ggagtctggggggggcttggtacagcctggggggtccctgagactctcctgtgcagcctctggattcacctttagcagc tatgccatgagctgggtccgccaggctccagggaaggggctggagtgggtctcagctattagtggtagtggtggtagc acatactacgcagactccgtgaagggccggttcaccatctccagagacaattccaagaacacgctgtatctgcaaat gaacagcctgagagccgaggacacggccgtatattactgtgcgcgcggttactcttcttactacgatgcttggggtcaa ggtactctggtgaccgtctcctcacaccatcaccatcaccatggcgcatacccgtacgacgttccggactacgcttctta g (SEQ ID NO: 62) |

TABLE 7

PD-1-40

| Antigen | PD1 ECD-hIgG1 Fc fusion | | |
|---|---|---|---|
| CDRs: | 1 | 2 | 3 |
| VL | RSNIGENT<br>(SEQ ID NO: 63) | SNN | AAWDDRLNGYV<br>(SEQ ID NO: 64) |
| VH | GYTFTNYG<br>(SEQ ID NO: 65) | IGAQKGDT<br>(SEQ ID NO: 66) | ARSQGVPFDS<br>(SEQ ID NO: 67) |

| | |
|---|---|
| Full VL | QSVLTQPPSASGTPGQRVTISCSGSRSNIGENTVNWYQQLPGTAPKLLIYSNNQRP<br>SGVPDRFSGSKSGTSASLAISGLHSDDEADYFCAAWDDRLNGYVFGTGTKVTVLG<br>(SEQ ID NO: 68) |
| DNA | Cagtctgtgttgactcagccaccctcagcgtctgggaccccgggcagagagtcaccatctcttgttctggaagcaggt<br>ccaacatcggagaaaatactgtcaactggtaccagcagctcccaggaacggcccccaaactcctcatctacagtaat<br>aatcagcggccctcaggggtccctgaccgattctctggctccaagtctggcacctcagcctccctggccatcagtgggc<br>ttcactctgacgatgaggctgactattttgtgcagcatgggatgaccgcctcaatggttatgtcttcggaactgggaccaa<br>ggtcaccgtcctaggt<br>(SEQ ID NO: 69) |
| Full VH | QVQLVQSGPEVKKPGASVKVSCKASGYTFTNYGFTWVRQAPGQGLEWMGWIGAQ<br>KGDTEYAQKFQGRVTMTTDTSTSTVYLELRSLRSDDTAVYYCARSQGVPFDSWGQ<br>GTLVTVSS (SEQ ID NO: 70) |
| DNA | Caggtgcagctggtgcaatctggacctgaggtgaagaagcctggggcctcggtgaaggtctcctgcaaggcttctggt<br>tacacctttaccaactatggtttcacctgggtgcgacaggcccctggacaaggtcttgagtggatgggatggatcggcg<br>ctcaaaagggtgacacagagtatgcacaaaaattccagggcagagtcaccatgacgacagacatccacgagc<br>acagtctacttggagttgaggagcctgaggtctgacgacacggccgtgtattactgtgcgcgctctcagggtgttccgttc<br>gattcttgggtcaaggtactctggtgaccgtctcctca<br>(SEQ ID NO: 71) |
| scFv<br>PD-1-<br>40 | QSVLTQPPSASGTPGQRVTISCSGSRSNIGENTVNWYQQLPGTAPKLLIYSNNQRP<br>SGVPDRFSGSKSGTSASLAISGLHSDDEADYFCAAWDDRLNGYVFGTGTKVTVLG<br>GGGGSGGGGSGGGGS<br>QVQLVQSGPEVKKPGASVKVSCKASGYTFTNYGFTWVRQAPGQGLEWMGWIGAQ<br>KGDTEYAQKFQGRVTMTTDTSTSTVYLELRSLRSDDTAVYYCARSQGVPFDSWGQ<br>GTLVTVSSHHHHHHGAYPYDVPDYAS*<br>(SEQ ID NO: 72) |
| DNA<br>(5'-3') | cagtctgtgttgactcagccaccctcagcgtctgggaccccgggcagagagtcaccatctcttgttctggaagcaggt<br>ccaacatcggagaaaatactgtcaactggtaccagcagctcccaggaacggcccccaaactcctcatctacagtaat<br>aatcagcggccctcaggggtccctgaccgattctctggctccaagtctggcacctcagcctccctggccatcagtgggc<br>ttcactctgacgatgaggctgactattttgtgcagcatgggatgaccgcctcaatggttatgtcttcggaactgggaccaa<br>ggtcaccgtcctaggtggtggtggtggtagcggcggcggcggctctggtggtggtggatcccaggtgcagctggtgca<br>atctggacctgaggtgaagaagcctggggcctcggtgaaggtctcctgcaaggcttctggttacacctttaccaactatg<br>gtttcacctgggtgcgacaggcccctggacaaggtcttgagtggatgggatggatcggcgctcaaaagggtgacaca<br>gagtatgcacaaaaattccagggcagagtcaccatgacgacagacatccacgagcacagtctacttggagttga<br>ggagcctgaggtctgacgacacggccgtgtattactgtgcgcgctctcagggtgttccgttcgattcttgggtcaaggta<br>ctctggtgaccgtctcctcacaccatcaccatcaccatggcgcataccgtacgacgttccggactacgcttcttag<br>(SEQ ID NO: 73) |

TABLE 8

PD-1-36

| Antigen | PD1 ECD hIgG1 Fc fusion | | |
|---|---|---|---|
| CDRs: | 1 | 2 | 3 |
| VL | RSNIGSNT<br>(SEQ ID NO: 74) | NNN | ATWDDSLNEYV<br>(SEQ ID NO: 75) |
| VH | GYTFTRYG<br>(SEQ ID NO: 76) | ISGYNGNT<br>(SEQ ID NO: 77) | ARHGYGYHGD<br>(SEQ ID NO: 78) |

| | |
|---|---|
| Full VL | QSVLTQPPSASATPGQRGTISCSGGRSNIGSNTVNWYQQLPGTAPKLLIYNNNLRP<br>SGVPDRFSGSKSGTSASLAIRGLQSEDEADYYCATWDDSLNEYVFGTGTKVTVLG<br>(SEQ ID NO: 79) |
| DNA | Cagtctgtgttgactcagccaccctcagcgtctgcgaccccgggcagaggggcaccatttcgtgttctggaggcagg<br>tccaacatcggaagtaacactgttaactggtaccagcagctcccaggaacggcccccaaactcctcatctataataat<br>aatctgcggccctcaggggtccctgaccgattctctggctccaagtctggcacctcagcctccctggccatcaggggc |

TABLE 8-continued

PD-1-36

| | |
|---|---|
| | tccagtctgaggatgaggctgattattactgtgcaacatgggatgacagcctgaatgaatatgtcttcggaactgggacc<br>aaggtcaccgtcctaggt (SEQ ID NO: 80) |
| Full VH | QVQLVQSGAEVKKPGASVKVSCKASGYTFTRYGISWVRQAPGQGLEWMGWISGY<br>NGNTNYAQKLQGRVTMTTDTSTSTAYMELRSLRSDDTAVYYCARHGYGYHGDWG<br>QGTLVTVSS (SEQ ID NO: 81) |
| DNA | Caggtgcagctggtgcaatctggagctgaggtgaagaagcctgggcctcagtgaaggtctcctgcaaggcttctggt<br>tacacctttaccagatatggtatcagctgggtgcgacaggcccctggacaagggcttgagtggatgggatggatcagc<br>ggttacaacggtaacacaaactatgcacagaagctccagggcagagtcaccatgaccacagacacatccacgagc<br>acagcctacatggagctgaggagcctgaggtctgacgacacggccgtgtattactgtgcgcgccatggttacggttac<br>catggtgattggggtcaaggtactctggtgaccgtctcctca<br>(SEQ ID NO: 82) |
| scFv<br>PD-1-<br>36 | QSVLTQPPSASATPGQRGTISCSGGRSNIGSNTVNWYQQLPGTAPKLLIYNNNLRP<br>SGVPDRFSGSKSGTSASLAIRGLQSEDEADYYCATWDDSLNEYVFGTGTKVTVLG<br>GGGGSGGGGSGGGGS<br>QVQLVQSGAEVKKPGASVKVSCKASGYTFTRYGISWVRQAPGQGLEWMGWISGY<br>NGNTNYAQKLQGRVTMTTDTSTSTAYMELRSLRSDDTAVYYCARHGYGYHGDWG<br>QGTLVTVSS HHHHHHGAYPYDVPDYAS*<br>(SEQ ID NO: 83) |
| DNA<br>(5'-3') | cagtctgtgttgactcagccaccctcagcgtctgcgaccccccgggcagaggggcaccatttcgtgttctggaggcaggt<br>ccaacatcggaagtaacactgttaactggtaccagcagctcccaggaacggcccccaaactcctcatctataataata<br>atctgcggccctcaggggtccctgaccgattctctggctccaagtctggcacctcagcctcctggccatcaggggct<br>ccagtctgaggatgaggctgattattactgtgcaacatgggatgacagcctgaatgaatatgtcttcggaactgggacc<br>aaggtcaccgtcctaggtggtggtggtggtagcggcggcggcggctctggtggtggtggatcc<br>caggtgcagctggtgcaatctggagctgaggtgaagaagcctgggcctcagtgaaggtctcctgcaaggcttctggt<br>tacacctttaccagatatggtatcagctgggtgcgacaggcccctggacaagggcttgagtggatgggatggatcagc<br>ggttacaacggtaacacaaactatgcacagaagctccagggcagagtcaccatgaccacagacacatccacgagc<br>acagcctacatggagctgaggagcctgaggtctgacgacacggccgtgtattactgtgcgcgccatggttacggttac<br>catggtgattggggtcaaggtactctggtgaccgtctcctcacaccatcaccatcaccatggcgcataccgtacgacg<br>ttccggactacgcttctag (SEQ ID NO: 84) |

TABLE 9

PD-1-37

| Antigen | PD1 ECD hIgG1 Fc fusion | | |
|---|---|---|---|
| CDRs: | 1 | 2 | 3 |
| VL | SSNIGAGYV<br>(SEQ ID NO: 85) | HNN | QSYDSSLSGWV<br>(SEQ ID NO: 86) |
| VH | GFTFKDYY<br>(SEQ ID NO: 87) | ISTSGNSV<br>(SEQ ID NO: 88) | ARSPGHSDYDS<br>(SEQ ID NO: 89) |
| Full VL | QSVLTQPPSVSGAPGQRVTISCTGSSSNIGAGYVVQWYQQLPGTAPKLLIYHNNDR<br>PSGVPYRFSGSKSGTSASLAITGLQAEDEADYYCQSYDSSLSGWVFGGGTKLTVLG<br>(SEQ ID NO: 90) | | |
| DNA | Cagtctgtgctgacgcagccgccctcagtgtctggggcccagggcagagggtcaccatctcctgtactgggagcag<br>ctccaacatcggggcaggttatgttgtacagtggtatcagcagcttccaggaacagcccccaaactcctcatctatcata<br>acaacgatcggccctcaggggtccctaccgattctctggctccaagtctggcacctcagcctcctggccatcactgg<br>gctccaggctgaggatgaggctgattattactgccagtcctatgacagcagcctgagtggtgggtgttcggcggaggg<br>accaagctgaccgtcctaggt<br>(SEQ ID NO: 91) | | |
| Full VH | EVQLVESGGGLVKPGGSLRLSCAASGFTFKDYYMNWIRQAPGKGLEWISHISTSGN<br>SVDYADSVKGRFTISRDNAKNSLYLQMNSLRAEDTAVYYCARSPGHSDYDSWGQG<br>TLVTVSS (SEQ ID NO: 92) | | |
| DNA | gaggtgcagctggtggagtctgggggaggcctagtcaagcctggagggtccctgagactctcctgtgcagcctctgga<br>ttcacctttaaagactactacatgaactggatccgccaggctccagggaagggcctggagtggatttcacacattagta<br>ccagcggtaatagtgtagattatgcagactctgtcaagggccggttcaccatctccagggacaacgccaagaattcac<br>tgtacctgcaaatgaacagcctgagagccgaggacacggccgtatattactgtgcgcgctctccgggtcattctgacta<br>cgattcttggggtcaaggtactctggtgaccgtctcctca<br>(SEQ ID NO: 93) | | |

TABLE 9-continued

PD-1-37

| | |
|---|---|
| scFv PD-1-37 | QSVLTQPPSVSGAPGQRVTISCTGSSSNIGAGYVVQWYQQLPGTAPKLLIYHNNDR<br>PSGVPYRFSGSKSGTSASLAITGLQAEDEADYYCQSYDSSLSGWVFGGGTKLTVLG<br>GGGGSGGGGSGGGGS<br>EVQLVESGGGLVKPGGSLRLSCAASGFTFKDYYMNWIRQAPGKGLEWISHISTSGN<br>SVDYADSVKGRFTISRDNAKNSLYLQMNSLRAEDTAVYYCARSPGHSDYDSWGQG<br>TLVTVSS HHHHHHGAYPYDVPDYAS* (SEQ ID NO: 94) |
| DNA (5'-3') | cagtctgtgctgacgcagccgccctcagtgtctggggcccagggcagagggtcaccatctcctgtactgggagcag<br>ctccaacatcggggcaggttatgttgtacagtggtatcagcagcttccaggaacagcccccaaactcctcatctatcata<br>acaacgatcggccctcaggggtcccttaccgattctctggctccaagtctggcacctcagcctcctggccatcactgg<br>gctccaggctgaggatgaggctgattattactgccagtcctatgacagcagcctgagtggttgggtgttcggcggaggg<br>accaagctgaccgtcctaggtggtggtggtggtagcggcggcggcggctctggtggtggtggatcc<br>gaggtgcagctggtggagtctggggggaggcctagtcaagcctggagggtccctgagactctcctgtgcagcctctgga<br>ttcacctttaaagactactacatgaactggatccgccaggctccagggaagggcctggagtggatttcacacattagta<br>ccagcggtaatagtgtagattatgcagactctgtcaaggccgcgttcaccatctccagggacaacgccaagaattcac<br>tgtacctgcaaatgaacagcctgagagccgaggacacggccgtatattactgtgcgcgctctccgggtcattctgacta<br>cgattcttggggtcaaggtactctggtgaccgtctcctca<br>caccatcaccatcaccatggcgcatacccgtacgacgttccggactacgcttcttag (SEQ ID NO: 95) |

TABLE 10

PD-1-19

| Antigen | PD1 ECD hIgG1 Fc fusion | | |
|---|---|---|---|
| CDRs: | 1 | 2 | 3 |
| VL | NIGDKS<br>(SEQ ID NO: 96) | YDS | QVWASGTDHPYVI<br>(SEQ ID NO: 97) |
| VH | GFTFSSYA<br>(SEQ ID NO: 46) | ISGSGGST<br>(SEQ ID NO: 47) | ARMYGSYTDM<br>(SEQ ID NO: 98) |

| | |
|---|---|
| Full VL | SYVLTQPPSVSVAPGKTARITCGGNNIGDKSVHWYQQKPGQAPVLVIYYDSDRPSGI<br>PERFSGSNSGNTATLTISRVEAGDEADYYCQVWASGTDHPYVIFGGGTKVTVLG<br>(SEQ ID NO: 99) |
| DNA | Tcctatgtgctgactcagccaccctcagtgtcagtggcccaggaaagacggccaggattaccgtgggggaaaca<br>acattggagataaaagtgtgcactggtaccagcagaagccaggccaggcccctgtgctggtcatctattatgatagcg<br>accggccctcagggatccctgagcgattctctggctccaactctgggaacacggccaccctgaccatcagcagggtc<br>gaagccggggacgaggccgactattactgtcaggtgtgggctagtggtactgatcatccctatgtgatattcggcggag<br>ggaccaaggtcaccgtcctaggt<br>(SEQ ID NO: 100) |
| Full VH | EVQLVESGGGLVQPGGSLRLSCAASGFTFSSYAMSWVRQAPGKGLEWVSAISGSG<br>GSTYYADSVKGRFTISRDNSKNTLYLQMNSLRAEDTAVYYCARMYGSYTDMWGQG<br>TLVTVSS (SEQ ID NO: 101) |
| DNA | Gaggtgcagctggtggagtctggggggaggcttggtacagcctggggggtccctgagactctcctgtgcagcctctgga<br>ttcacctttagcagctatgccatgagctgggtccgccaggctccagggaaggggctggagtgggtctcagctattagtg<br>gtagtggtggtagcacatactacgcagactccgtgaagggccggttcaccatctccagagacaattccaagaacacg<br>ctgtatctgcaaatgaacagcctgagagccgaggacacggccgtatattactgtgcgcgcatgtacggttcttacactg<br>atatgtggggtcaaggtactctggtgaccgtctcctca (SEQ ID NO: 102) |
| scFv PD-1-19 | SYVLTQPPSVSVAPGKTARITCGGNNIGDKSVHWYQQKPGQAPVLVIYYDSDRPSGI<br>PERFSGSNSGNTATLTISRVEAGDEADYYCQVWASGTDHPYVIFGGGTKVTVLGGGG<br>GGSGGGGSGGGGSEVQLVESGGGLVQPGGSLRLSCAASGFTFSSYAMSWVRQA<br>PGKGLEWVSAISGSGGSTYYADSVKGRFTISRDNSKNTLYLQMNSLRAEDTAVYYC<br>ARMYGSYTDMWGQGTLVTVSS HHHHHHGAYPYDVPDYAS* (SEQ ID NO: 103) |
| DNA (5'-3') | tcctatgtgctgactcagccaccctcagtgtcagtggccccaggaaagacggccaggattaccgtgggggaaacaa<br>cattggagataaaagtgtgcactggtaccagcagaagccaggccaggcccctgtgctggtcatctattatgatagcga<br>ccggccctcagggatccctgagcgattctctggctccaactctgggaacacggccaccctgaccatcagcagggtcg<br>aagccggggacgaggccgactattactgtcaggtgtgggctagtggtactgatcatccctatgtgatattcggcggagg<br>gaccaaggtcaccgtcctaggtggtggtggtggtagcggcggcggcggctctggtggtggtggatcc<br>gaggtgcagctggtggagtctggggggaggcttggtacagcctggggggtccctgagactctcctgtgcagcctctggat<br>tcacctttagcagctatgccatgagctgggtccgccaggctccagggaaggggctggagtgggtctcagctattagtgg<br>tagtggtggtagcacatactacgcagactccgtgaagggccggttcaccatctccagagacaattccaagaacacgc<br>tgtatctgcaaatgaacagcctgagagccgaggacacggccgtatattactgtgcgcgcatgtacggttcttacactgat<br>atgtggggtcaaggtactctggtgaccgtctcctcacaccatcaccatcaccatggcgcatacccgtacgacgttccgg<br>actacgcttcttag (SEQ ID NO: 104) |

TABLE 11

PD-1-14

| Antigen | PD1 ECD hIgG1 Fc fusion | | |
|---|---|---|---|
| CDRs: | 1 | 2 | 3 |
| VL | SSNIGYNY<br>(SEQ ID NO: 105) | RNN | TSWDDSLSGYV<br>(SEQ ID NO: 106) |
| VH | GNAFTNFY<br>(SEQ ID NO: 107) | INPSGTDLT<br>(SEQ ID NO: 108) | ARQYAYGYSGFDM<br>(SEQ ID NO: 109) |

Full VL QSVLTQPPSASGTPGQRVTISCSGSSSNIGYNYVYWYQQLPGTAPKLLISRNNQRP
SGVPDRFSGSKSGTSASLAISGLRSEDEADYYCTSWDDSLSGYVFGPGTKVTVLG
(SEQ ID NO: 110)

DNA cagtctgtgctgactcagccaccctcagcgtctgggaccccgggcagagggtcaccatctcttgttctggaagcagct
ccaacatcggatataattatgtatactggtaccagcagctcccaggaacggccccaaactcctcatctctagaaataa
tcagcggccctcaggggtccctgaccgattctctggctccaagtctggcacctcagcctccctggccatcagtgggctc
cggtccgaggatgaggctgactattactgtacatcgtgggatgacagcctgagtggttatgtcttcggacctgggacca
aggtcaccgtcctaggt (SEQ ID NO: 111)

Full VH EVQLVQSGAEVKKPGASVKVSCKASGNAFTNFYIHWVRQAPGQGLEWMGLINPSG
TDLTRYAQKFQGRVTMTRDTPTSTVYMELSSLRSDDTAVYYCARQYAYGYSGFDM
WGQGTLVTVSS (SEQ ID NO: 112)

DNA Gaagtgcagctggtgcagtctggggctgaggtgaagaagcctggggcctcagtgaaggtttcctgcaaggcatctgg
aaacgccttcaccaacttctatatacactgggtgcgacaggcccctggacaagggcttgagtggatgggattaatcaa
cccctagtggtactgacctcacaaggtacgcacagaagttccagggcagagtcaccatgaccagggacacgccac
gagcacagtctacatggagcagcctgaggtctgacgacacggctgtgtattactgtgcgcgccagtacgctta
cggttactctggtttcgatatgtggggtcaaggtactctggtgaccgtctcctca
(SEQ ID NO: 113)

scFv QSVLTQPPSASGTPGQRVTISCSGSSSNIGYNYVYWYQQLPGTAPKLLISRNNQRP
PD-1- SGVPDRFSGSKSGTSASLAISGLRSEDEADYYCTSWDDSLSGYVFGPGTKVTVLGG
14 GGGSGGGGSGGGGS
EVQLVQSGAEVKKPGASVKVSCKASGNAFTNFYIHWVRQAPGQGLEWMGLINPSG
TDLTRYAQKFQGRVTMTRDTPTSTVYMELSSLRSDDTAVYYCARQYAYGYSGFDM
WGQGTLVTVSSHHHHHHGAYPYDVPDYAS* (SEQ ID NO: 114)

DNA cagtctgtgctgactcagccaccctcagcgtctgggaccccgggcagagggtcaccatctcttgttctggaagcagct
(5'-3') ccaacatcggatataattatgtatactggtaccagcagctcccaggaacggccccaaactcctcatctctagaaataa
tcagcggccctcaggggtccctgaccgattctctggctccaagtctggcacctcagcctccctggccatcagtgggctc
cggtccgaggatgaggctgactattactgtacatcgtgggatgacagcctgagtggttatgtcttcggacctgggacca
aggtcaccgtcctaggtggtggtggtggtagcggcggcggcggctctggtggtggtggatccgaagtgcagctggtgc
agtctggggctgaggtgaagaagcctggggcctcagtgaaggtttcctgcaaggcatctggaaacgccttcaccaact
tctatatacactgggtgcgacaggcccctggacaagggcttgagtggatgggattaatcaaccctagtggtactgacct
cacaaggtacgcacagaagttccagggcagagtcaccatgaccagggacacgcccacgagcacagtctacatgg
agctgagcagcctgaggtctgacgacacggctgtgtattactgtgcgcgccagtacgcttacggttactctggtttcgata
tgtggggtcaaggtactctggtgaccgtctcctca
caccatcaccatcaccatggcgcatacccgtacgacgttccggactacgcttcttag (SEQ ID NO: 115)

45

TABLE 12

PD-1-47

| Antigen | PD1 ECD hIgG1 Fc fusion | | |
|---|---|---|---|
| CDRs: | 1 | 2 | 3 |
| VL | QSVSNW<br>(SEQ ID NO: 116) | AAS | QQSYSTPIT<br>(SEQ ID NO: 117) |
| VH | GYTFTSYY<br>(SEQ ID NO: 118) | INPNTGGS<br>(SEQ ID NO: 119) | ARGDVTYDE<br>(SEQ ID NO: 120) |

Full VL DIQMTQSPSSVSASVGDRVTITCRASQSVSNWLAWYQLKPGKAPKLLIYAASSLQS
GVPSRFSGSGSGTDFTLTISSLQPEDFATYYCQQSYSTPITFGGGTKVEIKR
(SEQ ID NO: 121)

DNA Gacatccagatgacccagtctccatcttccgtgtctgcatctgtaggagacagagtcaccatcacttgtcgggcgagtc
agagtgttagcaactggttagcctggtatcaactgaaaccagggaaagccccctaagctcctgatctatgctgcatccag
tttgcaaagtggggtcccatcaaggttcagtggcagtggatctgggacagatttcactctcaccatcagcagtctgcaac
ctgaagattttgcaacttactactgtcaacagagttacagtaccccgatcaccttcggcggagggaccaaggtggagat
caaacgt (SEQ ID NO: 122)

TABLE 12-continued

PD-1-47

| | |
|---|---|
| Full VH | QVQLVQSGAEVKKPGTSVKVSCKASGYTFTSYYIHWVRQAPGQGLEWMGWINPNT<br>GGSNFAQKFQGRVTMTRDTSISTAYMELNRLRSDDTAVYYCARGDVTYDEWGQGT<br>LVTVSS (SEQ ID NO: 123) |
| DNA | Caggtccagctggtacagtctggggctgaggtgaagaagcctgggacctcagtgaaggtctcctgcaaggcttctgg<br>atacaccttcacctcctactatatacactgggtgcgacaggcccctggacaagggcttgagtggatgggatggatcaa<br>ccctaacactggtggctcaaactttgcacagaagtttcagggcagggtcaccatgaccagggacacgtccatcagca<br>cagcctacatggagctgaacaggctgaggtctgacgacacggccgtgtattactgtgcgcgcggtgacgttacttacg<br>atgaatgggggtcaaggtactctggtgaccgtctcctca (SEQ ID NO: 124) |
| scFv<br>PD-1-<br>47 | DIQMTQSPSSVSASVGDRVTITCRASQSVSNWLAWYQLKPGKAPKLLIYAASSLQS<br>GVPSRFSGSGSGTDFTLTISSLQPEDFATYYCQQSYSTPITFGGGTKVEIKR<br>GGGGSGGGGSGGGGS<br>QVQLVQSGAEVKKPGTSVKVSCKASGYTFTSYYIHWVRQAPGQGLEWMGWINPNT<br>GGSNFAQKFQGRVTMTRDTSISTAYMELNRLRSDDTAVYYCARGDVTYDEWGQGT<br>LVTVSS<br>HHHHHHGAYPYDVPDYAS* (SEQ ID NO: 125) |
| DNA<br>(5'-3') | gacatccagatgacccagtctccatcttccgtgtctgcatctgtaggagacagagtcaccatcacttgtcgggcgagtca<br>gagtgttagcaactggttagcctggtatcaactgaaaccagggaaagcccctaagctcctgatctatgctgcatccagtt<br>tgcaaagtggggtcccatcaaggttcagtggcagtggatctgggacagatttcactctcaccatcagcagtctgcaacc<br>tgaagattttgcaacttactactgtcaacagagttacagtaccccgatcaccttcggcggagggaccaaggtggagatc<br>aaacgtggtggtggtagcggcggcggcggctctggtggtggtggatcc<br>caggtccagctggtacagtctggggctgaggtgaagaagcctgggacctcagtgaaggtctcctgcaaggcttctgga<br>tacaccttcacctcctactatatacactgggtgcgacaggcccctggacaagggcttgagtggatgggatggatcaac<br>cctaacactggtggctcaaactttgcacagaagtttcagggcagggtcaccatgaccagggacacgtccatcagcac<br>agcctacatggagctgaacaggctgaggtctgacgacacggccgtgtattactgtgcgcgcggtgacgttacttacgat<br>gaatgggggtcaaggtactctggtgaccgtctcctcacaccatcaccatcaccatggcgcataccgtacgacgttccg<br>gactacgcttcttag (SEQ ID NO: 126) |

TABLE 13

PD-1-46

| Antigen | PD1 ECD hIgG1 Fc fusion | | |
|---|---|---|---|
| CDRs: | 1 | 2 | 3 |
| VL | NIGSKS<br>(SEQ ID NO: 34) | YDD | QVWDINDHYV<br>(SEQ ID NO: 127) |
| VH | GFTFSSYA<br>(SEQ ID NO: 46) | ISGSGGST<br>(SEQ ID NO: 47) | ARSQASFMDI<br>(SEQ ID NO: 128) |

| | |
|---|---|
| Full VL | SYELTQPPSVSVAPGKTASITCGGNNIGSKSVHWYQQKPGQAPVLVIYYDDMRPSG<br>IPERFSGSSSGNTATLTISPVEAGDEADYYCQVWDINDHYVFASGTKVTVLG<br>(SEQ ID NO: 129) |
| DNA | Tcctatgagctgactcagccaccctcagtgtcagtggccccaggaaagacggccagcattacctgtgggggaaaca<br>acattggaagtaaaagtgtgcactggtaccagcagaagccaggccaggcccctgtgctggtcatctattatgatgacat<br>gcggccctcaggtatccctgagcgattctctggctccagctctgggaacacggccaccctgaccatcagcccggtcga<br>agccggggatgaggccgactattactgtcaggtgtgggatattaatgatcattatgtcttcgcatcggggaccaaggtca<br>ccgtcctaggt (SEQ ID NO: 130) |
| Full VH | EVQLVESGGGLVQPGGSLRLSCAASGFTFSSYAMSWVRQAPGKGLEWVSAISGSG<br>GSTYYADSVKGRFTISRDNSKNTLYLQMNSLRAEDTAVYYCARSQASFMDIWGQGT<br>LVTVSS (SEQ ID NO: 131) |
| DNA | Gaggtgcagctggtggagtctggggggaggcttggtacagcctggggggtccctgagactctcctgtgcagcctctgga<br>ttcacctttagcagctatgccatgagctgggtccgccaggctccagggaaggggctggagtgggtctcagctattagtg<br>gtagtggtggtagcacatactacgcagaccgtgaagggccggttcaccatctccagagacaattccaagaacacg<br>ctgtatctgcaaatgaacagcctgagagccgaggacacggccgtatattactgtgcgcgctctcaggcttcttttcatgga<br>tatctggggtcaaggtactctggtgaccgtctcctca (SEQ ID NO: 132) |
| scFv<br>PD-1-<br>46 | SYELTQPPSVSVAPGKTASITCGGNNIGSKSVHWYQQKPGQAPVLVIYYDDMRPSG<br>IPERFSGSSSGNTATLTISPVEAGDEADYYCQVWDINDHYVFASGTKVTVLGGGGG<br>SGGGGSGGGGS<br>EVQLVESGGGLVQPGGSLRLSCAASGFTFSSYAMSWVRQAPGKGLEWVSAISGSG<br>GSTYYADSVKGRFTISRDNSKNTLYLQMNSLRAEDTAVYYCARSQASFMDIWGQGT<br>LVTVSS HHHHHHGAYPYDVPDYAS* (SEQ ID NO: 133) |
| DNA<br>(5'-3') | tcctatgagctgactcagccaccctcagtgtcagtggccccaggaaagacggccagcattacctgtgggggaaacaa<br>cattggaagtaaaagtgtgcactggtaccagcagaagccaggccaggcccctgtgctggtcatctattatgatgacatg<br>cggccctcaggtatccctgagcgattctctggctccagctctgggaacacggccaccctgaccatcagcccggtcgaa |

TABLE 13-continued

PD-1-46

```
gccggggatgaggccgactattactgtcaggtgtgggatattaatgatcattatgtcttcgcatcggggaccaaggtcac
cgtcctaggtggtggtggtggtagcggcggcggcggctctggtggtggtggatccgaggtgcagctggtggagtctgg
gggaggcttggtacagcctggggggtccctgagactctcctgtgcagcctctggattcacctttagcagctatgccatga
gctgggtccgccaggctccaggaaggggctggagtgggtctcagctattagtggtagtggtggtagcacatactacg
cagactccgtgaagggccggttcaccatctccagagacaattccaagaacacgctgtatctgcaaatgaacagcctg
agagccgaggacacggccgtatattactgtgcgcgctctcaggcttctttcatggatatctggggtcaaggtactctggtg
accgtctcctca caccatcaccatcaccatggcgcatacccgtacgacgttccggactacgcttcttag
(SEQ ID NO: 134)
```

TABLE 14

PD-1-42

| | | | |
|---|---|---|---|
| Antigen | PD1 ECD hIgG1 Fc fusion | | |
| CDRs: | 1 | 2 | 3 |
| VL | NIGSKS<br>(SEQ ID NO: 34) | DDS | QVWDSSSDQGV<br>(SEQ ID NO: 135) |
| VH | GFTFSSYA<br>(SEQ ID NO: 46) | IGTGGGT<br>(SEQ ID NO: 136) | ARGTGYDGDQ<br>(SEQ ID NO: 137) |
| Full VL | LPVLTQPPSVSVAPGQTARITCGGNNIGSKSVHWYQQKPGQAPVLVVYDDSDRPS<br>GIPERFSGSNSGNTATLTISRVEAGDEADYYCQVWDSSSDQGVFGTGTKVTVLG<br>(SEQ ID NO: 138) | | |
| DNA | Ctgcctgtgctgactcagccaccctcggtgtcagtggccccaggacagacggccaggatcacctgtgggggaaaca<br>acattggaagtaaaagtgtgcactggtaccagcagaagccaggccaggcccctgtgctggtcgtctatgatgatagcg<br>accggcccctcagggatccctgagcgattctctggctccaattctgggaacacggccaccctgaccatcagcagggtcg<br>aagccggggatgaggccgactattactgtcaggtgtgggatagtagtagtgatcagggcgtcttcggaactgggacca<br>aggtcaccgtcctaggt<br>(SEQ ID NO: 139) | | |
| Full VH | EVQLVQSGGGLVQPRGSLRLSCAGSGFTFSSYAMHWVRQAPGKGLEWVSAIGTG<br>GGTYYADSVKGRFTISRDNAKNSLYLQMNSLRAEDTAMYYCARGTGYDGDQWGQ<br>GTLVTVSS (SEQ ID NO: 140) | | |
| DNA | Gaagtgcagctggtgcagtctggggggaggcttggtacagcctaggggggtccctgagactctcctgtgcaggctctgga<br>ttcaccttcagtagctatgctatgcactgggttcgccaggctccaggaaaaggtctggagtgggtatcagctattggtact<br>ggtggtggcacatactatgcagactccgtgaagggccgattcaccatctccagggacaatgccaagaactccttgtat<br>cttcaaatgaacagcctgagagccgaggacaccgccatgtattactgtgcgcgcggtactggttacgacggtgatcag<br>tggggtcaaggtactctggtgaccgtctcctca<br>(SEQ ID NO: 141) | | |
| scFv<br>PD-1-<br>42 | LPVLTQPPSVSVAPGQTARITCGGNNIGSKSVHWYQQKPGQAPVLVVYDDSDRPS<br>GIPERFSGSNSGNTATLTISRVEAGDEADYYCQVWDSSSDQGVFGTGTKVTVLG<br>GGGGSGGGGSGGGGS<br>EVQLVQSGGGLVQPRGSLRLSCAGSGFTFSSYAMHWVRQAPGKGLEWVSAIGTG<br>GGTYYADSVKGRFTISRDNAKNSLYLQMNSLRAEDTAMYYCARGTGYDGDQWGQ<br>GTLVTVSS HHHHHHGAYPYDVPDYAS*<br>(SEQ ID NO: 142) | | |
| DNA<br>(5'-3') | ctgcctgtgctgactcagccaccctcggtgtcagtggccccaggacagacggccaggatcacctgtgggggaaaca<br>acattggaagtaaaagtgtgcactggtaccagcagaagccaggccaggcccctgtgctggtcgtctatgatgatagcg<br>accggcccctcagggatccctgagcgattctctggctccaattctgggaacacggccaccctgaccatcagcagggtcg<br>aagccggggatgaggccgactattactgtcaggtgtgggatagtagtagtgatcagggcgtcttcggaactgggacca<br>aggtcaccgtcctaggtggtggtggtggtagcggcggcggcggctctggtggtggtggatcc<br>gaagtgcagctggtgcagtctggggggaggcttggtacagcctaggggggtccctgagactctcctgtgcaggctctggat<br>tcaccttcagtagctatgctatgcactgggttcgccaggctccaggaaaaggtctggagtgggtatcagctattggtactg<br>gtggtggcacatactatgcagactccgtgaagggccgattcaccatctccagggacaatgccaagaactccttgtatct<br>tcaaatgaacagcctgagagccgaggacaccgccatgtattactgtgcgcgcggtactggttacgacggtgatcagtg<br>gggtcaaggtactctggtgaccgtctcctcacaccatcaccatcaccatggcgcatacccgtacgacgttccggactac<br>gcttcttag (SEQ ID NO: 143) | | |

In an embodiment in which the antigen-binding protein is a full length antibody, the heavy and light chains of an antibody of the disclosure may be full-length (e.g., an antibody can include at least one, and preferably two, complete heavy chains, and at least one, and preferably two, complete light chains) or may include an antigen-binding portion (a Fab, F(ab')$_2$, Fv or a single chain Fv fragment ("scFv")). In other embodiments, the antibody heavy chain constant region is chosen from, e.g., IgG1, IgG2, IgG3, IgG4, IgM, IgA1, IgA2, IgD, and IgE. In some embodiments, the immunoglobulin isotype is selected from IgG1, IgG2, IgG3, and IgG4, more particularly, IgG1 (e.g., human IgG1). The choice of antibody type will depend on the immune effector function that the antibody is designed to elicit.

In constructing a recombinant immunoglobulin, appropriate amino acid sequences for constant regions of various immunoglobulin isotypes and methods for the production of a wide array of antibodies are known to those of skill in the art.

Nucleic acids that encode the antigen binding proteins identified herein can be used to engineer recombinant immune effector cells. Methods and vectors to generate genetically modified T-cells, for example, are known in the art (See Brentjens et al., Safety and persistence of adoptively transferred autologous CD19-targeted T cells in patients with relapsed or chemotherapy refractory B-cell leukemias in *Blood* 118(18):4817-4828, November 2011).

Other embodiments of the disclosure include cells and expression vectors comprising nucleic acids encoding the antigen-binding proteins or antigen-binding fragments thereof of the disclosure. The cells may be recombinant immune effector cells, such as T-cells genetically modified to express a chimeric antigen receptor comprising an antigen binding region in accordance with the present disclosure. Cells which have been engineered to produce antibodies in accordance with the disclosure are also encompassed by the disclosure.

Further, the disclosure comprises a method of producing an antibody or antibody fragment of the disclosure comprising: (a) culturing the recombinant cell comprising a nucleic acid encoding an antibody or antibody fragment of the disclosure in culture medium under conditions wherein the nucleic acid sequence is expressed, thereby producing polypeptides comprising the light and heavy chain variable regions; and (b) recovering the polypeptides from the host cell or culture medium.

Some embodiments of the antigen-binding protein of the disclosure encompass antagonistic anti-PD1 antibodies as well as anti-PD1 antibodies that function as agonists of PD1. While some anti-PD1 antibodies are antagonists, that is, they block binding of PD1 by its ligand, others are agonists, antibodies that have the effect of enhancing the immunosuppressive signal of PD-1, making them useful in the treatment of autoimmunity, for example. Antibodies of the disclosure that exhibit antagonist activity include clones 23 and 27 while clones 16, 18, 26, 31 and 40 appear to function as agonists.

The disclosure also comprises the use of an anti-PD-1 antibody or antibody fragment of the disclosure for the preparation of a medicament to increase immune response as well as the use of an anti-PD-1 antibody or antibody fragment of the disclosure for the preparation of a medicament to treat cancer.

Pharmaceutical compositions comprising the antigen binding protein, antibodies, nucleic acids, vectors or cells comprising the nucleic acids or antigen binding proteins of disclosed herein along with a pharmaceutically acceptable carrier are also encompassed by the disclosure.

The disclosure also comprises the use of an anti-PD-1 antibody or antibody fragment of the disclosure as a vaccine adjuvant.

In another aspect, the disclosure relates to an immunoconjugate comprising a first component which is an antigen-binding protein, antibody or antigen-binding fragment thereof as disclosed herein. The immunoconjugate comprises a second component that is a cytotoxin, a detectable label, a radioisotope, a therapeutic agent, a binding protein or a molecule having a second amino acid sequence. Where the second component is a binding protein or second antibody, the binding protein or second antibody has binding specificity for a target that is different from the HLA-peptide complex for which the first is specific.

The disclosure also relates to methods for treatment of a subject having a PD-1 associated disease, comprising administering to the subject a therapeutically effective amount of an antigen binding protein, antibody or antigen binding fragment thereof, a chimeric antigen receptor (CAR), a nucleic acid encoding the antigen binding protein or a cell comprising the nucleic acids or proteins as disclosed herein.

Those skilled in the art will recognize that several embodiments are possible within the scope and spirit of this invention. The invention will now be described in greater detail by reference to the following non-limiting examples. The following examples further illustrate the invention but, of course, should not be construed as in any limiting its scope.

EXAMPLES

Example 1

To test the ability of the scFvs to inhibit PD-1 ligation, scFv-Fc domain (scFv-Fc) fusion proteins were generated, where the scFvs were linked to a murine Fc (mouse IgG1a) domain. The scFv-Fc clones were then analyzed for the ability to bind PD-1 by coating an ELISA plate with human PD-1 monomer. Binding of the scFvs to PD-1 was quantified using a HRP-conjugated anti-mouse IgG1 Fc secondary antibody. All seven antibodies showed binding activity with respect to the PD1 monomer in a dose dependent manner (FIG. 1). ET901 ScFv-Fc (mouse IgG1 Fc) served as the negative control. Binding affinity of the scFv-Fc clones was ranked where clone 31 bound weakly and clones 26 and 27 bound the most strongly (31<23<40<18<16=27<26).

Example 2

Figure 2A:
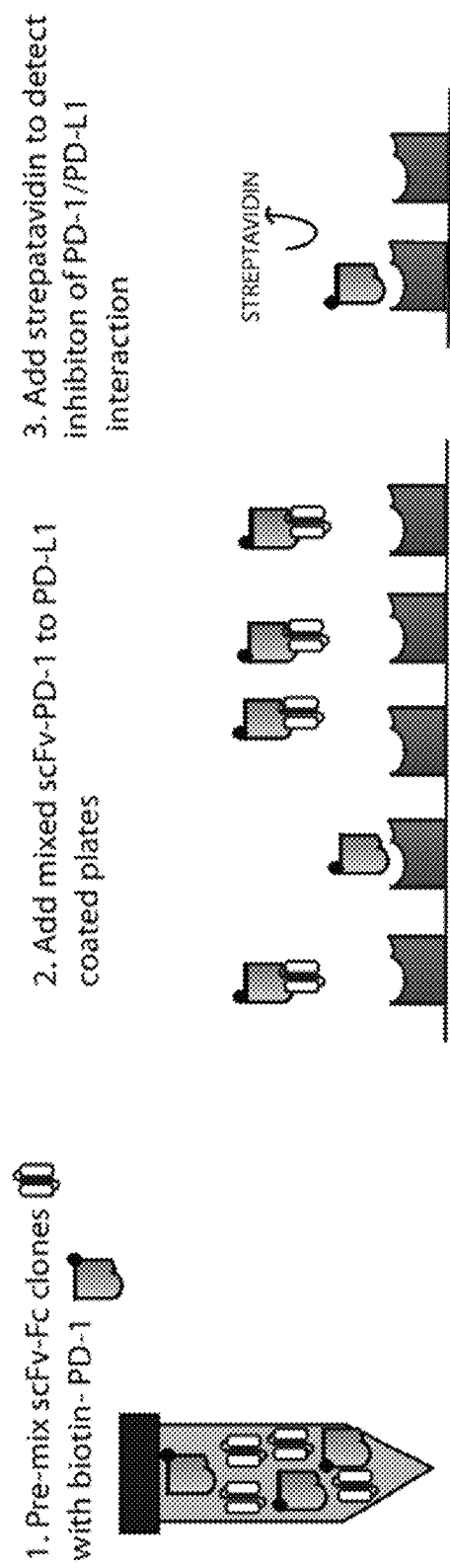
FIGS. 2A and B show disruption of the interaction of PD-1 with its ligand, PD-L1. A. is a schematic of the competitive binding assay used to measure the ability of the scFv-Fc to disrupt the PD-1/PD-L1 interaction. (1) biotinylated PD-1-Fc was mixed with serially diluted ET901 ScFv-Fc (negative control) or anti-PD1 ScFv-Fcs; and (2) then added into a PD-L1-Fc coated plate. In step (3) PD-1-Fc binding towards coated PD-L1 was visualized via HRP-conjugated streptavidin. B. In order to compare the competitive binding assay results, points where the concentration of the scFv was 1.7-5.25 ug/ml are circled. Clones 40 and 23 had the weakest ability to disrupt the interaction and clone 26 had the strongest (26>27=16>18>31>23=40).
Figure 2B:
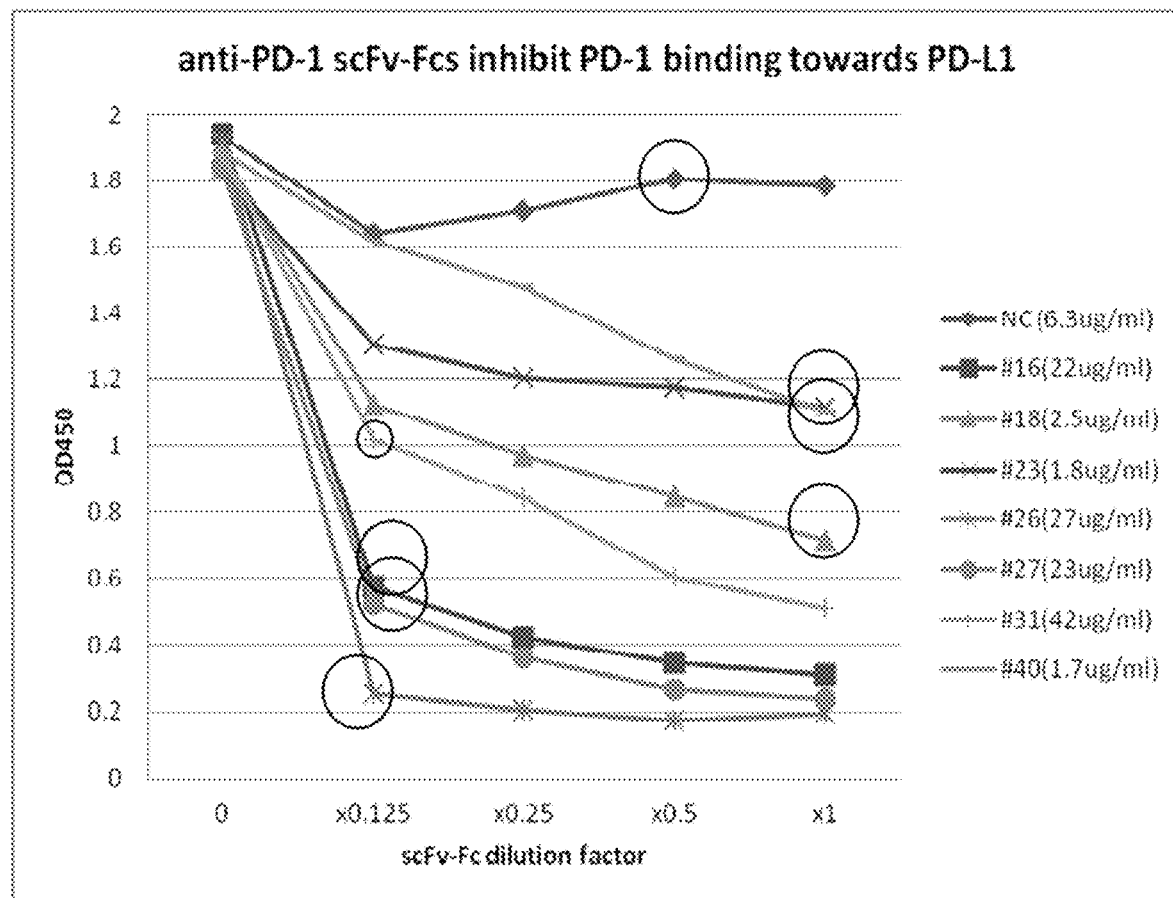

To test the ability of the scFv-Fc to inhibit PD-1 interacting with PD-L1, a competitive ligand-binding assay as shown schematically in FIG. 2A was performed. In this assay, PD-L1-Fc was coated onto ELISA plates. Biotinylated-PD1-Fc was mixed with serially diluted ET901 ScFv-Fc (negative control) or anti-PD1 ScFv-Fcs and then added into the PD-L1-Fc coated plate. PD-1-Fc binding to PD-L1 coated on the plates was visualized via HRP-conjugated streptavidin (FIG. 2B). When comparing similar concentrations of scFv-Fc (circled), the ability to disrupt the PD-1-PDL1 interaction was ranked where clones 40 and 23 had the weakest and clone 26 had the strongest ability to do so (26>27=16>18>31>23=40, FIG. 2B).

Example 3

Figure 3:
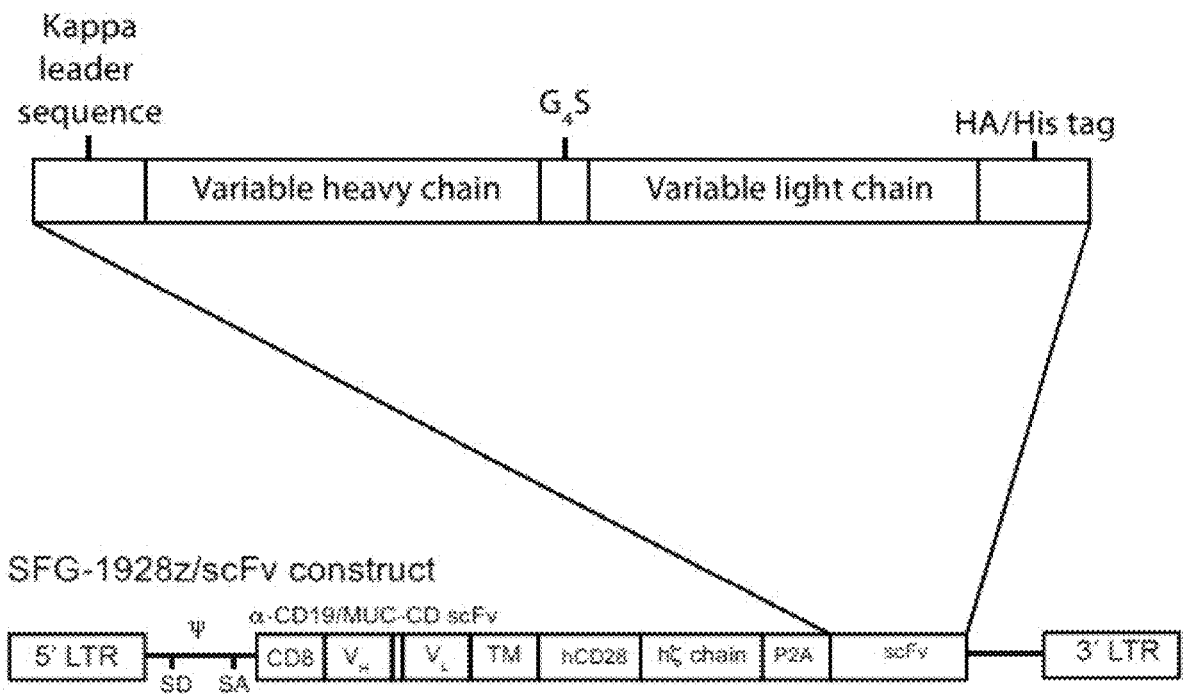
FIG. 3 is a schematic of the construct used. A secreteable scFv was designed to include a murine kappa leader sequence to allow exportation of the scFv from the cell. A serine glycine linker ($G_4S$) was used to link the variable heavy chain and variable light chain. A HIS/HA tag was included to allow detection of the scFv. The schematic of SFG-1928z/scFv retroviral construct depicting the 5' and 3' long terminal repeats (LTR), splice donor (SD), splice acceptor (SA), packaging element ($\psi$), CD8 leader sequence (CD8), variable heavy (VH) and variable light (VL) chains of the single chain variable fragment (scFv), transmembrane domain (TM), human CD28 signaling domain (hCD28), human zeta chain signaling domain (h$\zeta$ chain) and position of the anti-PD-1 scFv.

These clones were then investigated for their ability to regulate specific T cell function. We have previously generated tumor-targeted T cells, wherein T cells are retrovirally transduced to express a tumor-specific chimeric antigen receptor (CAR). We have previously demonstrated that expression of a CAR has redirected T cell function to target a given antigen (Brentjens, Santos et al. 2007). In our lab, we target B cell malignancies using a CAR specific for CD19, termed 1928z (Brentjens, Santos et al. 2007). We have previously demonstrated that CAR modified T cells have demonstrated significant anti-tumor activity in vitro and in vivo and in clinical studies (Brentjens, Latouche et al. 2003; Brentjens, Davila et al. 2013; Davila, Riviere et al. 2014). To determine whether the 7 scFv clones are agonistic (stimulate PD-1), antagonistic (block PD-1) or have no significant effect on PD-1, we generated a secretable scFv by including the murine Kappa leader sequence proximal to the anti-PD-1 scFv gene (FIG. 3). We then generated a bicistronic retroviral vector to induce expression of the 1928z CAR and secretion of an anti PD-1 scFv from transduced human peripheral blood T cells.

Example 4

Figure 4:
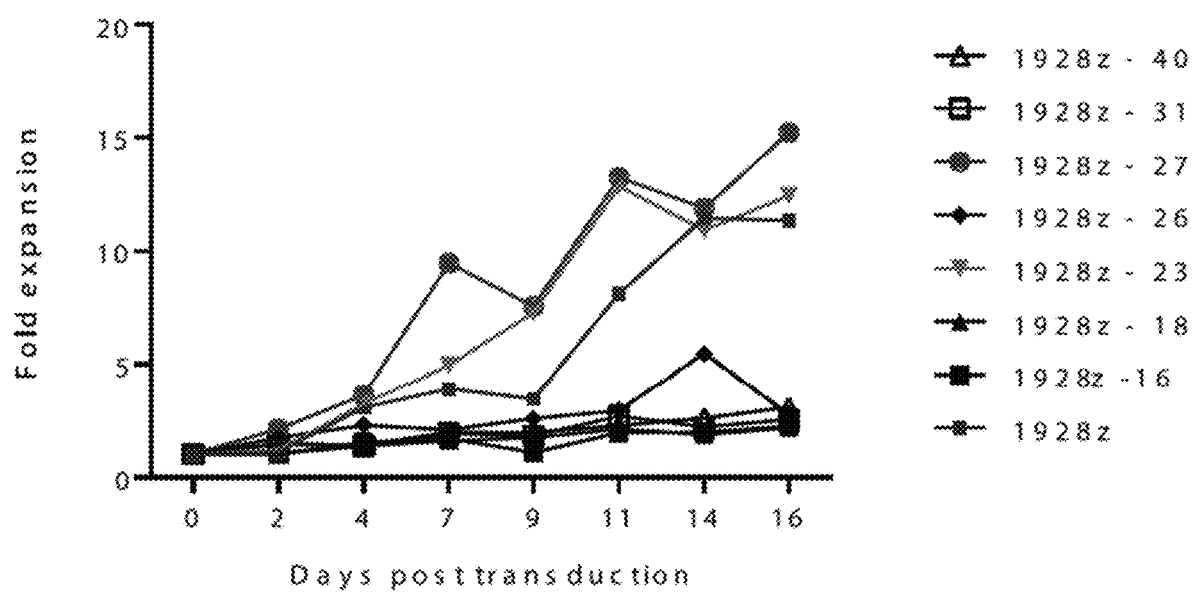
FIG. 4 Expansion of human peripheral blood T cells modified to express the 1928z CAR alone or with a PD-1 scFv. Transduced T cells were cultured in 50 IU/ml recombinant human IL-2 and expansion was monitored. T cells modified to express the CAR and secrete anti-PD-1 scFv clone 23 or 27 had expansion that was at least equivalent to T cells expressing the CAR alone. Cells modified to express the 1928z CAR and secrete anti-PD-1 scFv clones 16, 18, 26, 31 or 40 did not expand in vitro. Data shown is representative of two independent experiments.

Given the ability of PD-1 stimulation to inhibit T cell proliferation and function, we subsequently sought to characterize the effect of the anti-PD-1 scFvs on T cell proliferation. To achieve this, human T cells were isolated from peripheral blood of healthy donors and modified through retroviral transduction to express the CAR and secrete a PD-1-specific scFv, using methodology that has been previously described (Brentjens, Santos et al. 2007). Following transduction, modified T cells were monitored for expansion in vitro (FIG. 4). Expansion of T cells expressing the 1928z CAR and secreting PD-1 specific scFv clones 23 and 27 expanded as well as T cells modified to express the 1928z CAR alone. Cells modified to express the CAR and secrete PD-1-specific scFv clones 16, 18, 26, 31 or 40 did not proliferate, suggesting that these PD-1-specific scFv clones were agonistic, potentially stimulating PD-1 and in turn, resulting in decreased T cell proliferation.

Example 5

Figure 5:
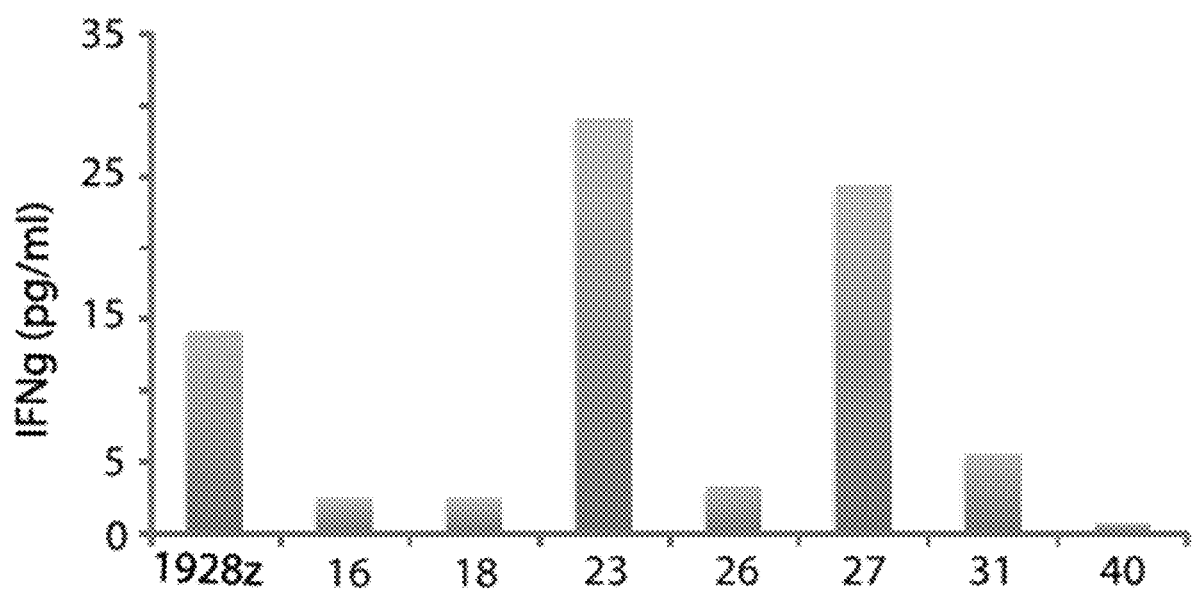
FIG. 5 INF-γ secretion (pg/ml) from tumor targeted T cells that secrete an anti-PD-1 scFv. T cells expressing the CAR or CAR and secreting an anti-PD-1 scFv were cocultured with CD19+ Raji tumor cells. Supernatants were analysed with Luminex technology to detect the levels of cytokines secreted from the T cells. T cells modified to express the 1928z CAR and secrete anti-PD-1scFv clones 23 and 27 had increased secretion of IFN-γ compared to cells modified to express the CAR alone. Cells modified to express the 1928z CAR and secrete anti-PD-1 scFv clones 16, 18, 2, 31 or 40 secreted less IFN-γ compared to cells modified with the CAR alone.

In addition to expansion studies, we co-cultured T cells (expressing the CAR or CAR and secreting a PD-1-specific scFv) with the CD19+ Burket's lymphoma tumor cell line, Raji, and determined the level of cytokine secretion from the T cells. As shown in FIG. 5, T cells modified to express the 1928z CAR and secrete the PD-1-specific scFv clones 23 or 27 had increased secretion of IFN-γ compared to cells modified to express the CAR alone, suggesting that these scFv clones were antagonistic to PD-1 signaling. Cells modified to express the 1928z CAR and secrete the PD-1-specific scFv clones 16, 18, 2, 31 or 40 secreted less IFN-γ compared to cells modified with the CAR alone, suggesting that these scFvs were agonistic to PD-1 and inhibited T cell function.

Example 6

Figure 6:
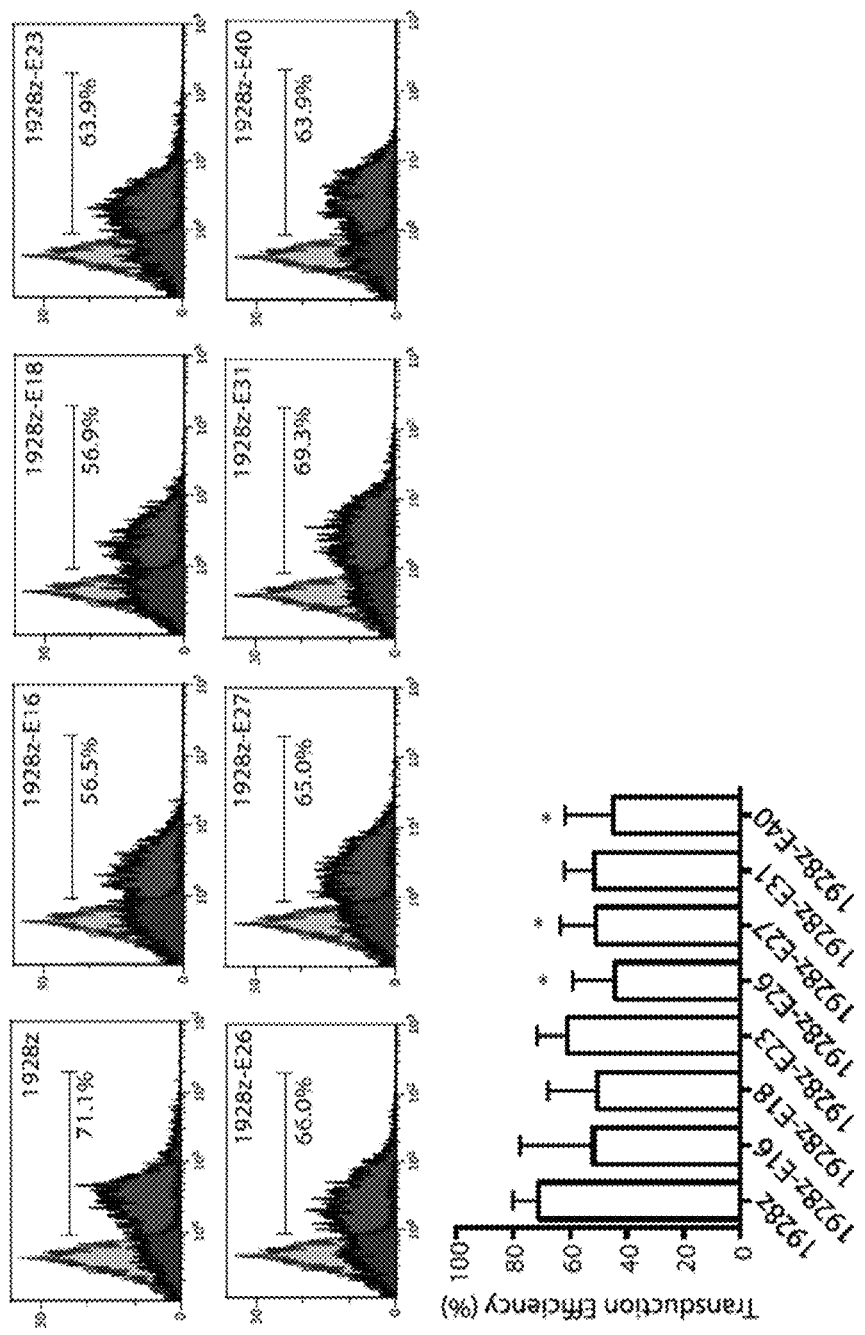
FIG. 6 shows the results of transduction of human T cells with 1928z CAR and Eureka anti-PD-1 scFvs. (Upper panel) Following transduction, human T cells were assessed by flow cytometry to detect CAR expression using antibody specific for the 1928z CAR (19E3). Transduction efficiency was greater than 55% for all contructs tested and reproducible. (Lower panel) Constructs containing Eureka anti-PD-1 scFv clones 26, 27 and 40 had significantly lower transductions efficiency, *$p<0.05$. Transduction efficiency from 4 independent experiments, data shown is average+/−SEM.
Figure 7:
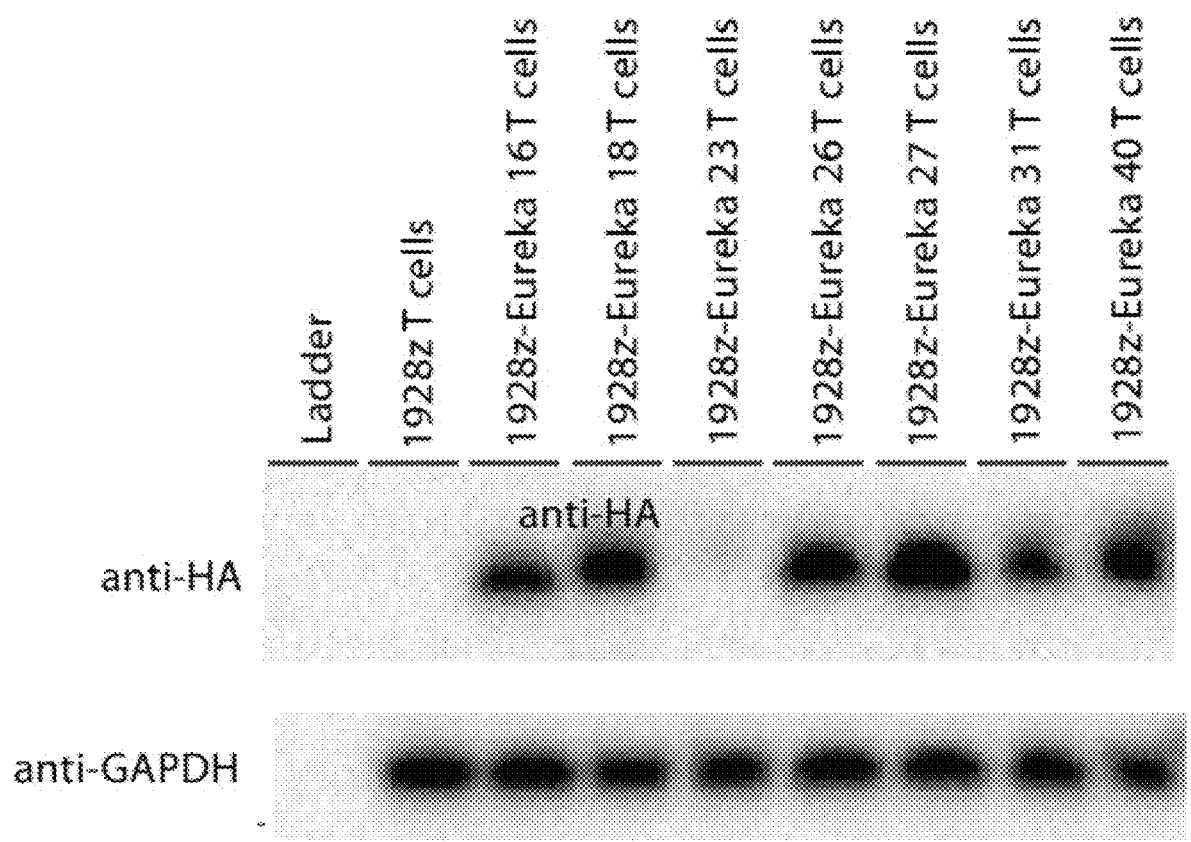
FIG. 7 shows the effect of the presence of anti-PD-1 scFv in T cells modified to express the 1928z CAR and Eureka anti-PD-1 scFv. Human T cells transduced to express the CAR and the Eureka anti-PD-1 scFvs were incubated with golgi inhibitors for 4 hours prior to preparation of western blot lysates. Western blot analysis was used to detect anti-PD-1 scFv by probing the membrane with anti-HA antibody. Membranes were probed with anti-GAPDH antibody as loading control.
Figure 8:
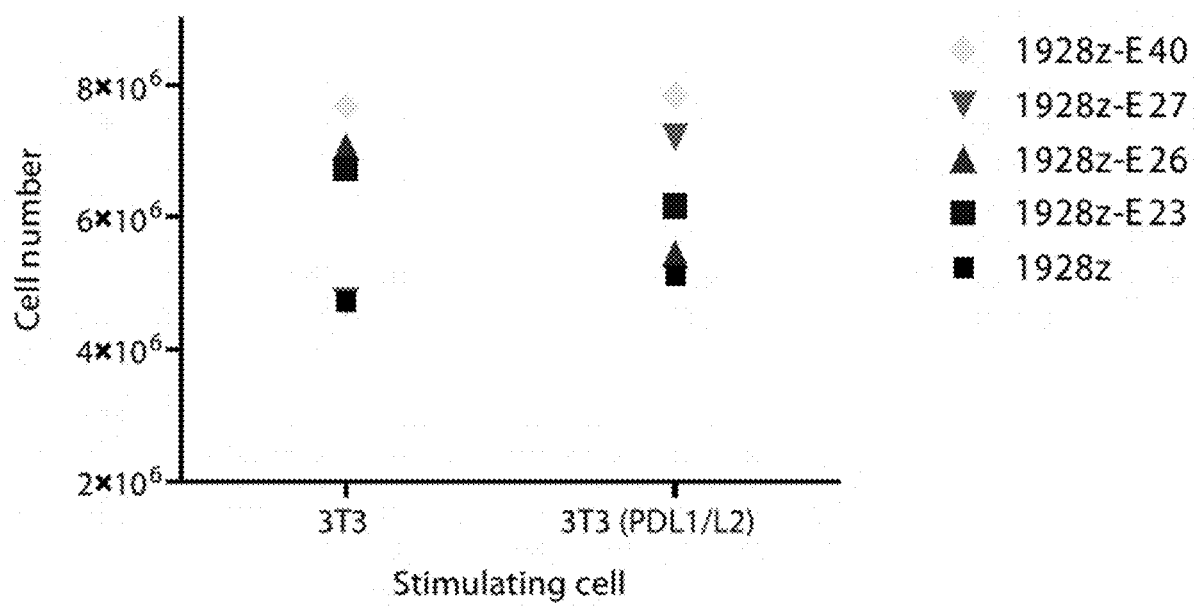
FIG. 8 shows the expansion of human T cells modified to express the 1928z CAR and anti-PD-1 scFv in the presence/absence of PD-L1/L2. Human T cells modified to express the CAR and secrete anti-PD-1 scFv clones 23, 26, 27, and 40 were placed on artificial antigen presenting cells (aAPCs, murine 3T3 fibroblasts) expressing human PD-1 L1/L2 or not. After 24 hours incubation with aAPCs, CD3/CD28 activating beads were added to the cells to stimulate proliferation (1:2 bead:T cell ratio). After 3 days, T cells were enumerated using trypan blue exclusion. T cells modified to express the 1928zCAR and anti-PD-1 scFv clone 26 and 23 had decreased proliferation on aAPCs expressing PD-L1/L2 to aAPCs not expressing inhibitory ligands. In contrast, T cells modified to express the 1928zCAR and anti-PD-1 scFv clone 27 had increased expansion on aAPCs expressing PD-L1/L2. Data shown is representative of one experiment.

Human T cells modified to express the 1928 CAR and a PD-1 blocking scFv were analyzed by flow cytometry. Following verification of expression of the CAR (FIG. 6) the presence of the scFvs was determined using western blot (using an antibody specific for an HA tag incorporated in the scFv design) on lysates prepared from human T cells treated with golgi inhibitors to allow detection in the cell lysates. Human T cells modified to express 1928z CAR and clone 23 had significantly less scFv protein compared to the other clones (FIG. 7). These cells were then placed on 3T3 murine fibroblasts (artificial antigen presenting cells, a APCs) that do or do not express PD-1 ligands, PD-L1/L2. Following 24 hour culture with the aAPCs, CD3/D28 beads were added to the cultures to activate the human T cells. Three days following culture of human T cells, aAPCs and beads the human T cells were enumerated to determine if the presence of PD-1 ligands inhibited the bead-driven expansion of human T cells, or if the anti-PD-1 scFvs prevented the PD-1 ligand mediated inhibition of T cell expansion. T cells modified to express the 1928z CAR and anti-PD-1 scFv clone 26 and 23 have decreased proliferation on aAPCs expressing PD-L1/L2 to aAPCs not expressing inhibitory ligands (FIG. 8). In contrast, T cells modified to express the 1928z CAR and anti-PD-1 scFv clone 27 have increased expansion on aAPCs expressing PD-L1/L2.

Example 7

Figure 10:
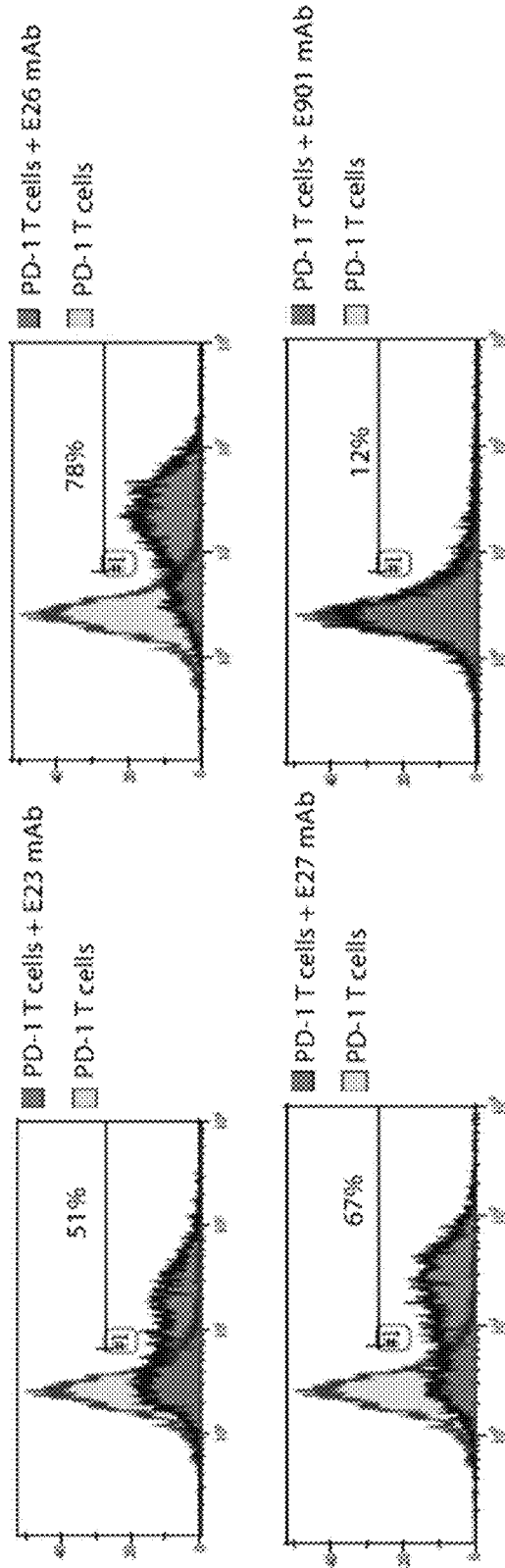
FIG. 10 shows that monoclonal antibodies generated from the anti-PD-1 specific scFvs bind to PD-1 on human T cells. Human monoclonal antibodies from the PD-1 specific scFvs were generated and incubated with human T cells modified to overexpress human PD-1 (1 µg/ml). Flow cytometry was used to detect bound antibody using a goat anti-human Ig FITC conjugated antibody. Clones 23, 26 and 27 monoclonal antibodies bound P-1 human T cells at 51%, 78% and 67% respectively. Control antibody (clone 901) did not bind human PD-1 on T cells. Data shown is representative of one experiment.

Using recombinant technology know in the art, recombinant human monoclonal antibodies were generated from the PD-1 specific scFvs, that is, fully human Ig molecules were made with the same variable heavy and light chains found in the corresponding scFvs (see Tables 1-14 above and FIG. 9). The binding of these monoclonal antibodies to PD-1 was demonstrated using flow cytometry (see FIG. 10).

Human T cells were modified to overexpress human PD-1, then incubated with 1 μg/ml of antibody. Clone 27 mAb bound to the PD-1 T cells the most, followed by clone 26 and then clone 23 (FIG. 9). The control monoclonal antibody, 901, did not bind to the PD-1 T cells. T cells incubated with these antibodies were then placed on artificial antigen presenting cells (aAPCs) with beads to determine the impact of PD-1 ligands on the expansion of the T cells and the ability of the monoclonal antibodies to prevent this interaction. 19z1 T cells incubated with anti-PD-1 clone 27 monoclonal antibody expanded on PD-L1/L2 aAPCs to a greater extent.

Example 8

Figure 11:
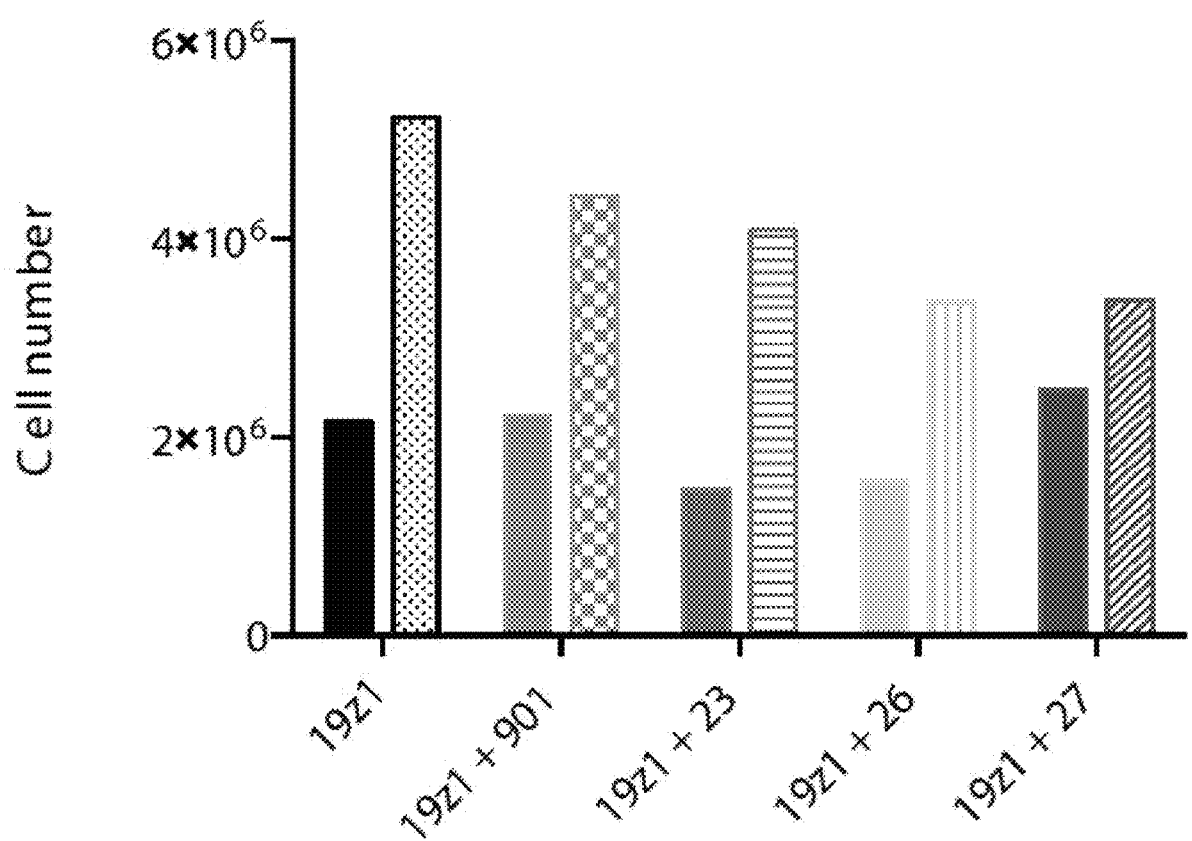
FIG. 11 shows that T cells modified to express a first generation CAR incubated on aAPCs expressing PD-L1/L2 expand when anti-PD-1 clone 27 monoclonal antibody is present. Human T cells modified to express the first generation CD19-specific CAR (19z1) were incubated with anti-PD-1 monoclonal antibodies for 24 hours then placed on aAPCs expressing PD-L1/L2 or not. After 24 hours stimulation with aAPCs, the cells were then stimulated with CD3/CD28 beads. After three days, the cells were enumerated. 19z1 T cells incubated with no monoclonal antibody (stippled bar), control antibody, 901 (checkered bar) and clones 23 (horizontal striped bar) and 26 (vertical striped bar) monoclonal antibody expanded much less on aAPCs expressing PD-1 ligands (corresponding open bars) compared to aAPCs with no inhibitory ligand. However, 19z1 T cells incubated with anti-PD-1 clone 27 monoclonal antibody (diagonally striped bar) expanded on PD-L1/L2 aAPCs to a greater extent. Data shown is representative of one experiment.

T cells modified to express a first generation CAR incubated on aAPCs expressing PD-L1/L2 expand when anti-PD-1 clone 27 monoclonal antibody is present. Human T cells modified to express the first generation CD19-specific CAR (19z1) were incubated with anti-PD-1 monoclonal antibodies for 24 hours then placed on aAPCs expressing PD-L1/L2 or not. After 24 hours stimulation with aAPCs, the cells were then stimulated with CD3/CD28 beads. After three days, the cells were enumerated. 19z1 T cells incubated with no monoclonal antibody, control antibody (901) and clones 23 and 26 monoclonal antibody expanded much less on aAPCs expressing PD-1 ligands (FIG. 11 open bars) compared to aAPCs with no inhibitory ligands (FIG. 11 closed bars). However, 19z1 T cells incubated with anti-PD-1 clone 27 monoclonal antibody expanded on PD-L1/L2 aAPCs to a greater extent. Data shown is representative of one experiment.

Example 9

Figure 12A:
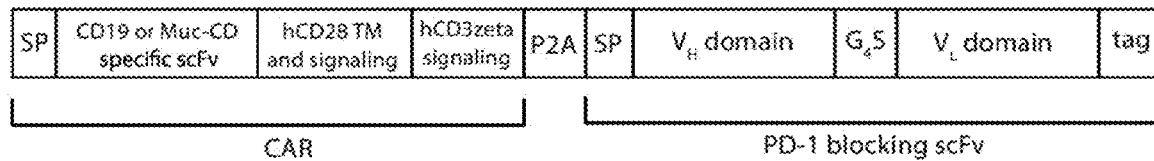
FIGS. 12A-12D show the generation of CAR T cells further modified to secrete PD-1 blocking scFv, E27. A. Bicistronic retroviral constructs were generated encoding a CD19-specific CAR (termed 1928z) or an ovarian tumor antigen specific CAR (termed 4H1128z) and the PD-1 blocking scFv, E27. The E27 was preceded by a signal peptide, mouse IgK, to allow secretion of the scFv. A HA/His tag was also included to detect the scFv once secreted from the T cells. B. Human peripheral blood T cells were transduced with the retroviral constructs encoding the CAR, 1928z, or the CAR and the E27 PD-1 blocking scFv, 1928z-E27. Following transduction, flow cytometry was used to detect expression of the CAR, using an antibody that specifically binds the CD19-targeted CAR, termed 19E3. C. Western blot analysis of supernatant from transduced human T cells was utilized to detect the PD-1 blocking scFv with an anti-HA antibody. We also investigated scFv secretion from T cells modified to express the CAR and a control scFv, B6, which was detected using an anti-c-myc tag antibody. D. A standard $^{51}$Cr release assay against two CD19$^+$ tumor targets was performed to ensure that secretion of an scFv did not interrupt the ability of the CAR to redirect T cells cytolytic capacity. CAR T cells expressing either the CAR alone (1928z or 4H1128z control CAR), the CAR and the E27 scFv (1928z-E27 or 4H1128z-E27), or the CAR and a control scFv (1928z-B6H12.2 or 4H1128z-B6H12.2) were incubated with $^{51}$Cr labeled tumor cells (Raji or Nalm6) for 4 hrs. T cells expressing the CD19 specific CAR were able to lyse the tumor targets at equivalent levels, and the ovarian-targeted CAR T cells were unable to lyse Raji or Nalm6. Therefore, we conclude that secretion of the scFv did not interrupt the ability of the CAR to redirect T cell lytic capacity.
Figure 12B:
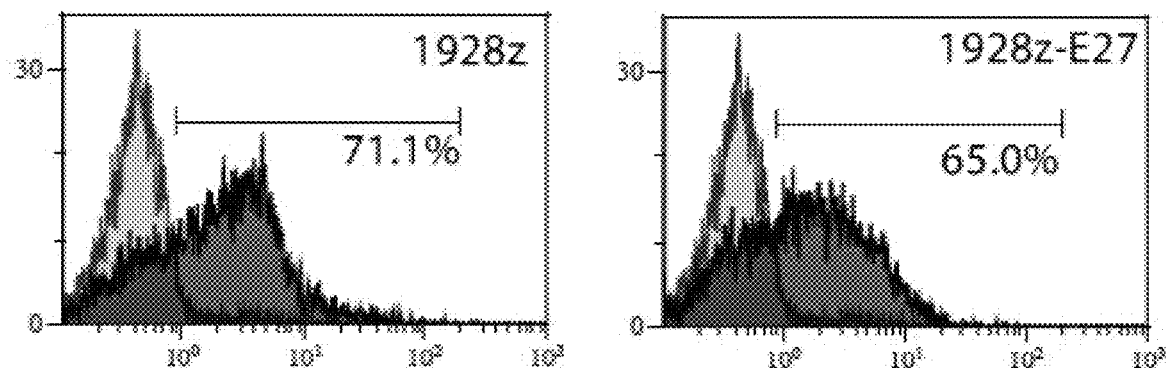
Figure 12C:
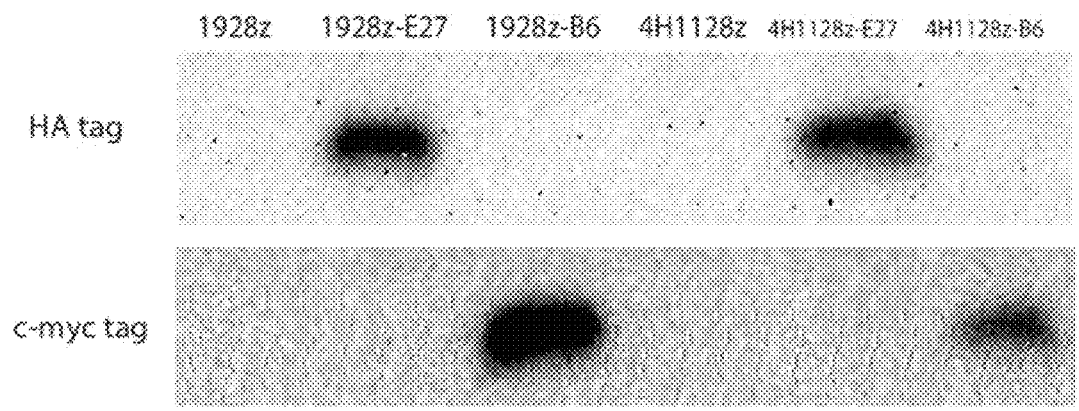
Figure 12D:
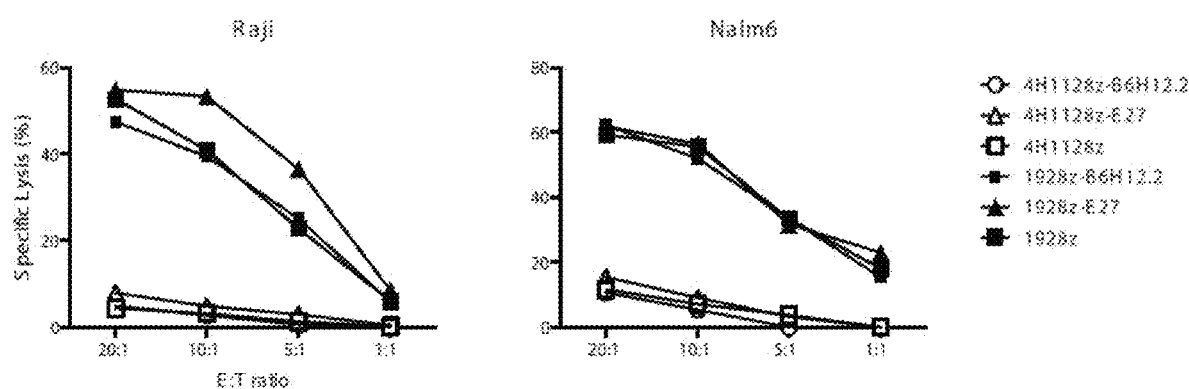

Generation of CAR T cells further modified to secrete PD-1 blocking scFv, E27. Bicistronic retroviral constructs were generated encoding a CD19-specific CAR (termed 1928z) or an ovarian tumor antigen specific CAR (termed 4H1128z) and the PD-1 blocking scFv, E27 (FIG. 12A). The E27 was preceded by a signal peptide, mouse IgK, to allow secretion of the scFv. A HA/His tag was also included to detect the scFv once secreted from the T cells. Human peripheral blood T cells were transduced with the retroviral constructs encoding the CAR, 1928z, or the CAR and the E27 PD-1 blocking scFv, 1928z-E27. Following transduction, flow cytometry was used to detect expression of the CAR, using an antibody that specifically binds the CD19-targeted CAR, termed 19E3 (FIG. 12 B). Western blot analysis of supernatant from transduced human T cells was utilized to detect the PD-1 blocking scFv with an anti-HA antibody (FIG. 12C). We also investigated scFv secretion from T cells modified to express the CAR and a control scFv, B6, which was detected using an anti-c-myc tag antibody. A standard $^{51}$Cr release assay against two CD19$^+$ tumor targets was performed to ensure that secretion of an scFv did not interrupt the ability of the CAR to redirect T cells cytolytic capacity. CAR T cells expressing either the CAR alone (1928z or 4H1128z control CAR), the CAR and the E27 scFv (1928z-E27 or 4H1128z-E27), or the CAR and a control scFv (1928z-B6H12.2 or 4H1128z-B6H12.2) were incubated with $^{51}$Cr labeled tumor cells (Raji or Nalm6) for 4 hrs. T cells expressing the CD19 specific CAR were able to lyse the tumor targets at equivalent levels, and the ovarian-targeted CAR T cells were unable to lyse Raji or Nalm6 (FIG. 12D). Therefore, we conclude that secretion of the scFv did not interrupt the ability of the CAR to redirect T cell lytic capacity.

Example 10

Figure 13A:
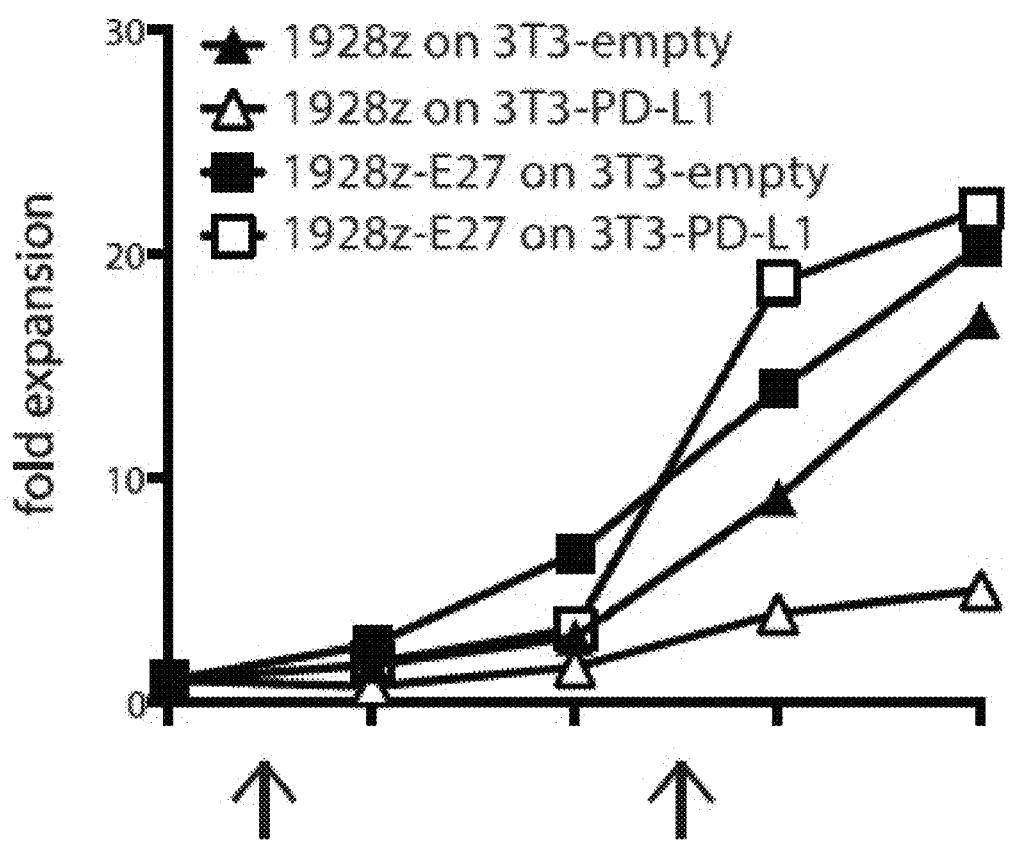
FIGS. 13A-13D show that T cells modified to express the CAR and secrete a PD-1 blocking scFv resist inhibition from PD-L1-PD-1 interactions, in vitro. A. T cells expressing the CAR alone (1928z), or the CAR and the PD-1 blocking scFv (1928z-E27) were cultured on 3T3 cells empty cells or 3T3 cells modified to express human PD-L1. Following 24 hours on the 3T3 feeder cells, cells were stimulated with CD3/CD28 beads added to the cultures at a 1:3 bead: T cell ratio. Expansion of T cells was determined with trypan blue enumeration and fresh beads were added twice to the cultures (indicated by the arrows). 1928z T cells expanded on 3T3 empty feeder cells, however did not expand on the 3T3-PD-L1 feeder cells. In contrast, 1928z-E27 T cells expanded on both the 3T3 Empty and 3T3-PD-L1 feeder cells, indicating a resistance to PD-L1-PD-1 mediated suppression. B. T cells incubated on 3T3 empty or 3T3-PD-L1 cells as shown in FIG. 13A were analyzed by flow cytometry to detect expression on inhibitory receptors, PD-1, 2B4 and LAG3. 1928z cells expressed increased levels of PD-1 than 1928z-E27 cells (not shown). When gated on PD-1$^+$ cells, analysis of 2B4 and LAG3 revealed that 1928z cells had a higher proportion of PD-1$^+$, 2B4$^+$ and LAG3$^+$ cells compared to 1928z-E27 cells. C. Transduced T cells were cultured with Raji-PDL1 or Nalm6-PDL1 tumor cells at varying effector to target (E:T) ratios (1:1, 1:3, 1:5) for 72 hours. Flow cytometry following staining with anti-CD3 and anti-CD19 antibodies and enumeration beads were used to monitor lysis of tumor targets and expansion of T cells over time. 1928z-E27 cells (upper curves) continued to expand to greater levels compared to 1928z T cells (lower curves) when cultured with PDL1$^+$ tumor cells. D. Transduced T cells were stimulated with Nalm6-PDL1 tumor cells as shown in FIG. 3C were re-stimulated with Nalm6-PDL1 tumor cells at the 1:5 T E:T ratio. After 48 hours co-culture flow cytometry was used to determine lysis of tumor targets. 1928z-E27 retained ability to lyse PD-L1 tumor targets upon re-stimulation compared to 1928z cells.
Figure 13B:
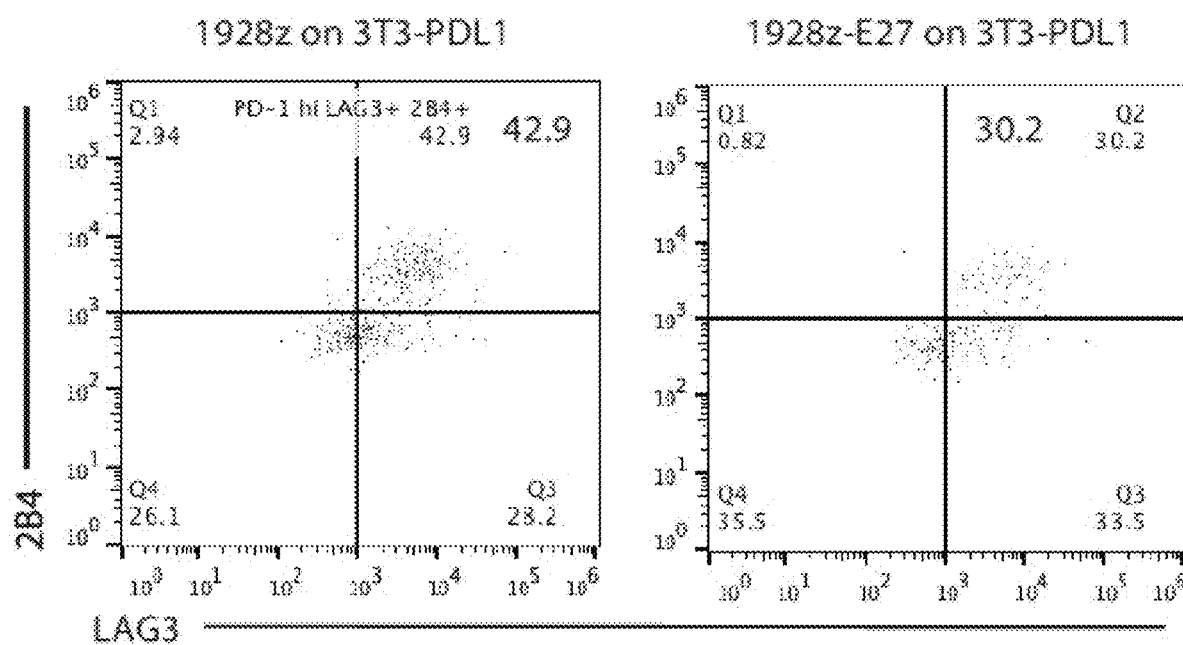
Figure 13C:
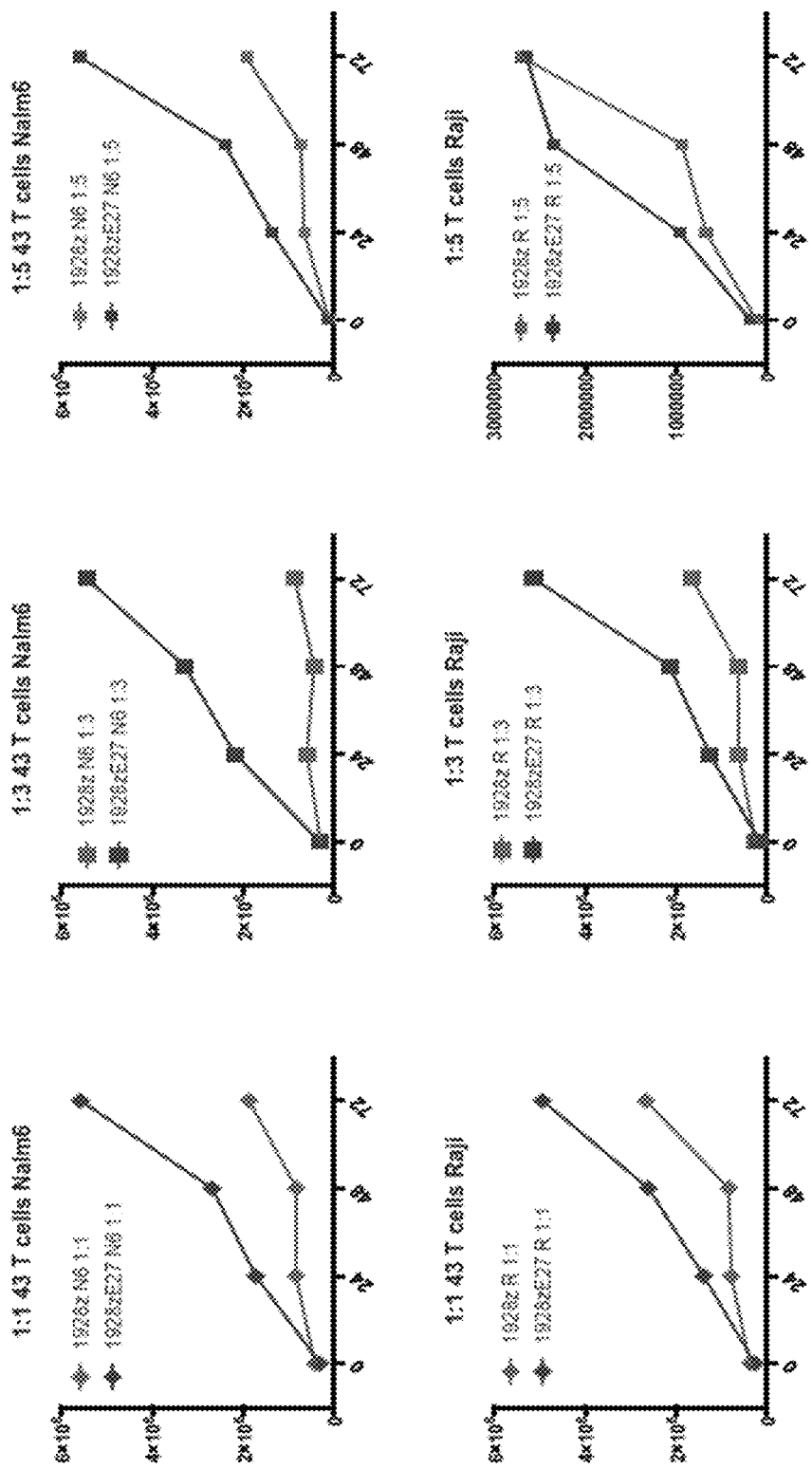
Figure 13D:
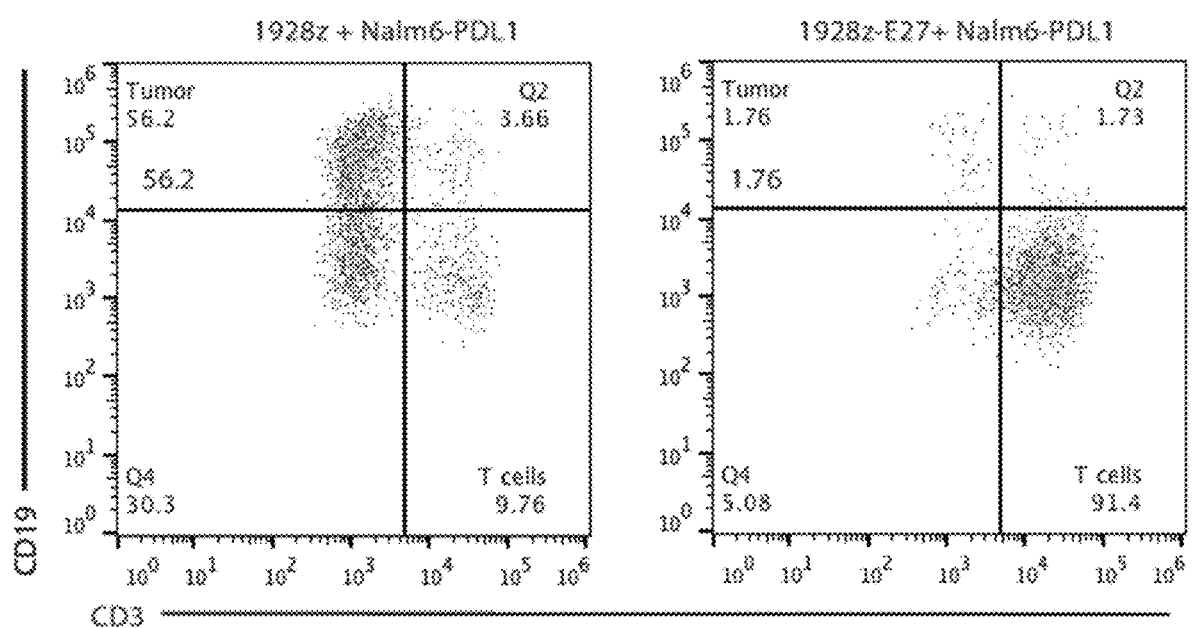

T cells modified to express the CAR and secrete a PD-1 blocking scFv resist inhibition from PD-L1-PD-1 interactions, in vitro. T cells expressing the CAR alone (1928z), or the CAR and the PD-1 blocking scFv (1928z-E27) were cultured on 3T3 cells empty cells or 3T3 cells modified to express human PD-L1. Following 24 hours on the 3T3 feeder cells, cells were stimulated with CD3/CD28 beads added to the cultures at a 1:3 bead: T cell ratio. Expansion of T cells was determined with trypan blue enumeration and fresh beads were added twice to the cultures (indicated by the arrows). 1928z T cells expanded on 3T3 empty feeder cells, however did not expand on the 3T3-PD-L1 feeder cells. In contrast, 1928z-E27 T cells expanded on both the 3T3 Empty and 3T3-PD-L1 feeder cells, indicating a resistance to PD-L1-PD-1 mediated suppression (FIG. 13A). T cells incubated on 3T3 empty or 3T3-PD-L1 cells as shown in FIG. 13A were analyzed by flow cytometry to detect expression on inhibitory receptors, PD-1, 2B4 and LAG3. 1928z cells expressed increased levels of PD-1 than 1928z-E27 cells (not shown). When gated on PD-1$^+$ cells, analysis of 2B4 and LAG3 revealed that 1928z cells had a higher proportion of PD-1$^+$, 2B4$^+$ and LAG3$^+$ cells compared to 1928z-E27 cells (FIG. 13B). Transduced T cells were cultured with Raji-PDL1 or Nalm6-PDL1 tumor cells at varying effector to target (E:T) ratios (1:1, 1:3, 1:5) for 72 hours. Flow cytometry following staining with anti-CD3 and anti-CD19 antibodies and enumeration beads were used to monitor lysis of tumor targets and expansion of T cells over time. 1928z-E27 cells continued to expand to greater levels compared to 1928z T cells when cultured with PDL1$^+$ tumor cells (FIG. 13C). Transduced T cells were stimulated with Nalm6-PDL1 tumor cells as shown in FIG. 3C were re-stimulated with Nalm6-PDL1 tumor cells at the 1:5 T E:T ratio. After 48 hours co-culture flow cytometry was used to determine lysis of tumor targets. 1928z-E27 retained ability to lyse PD-L1 tumor targets upon re-stimulation compared to 1928z cells (FIG. 13D).

Example 11

Figure 14:
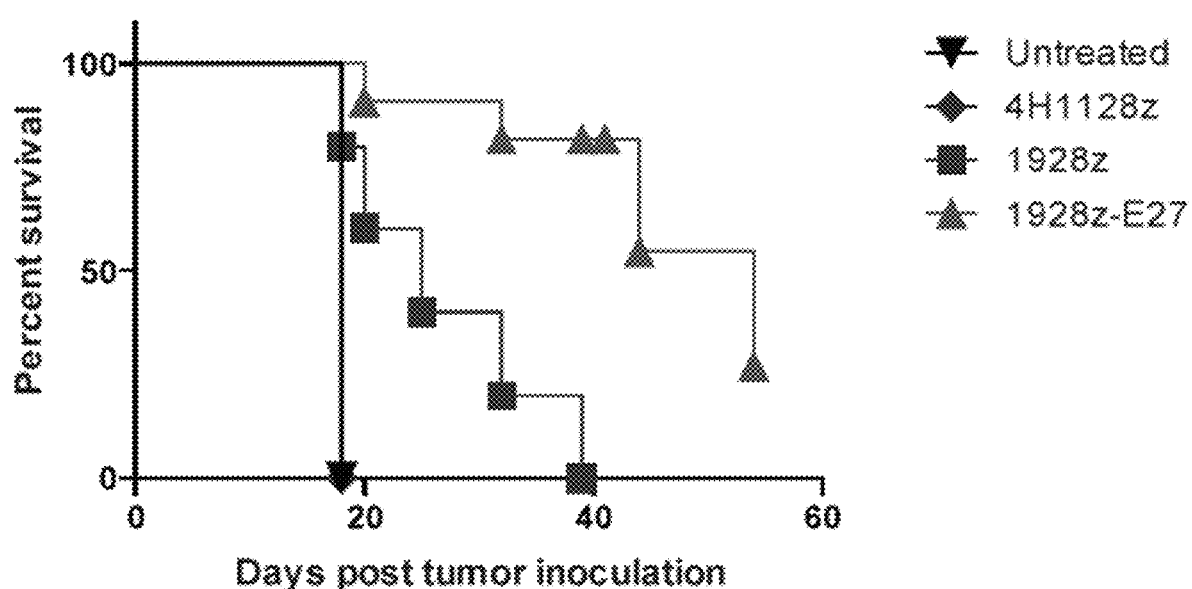
FIG. 14 shows in vivo anti-tumor efficacy of T cells modified to express the CAR and secrete the PD-1 blocking scFv. A. SCID-beige mice were inoculated with Raji-PD-L1 tumor cells via intravenous infusion on Day 0. On Day 1, mice were infused intravenously with 10$^6$ CAR+ T cells and survival was monitored clinically. Mice were euthanized upon development of hind limb paralysis.

In vivo anti-tumor efficacy of T cells modified to express the CAR and secrete the PD-1 blocking scFv is shown in FIG. 14. SCID-beige mice were inoculated with Raji-PD-L1 tumor cells via intravenous infusion on Day 0. On Day 1, mice were infused intravenously with 10$^6$ CAR+ T cells and survival was monitored clinically. Mice were euthanized upon development of hind limb paralysis.

Example 12

Figure 15A:
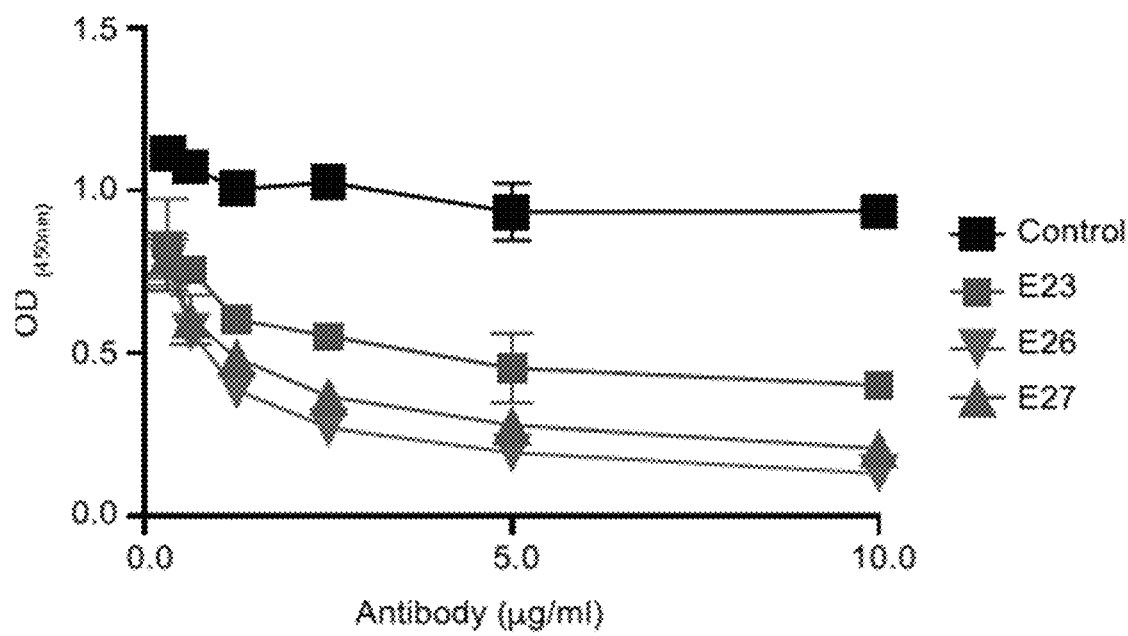
FIGS. 15A-15D relate to the selection of PD-1 blocking scFv, E27. A PD-1 blocking mAb candidates E27, E26 and E23 were used in a competitive binding assay to detect interruption of PD-1 binding to PD-L1 at varying concentrations, compared to a control mAb, targeted to a hapten not present in humans. E23, E26 and E27 mAbs all prevented PD-1 binding to PD-L1. B Schematic of design of PD-1 blocking scFv designed from the E23, E26 and E27 mAbs used in A, where the signal peptide was linked to the variable heavy sequence and a serine glycine linker and the variable light sequence. This HIS/HA tag was included for detection of the scFv. C Western blot on SN from 293Glv9 packaging cells transduced to express the secretable scFvs with the 1928z CAR, stained with anti-HA antibody. The E27 scFv was detected at the highest levels and therefore was used in the remainder of the publication. D Western blot on SN from PBMCs+4H1128z and PBMCs +4H1128z stained with anti-HA mAb.
Figure 15B:
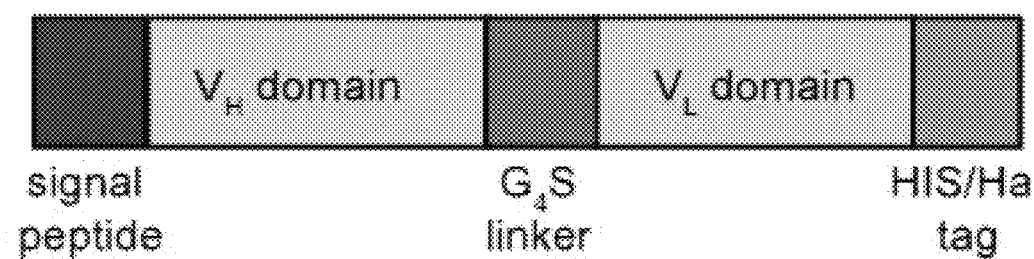
Figure 15C:
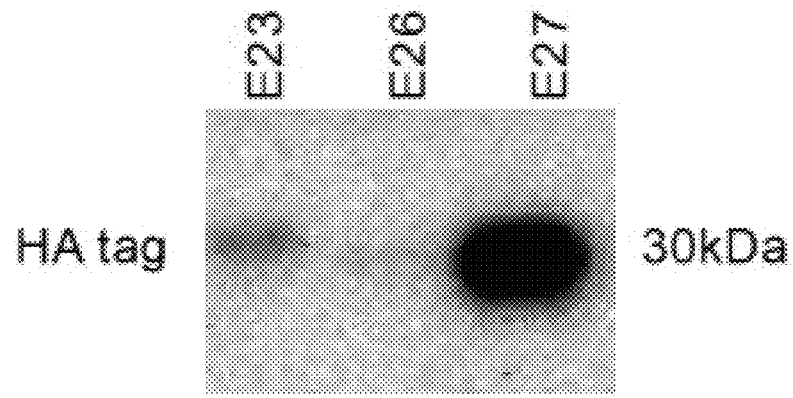
Figure 15D:
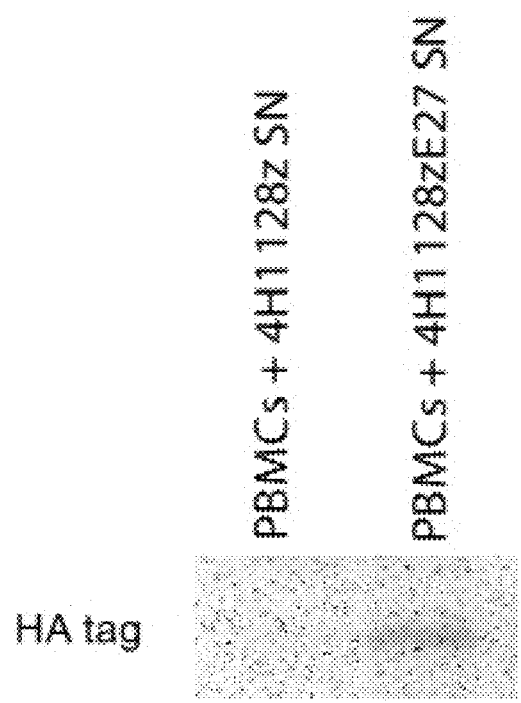

PD-1 blocking mAb candidates E27, E26 and E23 were used in a competitive binding assay to detect interruption of PD-1 binding to PD-L1 at varying concentrations, compared to a control mAb, targeted to a hapten not present in humans. E23, E26 and E27 mAbs all prevented PD-1 binding to PD-L1 (FIG. 15A). Western blot on SN from 293Glv9 packaging cells transduced to express the secretable scFvs with the 1928z CAR, stained with anti-HA antibody. The E27 scFv was detected at the highest levels and therefore was used in the remainder of the study (FIG. 15C).

Example 13

Figure 16A:
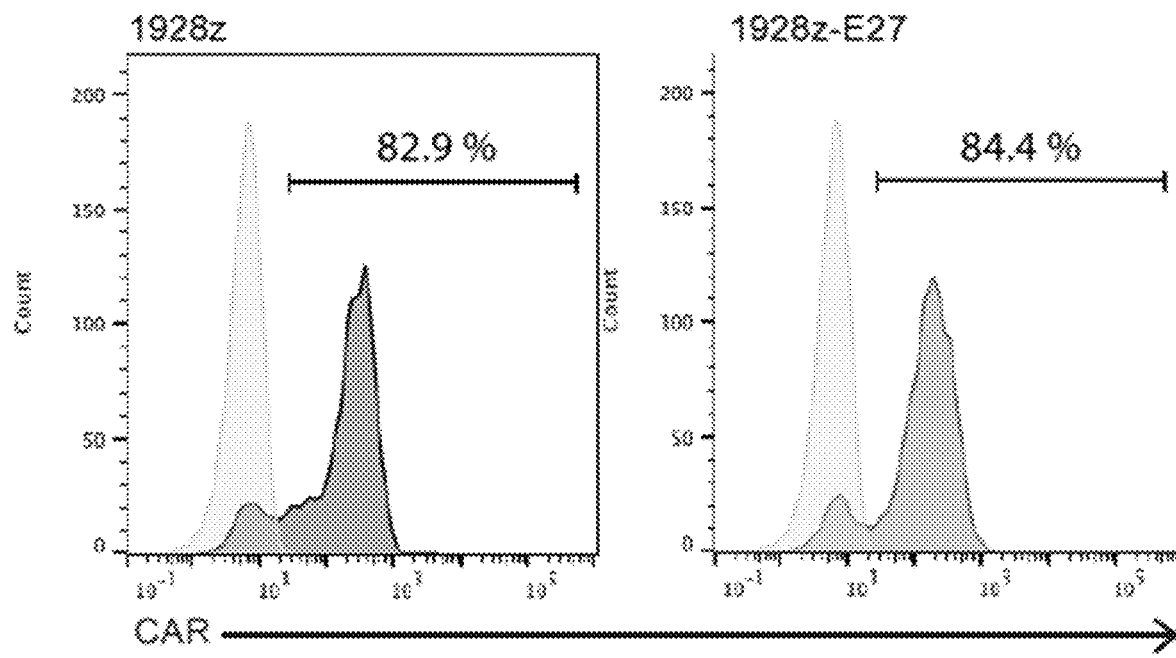
FIGS. 16A-16E show that T cells can be co-modified to express CAR and secrete PD-1 blocking scFv, E27. A Representative flow cytometry plot demonstrating equivalent CAR expression following transduction with the 1928z CAR alone (1928z) or the 1928z CAR and the E27 PD-1 blocking scFv (1928z-E27), following stainting with 19E3 mAb that specifically binds the 1928z CAR. B Western blot on SN from 1928z and 1928z-E27 T cells stained with anti-HA mAb, showing only a ~30 kDa protein in the 1928z-E27 cells, demonstrating that the E27 scFv is secreted from the 1928z-E27 transduced T cells and not those transduced with the CAR alone. C Representative flow cytometry demonstrating lower levels of PD-1 expression on 1928z-E27 T cells compared to 1928z T cells following transduction. D Expression of PD-1 was statistically significantly lower on 1928z-E27 T cells compared to 1928z T cells, data shown is mean+/−SEM from 4 independent experiments. E 4 hr $^{51}$Cr release assay demonstrating that lysis of Raji tumor cells was unaffected by secretion of the E27 scFv. 1928z and 1928z-E27 T cells lysed Raji tumor cells equivalently. Control 4H1128z-E27 T cells mediated no increase in lysis of Raji cells compared to 4H1128z T cells. Data shown is representative of two independent experiments.
Figure 16B:
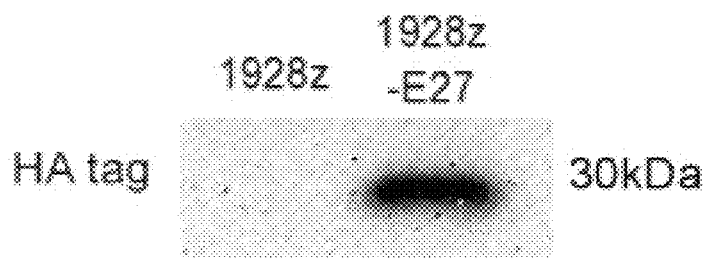
Figure 16C:
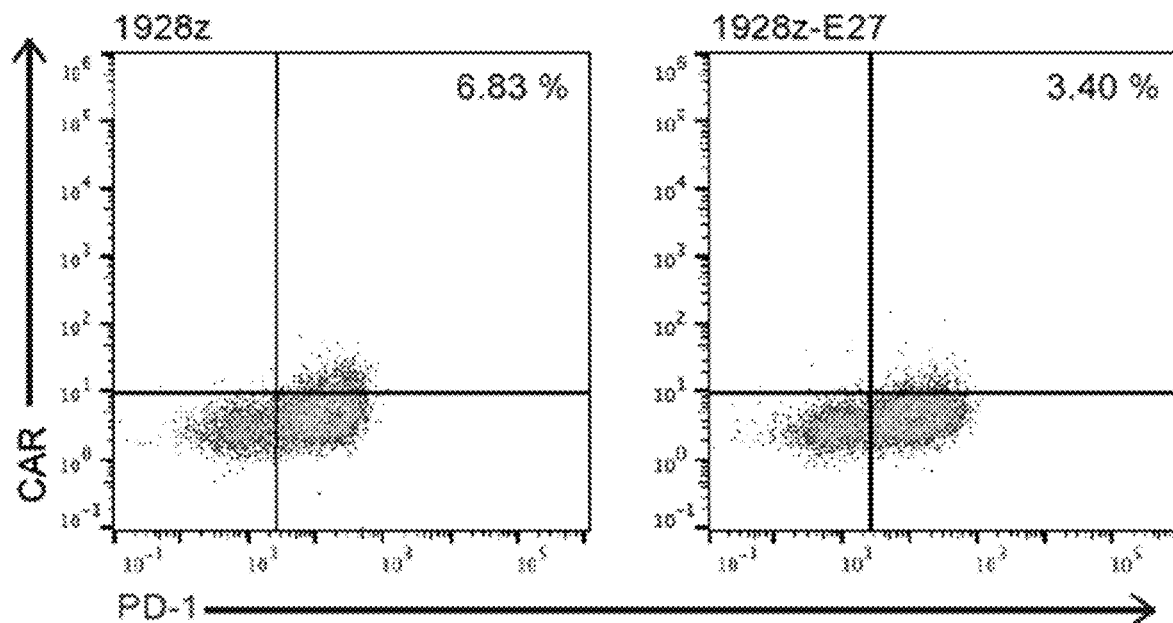
Figure 16D:
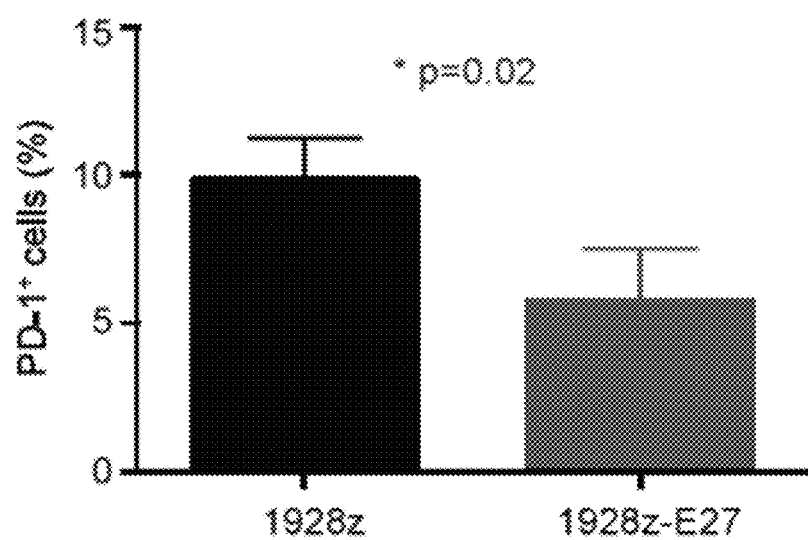
Figure 16E:
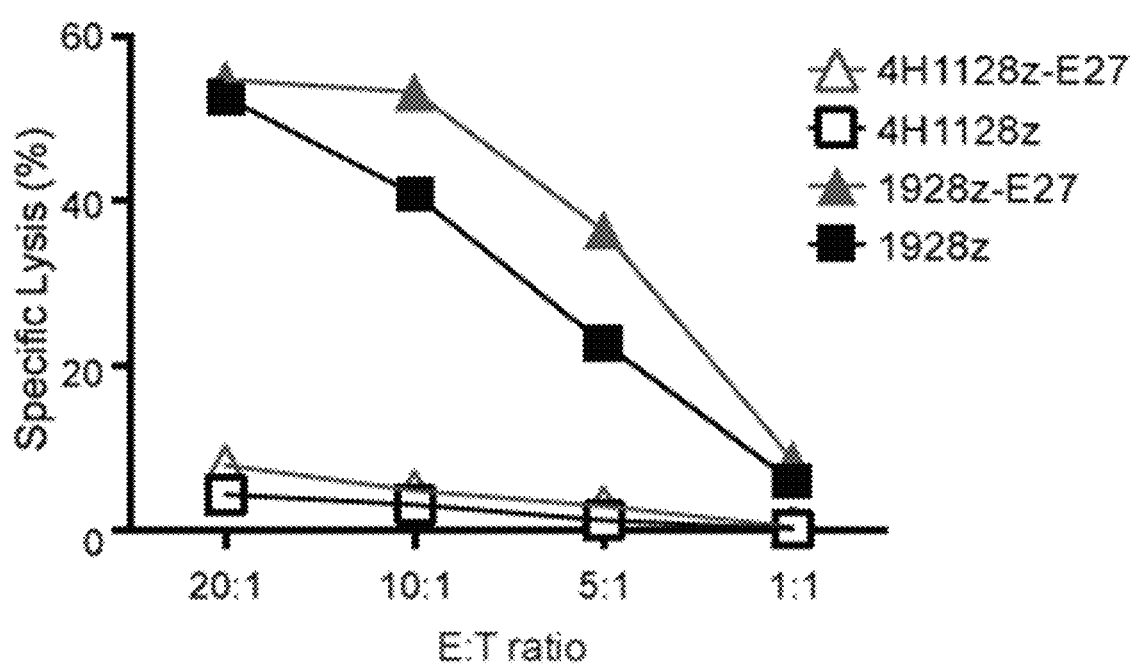

T cells can be co-modified to express CAR and secrete PD-1 blocking scFv, E27. FIG. 16A is a representative flow cytometry plot demonstrating equivalent CAR expression following transduction with the 1928z CAR alone (1928z) or the 1928z CAR and the E27 PD-1 blocking scFv (1928z-E27), following staining with 19E3 mAb that specifically binds the 1928z CAR. FIG. 16B shows a Western blot on SN from 1928z and 1928z-E27 T cells stained with anti-HA mAb, showing only a ~30 kDa protein in the 1928z-E27 cells, demonstrating that the E27 scFv is secreted from the 1928z-E27 transduced T cells and not those transduced with the CAR alone. FIG. 16C is a representative flow cytometry demonstrating lower levels of PD-1 expression on 1928z-E27 T cells compared to 1928z T cells following transduction. Expression of PD-1 was statistically significantly lower on 1928z-E27 T cells compared to 1928z T cells, data shown is mean+/−SEM from 4 independent experiments (FIG. 16D). A 4 hr $^{51}$Cr release assay demonstrating that lysis of Raji tumor cells was unaffected by secretion of the E27 scFv. 1928z and 1928z-E27 T cells lysed Raji tumor cells equivalently. Control 4H1128z-E27 T cells mediated no increase in lysis of Raji cells compared to 4H1128z T cells (FIG. 16 E). Data shown is representative of two independent experiments.

Example 14

Figure 17A:
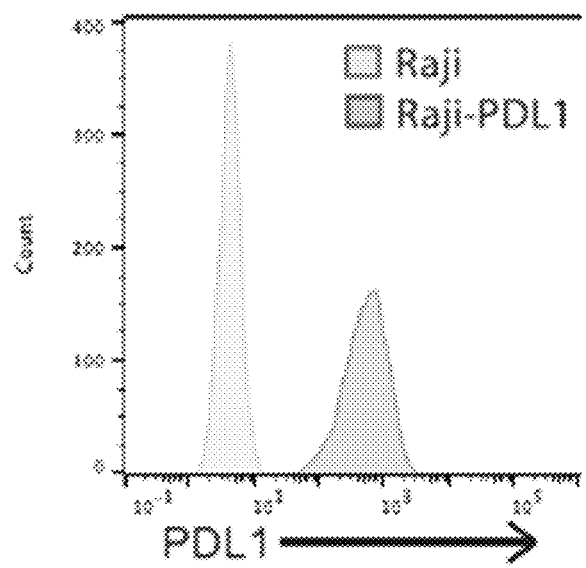
FIGS. 17A-17G show that expression of CAR and E27 protects proliferative and lytic capacity of T cells in the context of CD19$^+$ PD-L1$^+$ tumor cells. A Raji tumor cells were retrovirally modified to express human PD-L1 (Raji-PDL1) and were stained with mAb specific for PD-L1. Parental Raji tumor (Raji) express no PD-L1 and Raji-PDL1 tumor cells expressed high levels of PD-L1. B Representative flow cytometry plots showing 1928z-E27 T cells lyse more Raji-PDL1 tumor cells compared to 1928z T cells as determined with flow cytometry following 72 hrs co-culture. C 1928z-E27 T cells lyse statistically significantly more Raji-PDL1 tumor cells compared to 1928z T cells, data shown the mean+/−SEM from 4 independent experiments. D 1928z-E27 T cells expand to greater numbers following co-culture with Raji-PDL1 tumor cells as determined by flow cytometry and enumeration beads, data shown is the average total number of T cells +/−SEM from 4 independent experiments. E Representative flow cytometry plot showing increased PD-1 expression on 1928z T cells compared to 1928z-E27 T cells following 7 days co-culture with Raji-PDL1 tumor cells. F 1928z T cells express significantly more PD-1 compared to 1928z-E27 T cells, with regard to percentage positive cells and mean fluorescence intensity (MFI) of PD-1 staining. Data show in the mean+/−SEM from 4 independent experiments. G Representative flow cytometry plots showing increased percentage of 2B4+PD-1+1928z T cells compared to 1928z-E27 cells following coculture with Raji-PDL1 for 7 days. 1928z-E27 T cells also express less BTLA and TIM3 on the 2B4+PD-1+ population. Data shown is representative of 3 independent experiments.
Figure 17B:
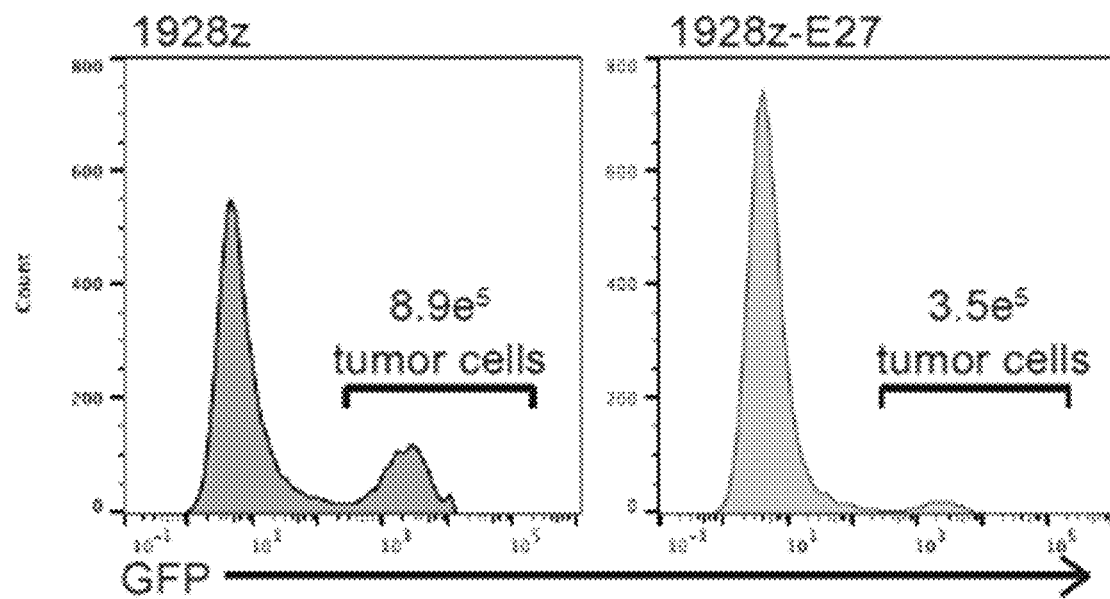
Figure 17C:
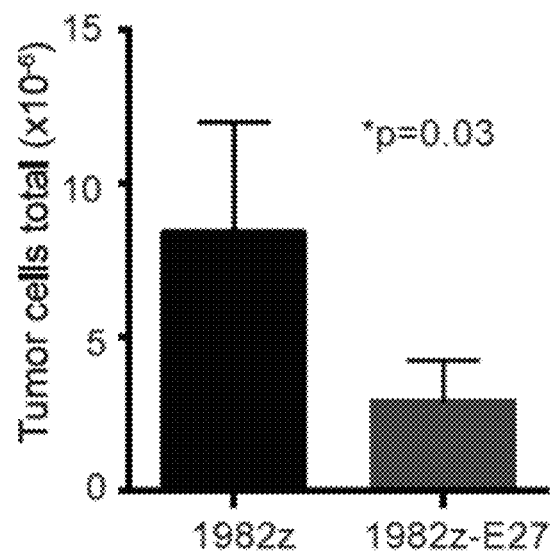
Figure 17D:
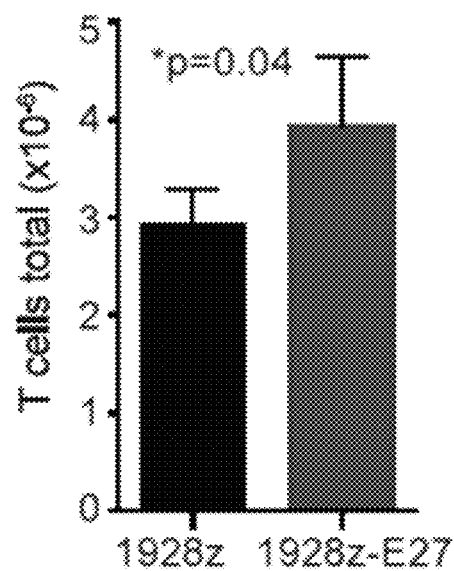
Figure 17E:
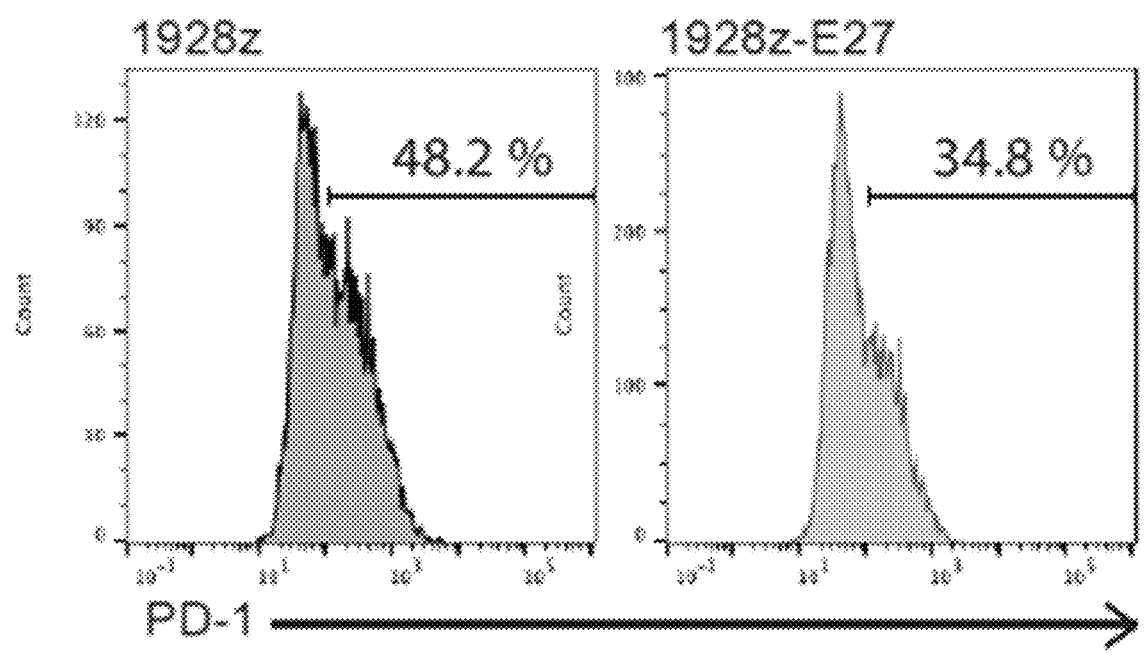
Figure 17F:
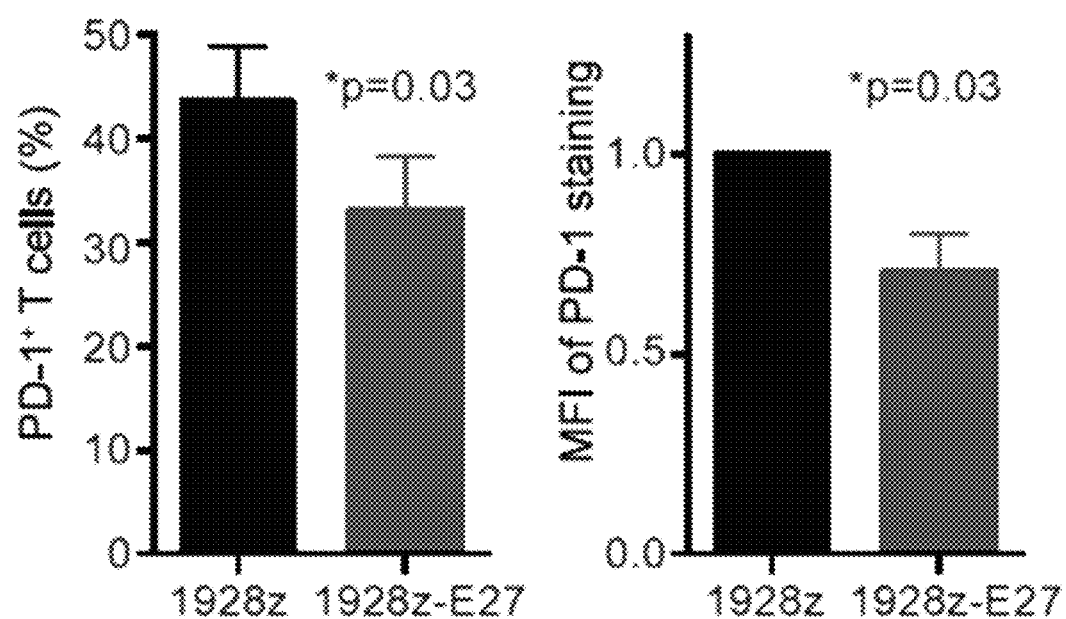
Figure 17G:
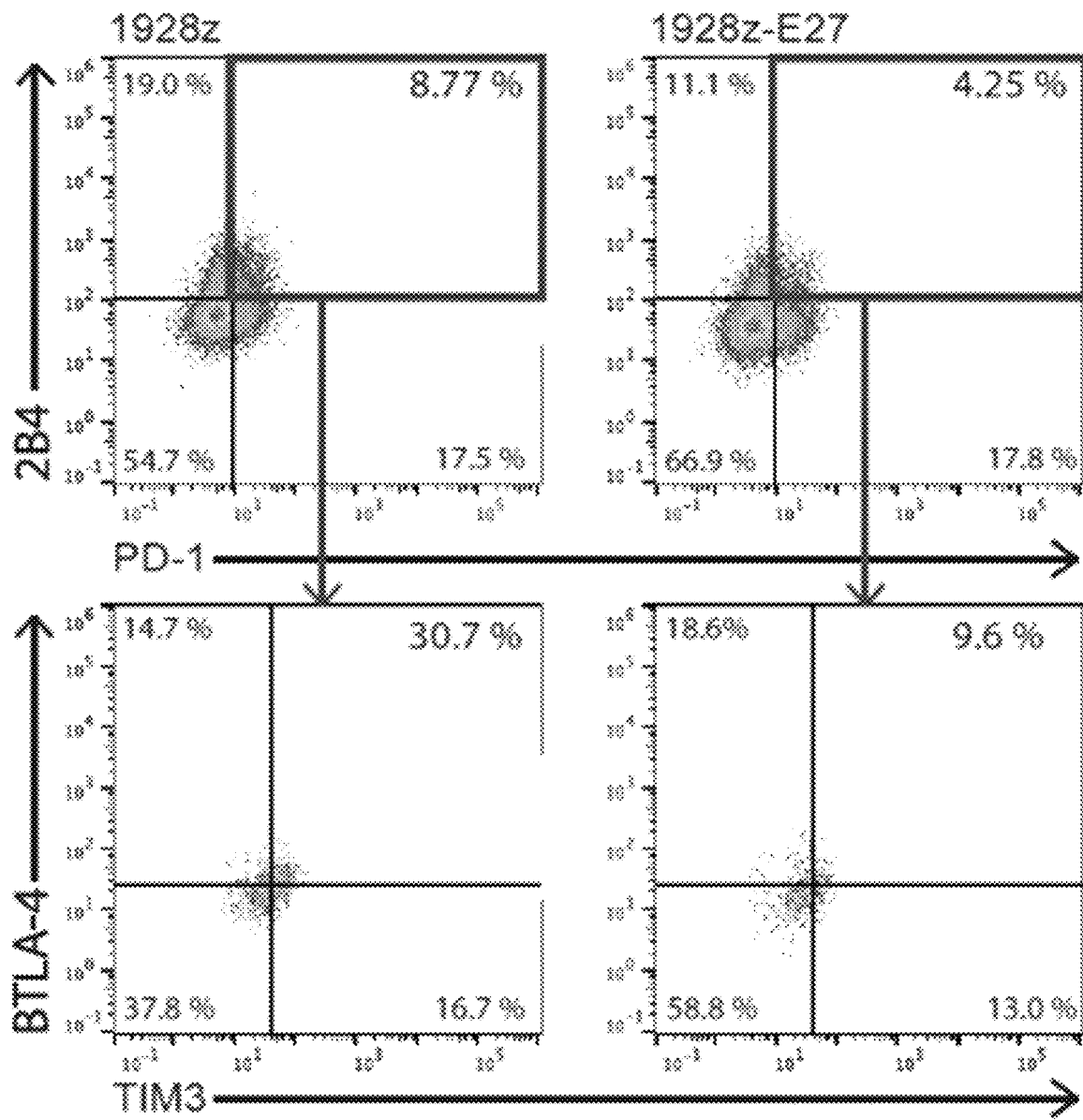

Expression of CAR and E27 protects proliferative and lytic capacity of T cells in the context of CD19$^+$ PD-L1$^+$ tumor cells. Raji tumor cells were retrovirally modified to express human PD-L1 (Raji-PDL1) and were stained with mAb specific for PD-L1. Parental Raji tumor (Raji) express no PD-L1 and Raji-PDL1 tumor cells expressed high levels of PD-L1 (FIG. 17A). FIG. 17B shows representative flow cytometry plots showing 1928z-E27 T cells lyse more Raji-PDL1 tumor cells compared to 1928z T cells as determined with flow cytometry following 72 hrs co-culture. 1928z-E27 T cells lyse statistically significantly more Raji-PDL1 tumor cells compared to 1928z T cells, data shown the mean+/−SEM from 4 independent experiments (FIG. 17C). 1928z-E27 T cells expand to greater numbers following co-culture with Raji-PDL1 tumor cells as determined by flow cytometry and enumeration beads, data shown is the average total number of T cells +/−SEM from 4 independent experiments (FIG. 17D). FIG. 17E shows a representative flow cytometry plot showing increased PD-1 expression on 1928z T cells compared to 1928z-E27 T cells following 7 days co-culture with Raji-PDL1 tumor cells. 1928z T cells express significantly more PD-1 compared to 1928z-E27 T cells, with regard to percentage positive cells and mean fluorescence intensity (MFI) of PD-1 staining. Data show in the mean+/−SEM from 4 independent experiments (FIG. 17F). FIG. 17G shows representative flow cytometry plots showing increased percentage of 2B4+PD-1+1928z T cells compared to 1928z-E27 cells following coculture with Raji-PDL1 for 7 days. 1928z-E27 T cells also express less BTLA and TIM3 on the 2B4+PD-1+ population. Data shown is representative of 3 independent experiments.

Example 15

Figure 18A:
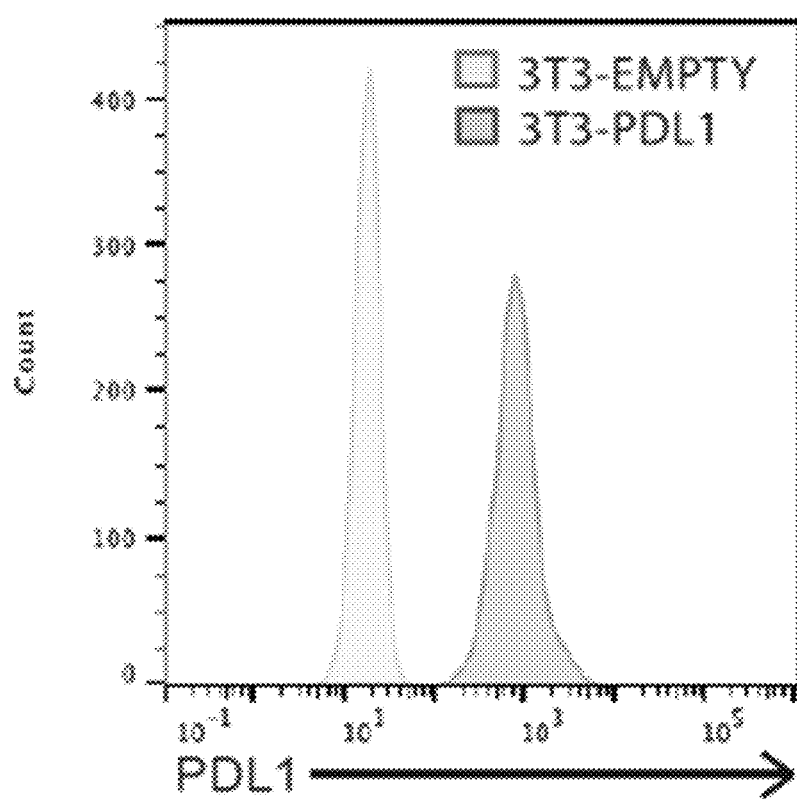
FIGS. 18A-18C show that E27 protects proliferative capacity of CD3/CD28 stimulated T cells in the context of PD-L1. A NIH3T3 cells were retrovirally modified to express human PD-L1 (3T3-PDL1) and were stained with mAb specific for PD-L1. Parental NIH3T3 (3T3-EMPTY) express no PD-L1 and 3T3-PDL1 tumor cells expressed high levels of PD-L1. B 1928z and 1928z-E27 T cells were cultured with 3T3-EMPTY or 3T3-PDL1 cells and stimulated with CD3/CD28 beads. Cells were enumerated and re-plated on new 3T3 cells on days 3, 6, 9 and 12. 1928z T cells had reduced expansion when cultured with 3T3-PDL1 cells compared to 3T3-EMPTY cells. 1928z-E27 cells had equivalent expansion when cultured on 3T3-EMPTY or 3T3-PDL1 cells. Data shown is the mean fold expansion+/−SEM from 4 independent experiments. C Representative flow cytometry plots showing increased expression of 2B4, PD-1, BTLA and TIM3 on 1928z T cells cultured with 3T3-PDL1 compared to 1928z T cells cultured on 3T3-EMPTY cells. 1928z-E27 cells had equivalent expression of 2B4, PD-1, BTLA-4 and TIM3 when cultured with 3T3-EMPTY and 3T3-PDL1. Data shown is representative of 3 independent experiments.
Figure 18B:
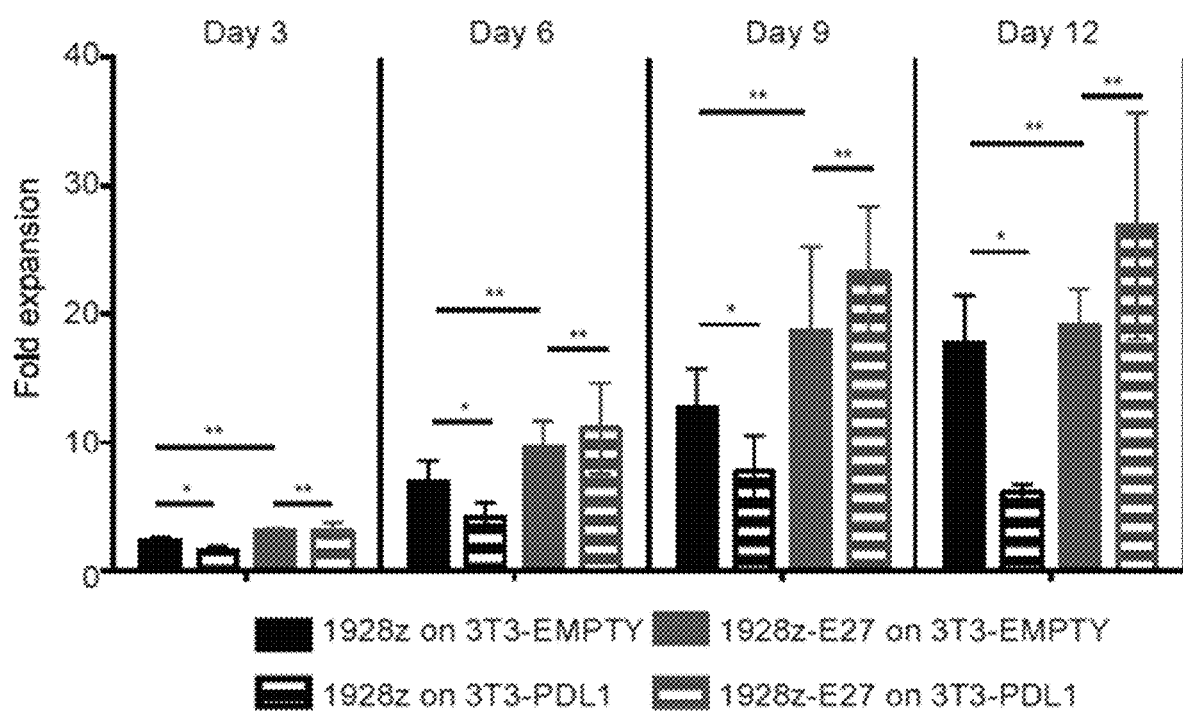
Figure 18C:
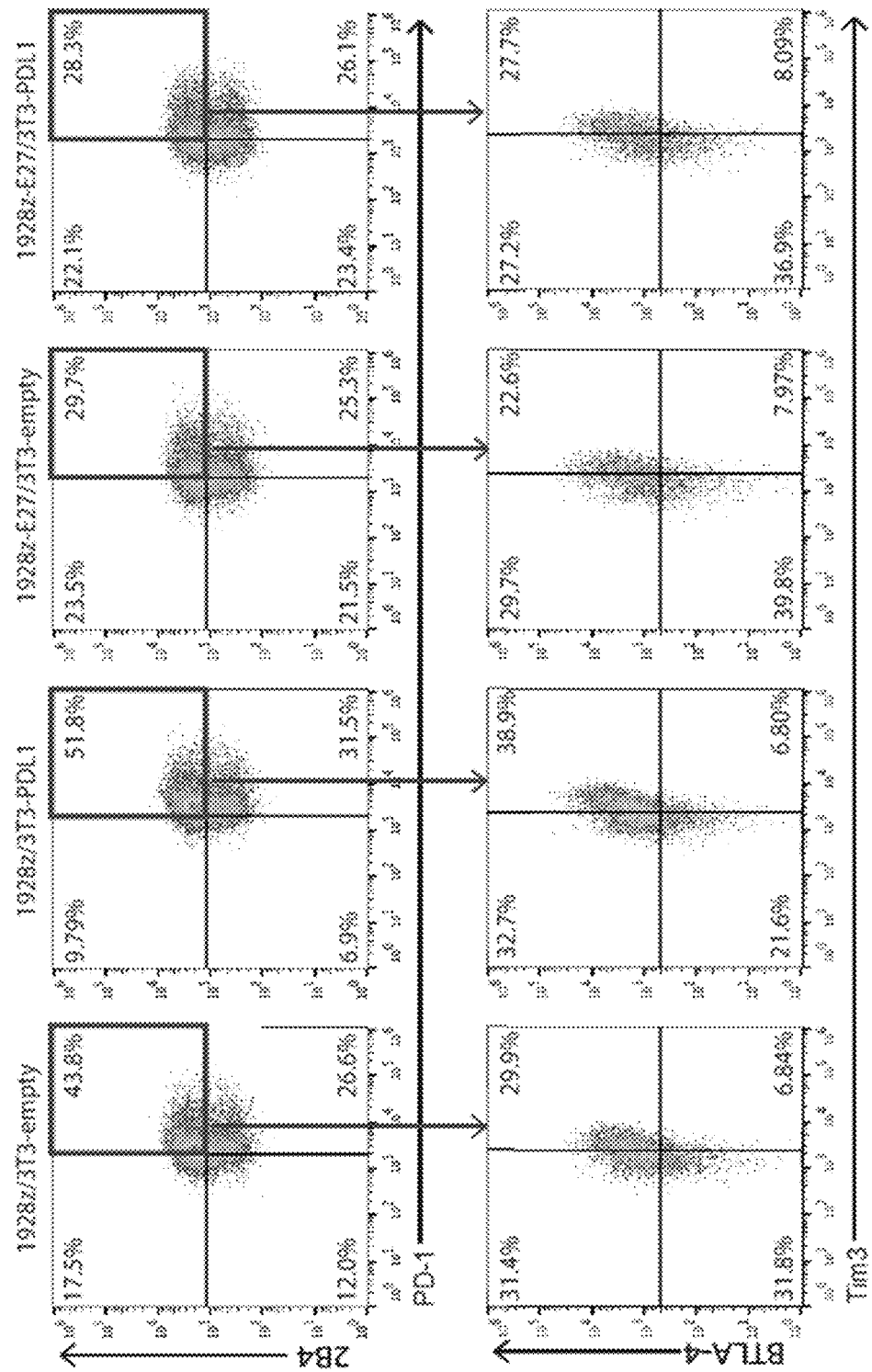

E27 protects proliferative capacity of CD3/CD28 stimulated T cells in the context of PD-L1. NIH3T3 cells were retrovirally modified to express human PD-L1 (3T3-PDL1) and were stained with mAb specific for PD-L1. Parental NIH3T3 (3T3-EMPTY) express no PD-L1 and 3T3-PDL1 tumor cells expressed high levels of PD-L1 (FIG. 18A). 1928z and 1928z-E27 T cells were cultured with 3T3-EMPTY or 3T3-PDL1 cells and stimulated with CD3/CD28 beads. Cells were enumerated and re-plated on new 3T3 cells on days 3, 6, 9 and 12. 1928z T cells had reduced expansion when cultured with 3T3-PDL1 cells compared to 3T3-EMPTY cells. 1928z-E27 cells had equivalent expansion when cultured on 3T3-EMPTY or 3T3-PDL1 cells (FIG. 18B). Data shown is the mean fold expansion+/−SEM from 4 independent experiments. FIG. 18C are representative flow cytometry plots showing increased expression of 2B4, PD-1, BTLA and TIM3 on 1928z T cells cultured with 3T3-PDL1 compared to 1928z T cells cultured on 3T3-EMPTY cells. 1928z-E27 cells had equivalent expression of 2B4, PD-1, BTLA-4 and TIM3 when cultured with 3T3-EMPTY and 3T3-PDL1. Data shown is representative of 3 independent experiments.

Example 16

Figure 19:
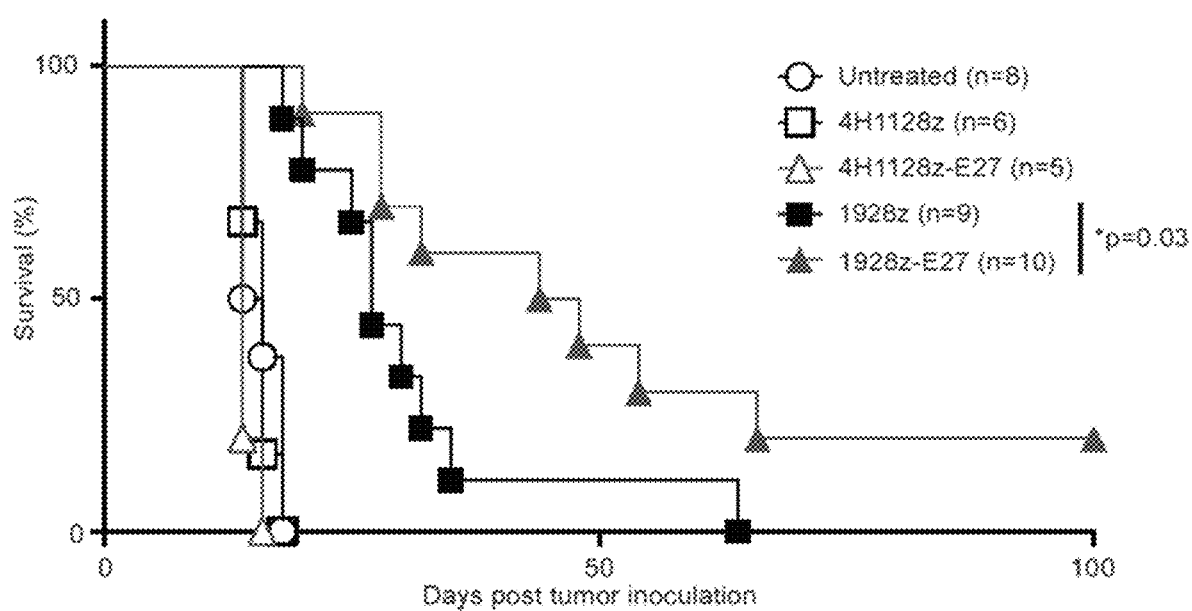
FIG. 19 shows that CAR T cells secreting E27 scFv have increased anti-tumor function in vivo. SCID-Beige mice were inoculated with Raji-PDL1 tumor cells intravenously, and the following day were infused intravenously with CAR T cells. Mice treated with 1928z-E27 T cells had enhanced survival compared to mice treated with 1928z T cells. Mice treated with 1928z T cells survived longer than untreated mice, and mice treated with CAR T cells targeted to an irrelevant antigen, 4H1128z and 4H1128z-E27 T cells. Data shown is from 2 independent experiments.

CAR T cells secreting E27 scFv have increased anti-tumor function in vivo. SCID-Beige mice were inoculated with Raji-PDL1 tumor cells intravenously, and the following day were infused intravenously with CAR T cells. As shown in FIG. 19 mice treated with 1928z-E27 T cells had enhanced survival compared to mice treated with 1928z T cells. Mice treated with 1928z T cells survived longer than untreated mice, and mice treated with CAR T cells targeted to an irrelevant antigen, 4H1128z and 4H1128z-E27 T cells. Data shown is from 2 independent experiments.

Example 17

Figure 20:
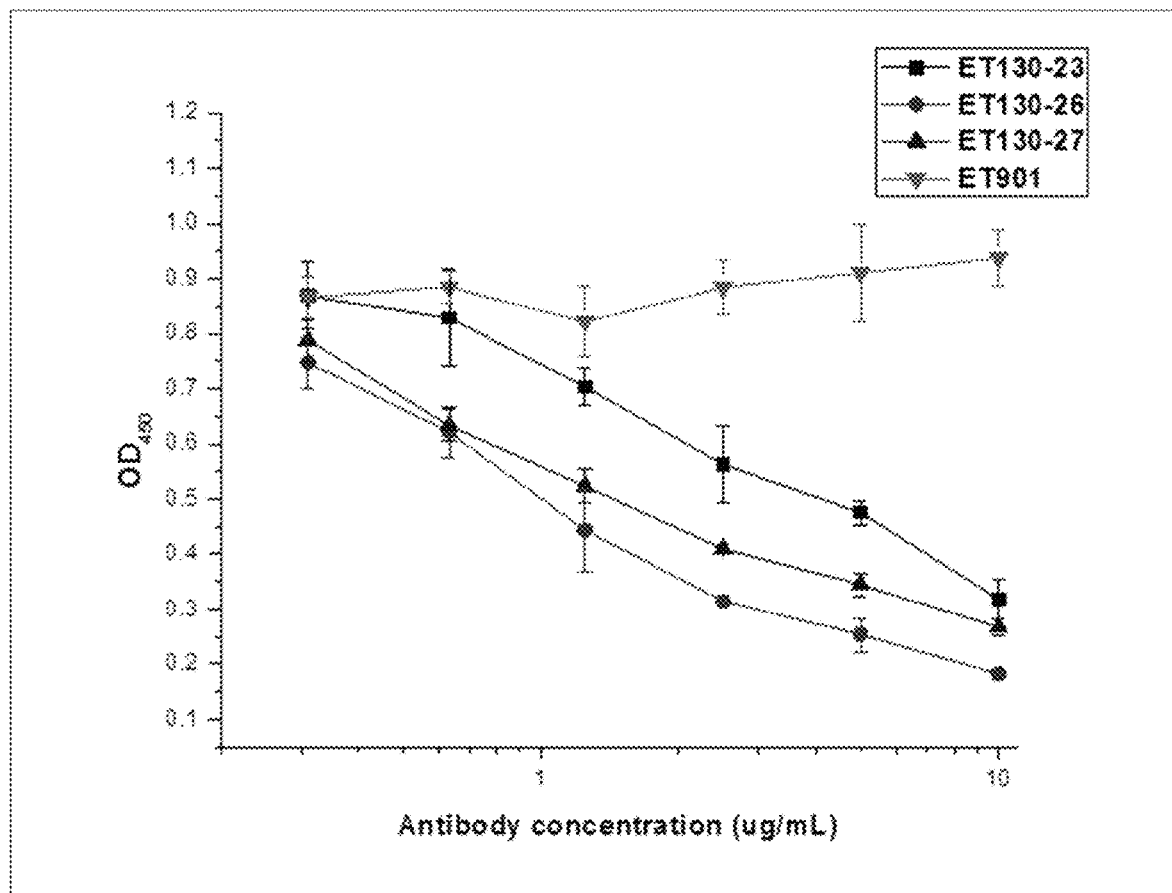
FIG. 20 shows the results of a PD1/PDL1 blocking ELISA using the anti-PD-1 antibodies, ET130-23, ET130-26 and ET130-27. ET901 (negative control) showed no binding, while ET130-23, ET130-26 and ET130-27 showed a blocking effect to PD1/PDL1 binding over a range of concentrations between 0.031 and 10 µg/ml.

Anti-PD-1 antibodies ET130-23, ET130-26 and ET130-27 were tested by ELISA to check the blocking effect to PD1/PDL1 binding. As shown in FIG. 20, ET901 (negative control) showed no binding, while ET130-23, ET130-26 and ET130-27 showed a blocking effect to PD1/PDL1 binding over a range of concentrations between 0.031 and 10 µg/ml.

Figure 21:
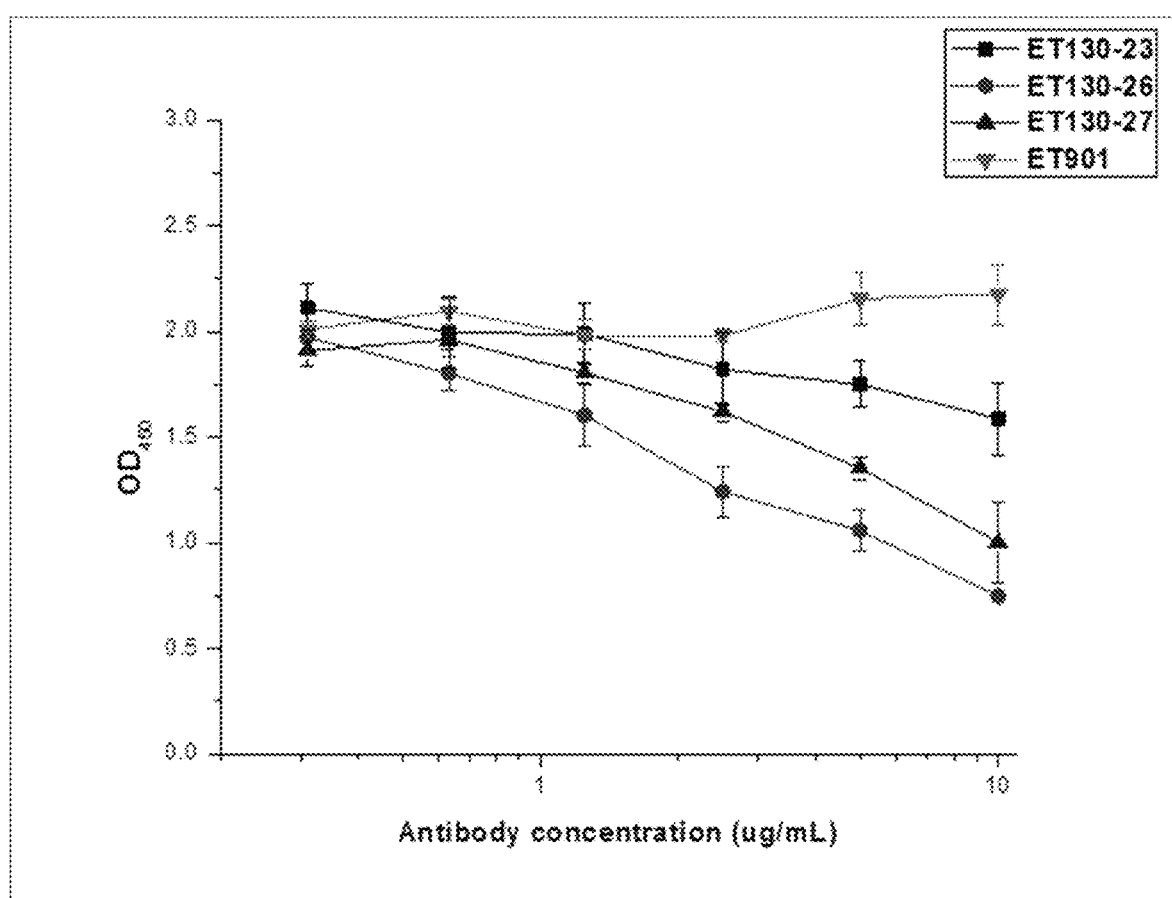
FIG. 21 shows the results of a PD1/PDL2 blocking ELISA using the anti-PD-1 antibodies, ET130-23, ET130-26 and ET130-27. ET901 (negative control) showed no binding, while ET130-23, ET130-26 and ET130-27 showed a blocking effect to PD1/PDL1 binding over a range of concentrations between 0.031 and 10 µg/ml.

Similarly, ET130-23, ET130-26 and ET130-27 were tested by ELISA to check the blocking effect to PD1/PDL2 binding. As shown in FIG. 21, ET901 (negative control) showed no binding, while ET130-23, ET130-26 and ET130-27 showed a blocking effect to PD1/PDL2 binding over the same range of concentrations. ET130-26 showed the highest blocking effect against PD1/PDL2, while ET130-23 showed the lowest effect. The blocking pattern is parallel to PD1/PDL1 binding.

Example 18

The application of the anti-PD-1 scFvs or monoclonal antibodies is investigated for the ability of the scFvs or monoclonal antibodies to dampen the immune response and subvert autoimmune diseases. This can also be investigated using murine models of GVHD. Infusion of human T cells into irradiated NOD.SCID.IL-2Rγ$^{-/-}$ results in engraftment of human cells and severe GVHD, where the human T cells attack the murine tissues. T cells secreting an anti-PD-1 scFv (or T cells augmented with injection of monoclonal antibodies) are infused into a subject and the development of GVHD is assessed. When the anti-PD-1 scFv/mAb is agonistic, the GVHD response is inhibited due to suppression of the human T cells.

REFERENCES

Brentjens, R. J., M. L. Davila, et al. (2013). "CD19-targeted T cells rapidly induce molecular remissions in adults with chemotherapy-refractory acute lymphoblastic leukemia." *Sci Transl Med* 5(177): 177ra138.

Brentjens, R. J., J. B. Latouche, et al. (2003). "Eradication of systemic B-cell tumors by genetically targeted human T lymphocytes co-stimulated by CD80 and interleukin-15." *Nat Med* 9(3): 279-286.

Brentjens, R. J., E. Santos, et al. (2007). "Genetically targeted T cells eradicate systemic acute lymphoblastic leukemia xenografts." *Clin Cancer Res* 13 (18 Pt 1): 5426-5435.

Davila, M. L., I. Riviere, et al. (2014). "Efficacy and toxicity management of 19-28z CAR T cell therapy in B cell acute lymphoblastic leukemia." *Sci Transl Med* 6(224): 224ra225.

We claim:
1. A recombinant antigen-binding protein or antigen-binding fragment thereof, wherein the antigen is PD-1, comprising at least one of:
 (A) an antigen binding region comprising an amino acid sequence that is at least 91% identical to SEQ ID NO: 53;
 (B) an antigen binding region comprising a light chain variable region and a heavy chain variable region having amino acid sequences that are at least 80% identical to SEQ ID NO: 49 and at least 80% identical to SEQ ID NO:51, respectively; and
 (C) an antigen binding region comprising
  a light chain (LC) comprising LCCDR1, LCCDR2 and LCCDR3 having the amino acid sequences that are at least 80% identical to NIGSKS (SEQ ID NO: 34), YDS and at least 80% identical to QVWDSSSDYV (SEQ ID NO: 45), respectively, and a heavy chain (HC) comprising HCCDR1, HCCDR2 and HCCDR3 having amino acid sequences that are at least 80% identical to GFTFSSYA (SEQ ID NO: 46), at least 80% identical to ISGSGGST (SEQ ID NO. 47) and at least 80% identical to ARNYISMFDS (SEQ ID NO: 48), respectively.

2. The recombinant antigen-binding protein of claim 1, wherein said protein is an antibody.

3. The recombinant antigen-binding protein of claim 2, wherein the antibody is a human antibody.

4. The recombinant antigen-binding protein of claim 2, wherein said antibody or antigen-binding fragment thereof is intact Ig, Fab, F(ab')$_2$, Fv, or scFv.

5. The antigen-binding protein of claim 1, wherein said antigen-binding protein is a PD-1 antagonist.

6. The antigen-binding protein of claim 1, wherein said antigen-binding protein is a chimeric antigen receptor.

7. A nucleic acid encoding an antigen-binding protein of claim 1.

8. A vector comprising a nucleic acid of claim 7.

9. A cell comprising a nucleic acid of claim 7.

10. A cell comprising a vector of claim 8.

11. An antigen-binding protein of claim 1 conjugated to a therapeutic agent.

12. The antigen-binding protein of claim 11, wherein said therapeutic agent is a drug, toxin, radioisotope, protein, or peptide.

13. A pharmaceutical composition comprising an antigen-binding protein of claim 1.

14. A pharmaceutical composition comprising a nucleic acid of claim 7.

15. A pharmaceutical composition comprising a vector of claim 8.

16. A pharmaceutical composition comprising a cell that expresses an antigen-binding protein of claim 14.

17. A method of increasing a T cell response in a subject comprising administering to the subject a therapeutically effective amount of an antigen-binding protein or an antigen binding fragment thereof of claim 14 or a nucleic acid that encodes the antigen-binding protein or antigen binding fragment thereof.

18. The method of claim 17, wherein the antigen-binding protein or antigen binding fragment thereof inhibits, reduces, modulates or abolishes signal transduction mediated by PD-1.

19. A vector comprising a first nucleic acid encoding the recombinant antigen-binding protein of claim 14 and a second nucleic acid encoding a chimeric antigen receptor, wherein said recombinant antigen-binding protein is not identical to said chimeric antigen receptor.

20. A cell comprising the vector of claim 19.

21. A cell comprising a first nucleic acid encoding the recombinant antigen-binding protein of claim 14 and a second nucleic acid encoding a chimeric antigen receptor, wherein said recombinant antigen-binding protein is not identical to said chimeric antigen receptor.

22. A cell comprising a recombinant antigen-binding protein of claim 14 and a chimeric antigen receptor, wherein said recombinant antigen-binding protein is not identical to said chimeric antigen receptor.

23. A vector or a cell comprising a vector, wherein the vector comprises a polynucleotide that encodes the recombinant antigen-binding protein of claim 14, wherein the recombinant antigen-binding protein is an antibody.

24. The vector or cell comprising the vector of claim 23, wherein the recombinant antigen-binding protein is a human antibody.

25. The vector or cell comprising the vector of claim 23, wherein the recombinant antigen-binding protein is an intact Ig, Fab, F(ab')$_2$, Fv, or scFv.

26. The vector or cell comprising the vector of claim 23, wherein the recombinant antigen-binding protein is a PD-1 antagonist.

27. The vector or cell comprising the vector of claim 23, wherein the recombinant antigen-binding protein is a secretable protein.

28. The vector or cell comprising the vector of claim 23, wherein said vector further comprises a polynucleotide that encodes a chimeric antigen receptor and the chimeric antigen receptor specifically binds to CD19.

29. The vector or cell comprising the vector of claim 23, wherein said vector further comprises a polynucleotide that encodes a chimeric antigen receptor and the chimeric antigen receptor comprises a transmembrane domain.

30. A pharmaceutical composition comprising the vector or cell comprising the vector of claim 23.

31. A method of increasing a T cell response in a subject comprising administering to the subject a therapeutically effective amount of the vector of claim 23, wherein the recombinant PD-1 antigen-binding protein is a PD-1 antagonist.

32. A method of increasing a T cell response in a subject comprising administering to the subject a therapeutically effective amount of a pharmaceutical composition, wherein the pharmaceutical composition comprises the vector of claim 23.

33. The method of claim 32, wherein the recombinant PD-1 antigen-binding protein inhibits, reduces, modulates or abolishes signal transduction mediated by PD-1.

34. A vector that encodes an antigen-binding protein of claim 14 and a chimeric antigen receptor or a cell comprising the vector, wherein at least one of the antigen-binding protein and chimeric antigen receptor is conjugated to a therapeutic agent.

35. The vector of claim 34, wherein said therapeutic agent is a drug, toxin, radioisotope, protein, or peptide.

36. The recombinant antigen-binding protein of claim 14, wherein the antigen is PD-1, comprising at least one of:
 (A) an antigen binding region comprising the amino acid sequence of SEQ ID NO: 53;
 (B) an antigen binding region comprising a light chain variable region and a heavy chain variable region having the amino acid sequences SEQ ID NO: 49 and SEQ ID NO:51, respectively; and
 (C) an antigen binding region comprising
  a light chain (LC) comprising LCCDR1, LCCDR2 and LCCDR3 having the amino acid sequences NIGSKS (SEQ ID NO: 34), YDS and QVWDSSSDYV (SEQ ID NO: 45), respectively, and a heavy chain (HC) comprising HCCDR1, HCCDR2 and HCCDR3 having amino acid sequences GFTFSSYA (SEQ ID NO: 46), ISGSGGST (SEQ ID NO. 47) and ARNYISMFDS (SEQ ID NO: 48).

\* \* \* \* \*

SEQUENCE LISTING

```
<160> NUMBER OF SEQ ID NOS: 143

<210> SEQ ID NO 1
<211> LENGTH: 6
<212> TYPE: PRT
<213> ORGANISM: Artificial Sequence
<220> FEATURE:
<223> OTHER INFORMATION: Homo sapiens

<400> SEQUENCE: 1

Gln Ser Ile Ser Ser Tyr
```

<210> SEQ ID NO 2
<211> LENGTH: 9
<212> TYPE: PRT
<213> ORGANISM: Homo sapiens

<400> SEQUENCE: 2

Gln Gln Ser Tyr Ser Thr Pro Leu Thr
1               5

<210> SEQ ID NO 3
<211> LENGTH: 8
<212> TYPE: PRT
<213> ORGANISM: Homo sapiens

<400> SEQUENCE: 3

Gly Phe Thr Ser Ser Ser Tyr Trp
1               5

<210> SEQ ID NO 4
<211> LENGTH: 8
<212> TYPE: PRT
<213> ORGANISM: Homo sapiens

<400> SEQUENCE: 4

Ile Lys Gln Asp Gly Ser Glu Lys
1               5

<210> SEQ ID NO 5
<211> LENGTH: 9
<212> TYPE: PRT
<213> ORGANISM: Homo sapiens

<400> SEQUENCE: 5

Ala Arg Gly Gly Trp Ser Tyr Asp Met
1               5

<210> SEQ ID NO 6
<211> LENGTH: 110
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Ser Arg
                100                 105                 110

<210> SEQ ID NO 7
<211> LENGTH: 324
<212> TYPE: DNA

<213> ORGANISM: Homo sapiens

<400> SEQUENCE: 7

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgctcac tttcggcgga   300
gggaccaagg tggagatcaa acgt                                          324
```

<210> SEQ ID NO 8
<211> LENGTH: 116
<212> TYPE: PRT
<213> ORGANISM: Homo sapiens

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Ser Tyr
            20                  25                  30

Trp Met Ser Trp Val Arg Gln Ala Pro Gly Arg Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Trp Ser Tyr Asp Met Trp Gly Gln Gly Thr Leu Val
            100                 105                 110

Thr Val Ser Ser
        115
```

<210> SEQ ID NO 9
<211> LENGTH: 348
<212> TYPE: DNA
<213> ORGANISM: Homo sapiens

<400> SEQUENCE: 9

```
gaggtgcagc tggtggagtc tgggggaggc ttggtccagc ctgggggggtc cctgagactc    60
tcctgtgcag cctctggatt cacctctagt agctattgga tgagctgggt ccgccaggct   120
ccagggagag gctggagtg gtggccaac ataaagcaag atggaagtga aaagtactat   180
gtggactctg tgaagggccg attcaccatc tccagagaca acgccaagaa ctcactgtat   240
ctgcaaatga acagcctgag agccgaggac actgccgtgt attactgtgc gcgcggtggt   300
tggtcttacg atatgtgggg tcaaggtact ctggtgaccg tctcctca                348
```

<210> SEQ ID NO 10
<211> LENGTH: 259
<212> TYPE: PRT
<213> ORGANISM: Homo sapiens

<400> SEQUENCE: 10

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Ser Arg Gly Gly
            100                 105                 110

Gly Gly Ser Gly Gly Gly Gly Ser Gly Gly Gly Gly Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Thr Ser Ser Ser Tyr Trp Met Ser
145                 150                 155                 160

Trp Val Arg Gln Ala Pro Gly Arg Gly Leu Glu Trp Val Ala Asn Ile
                165                 170                 175

Lys Gln Asp Gly Ser Glu Lys Tyr Tyr Val Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Gly
    210                 215                 220

Gly Trp Ser Tyr Asp Met Trp Gly Gln Gly Thr Leu Val Thr Val Ser
225                 230                 235                 240

Ser His His His His His His Gly Ala Tyr Pro Tyr Asp Val Pro Asp
                245                 250                 255

Tyr Ala Ser

<210> SEQ ID NO 11
<211> LENGTH: 717
<212> TYPE: DNA
<213> ORGANISM: Homo sapiens

<400> SEQUENCE: 11
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccgctcac tttcggcgga     300
gggaccaagg tggagatcaa acgtggtggt ggtggtagcg gcggcggcgg ctctggtggt     360
ggtggatccg aggtgcagct ggtggagtct gggggaggct tggtccagcc tgggggggtcc    420
ctgagactct cctgtgcagc ctctggattc acctctagta gctattggat gagctgggtc     480
cgccaggctc agggagaggg ctggagtgg gtggccaaca taaagcaaga tggaagtgag      540
aagtactatg tggactctgt gaagggccga ttcaccatct ccagagacaa cgccaagaac     600
tcactgtatc tgcaaatgaa cagcctgaga gccgaggaca ctgccgtgta ttactgtgcg     660
cgcggtggtt ggtcttacga tatgtggggt caaggtactc tggtgaccgt ctcctca       717

<210> SEQ ID NO 12
<211> LENGTH: 9
<212> TYPE: PRT
<213> ORGANISM: Homo sapiens

<400> SEQUENCE: 12

Ser Ser Asn Ile Gly Ala Gly Tyr Ala
1               5

<210> SEQ ID NO 13
<211> LENGTH: 11
<212> TYPE: PRT
<213> ORGANISM: Homo sapiens

<400> SEQUENCE: 13

Gln Ser Tyr Asp Ser Ser Leu Ser Gly Val Ile
1               5                   10

<210> SEQ ID NO 14
<211> LENGTH: 8
<212> TYPE: PRT
<213> ORGANISM: Homo sapiens

<400> SEQUENCE: 14

Gly Tyr Thr Leu Thr Glu Leu Ser
1               5

<210> SEQ ID NO 15
<211> LENGTH: 8
<212> TYPE: PRT
<213> ORGANISM: Homo sapiens

<400> SEQUENCE: 15

Phe Asp Pro Glu Asp Gly Glu Thr
1               5

<210> SEQ ID NO 16
<211> LENGTH: 9
<212> TYPE: PRT
<213> ORGANISM: Homo sapiens

<400> SEQUENCE: 16

Ala Arg Ala Tyr Tyr Gly Phe Asp Gln
1               5

<210> SEQ ID NO 17
<211> LENGTH: 112
<212> TYPE: PRT
<213> ORGANISM: Homo sapiens

<400> SEQUENCE: 17

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ala Val Asn Trp Tyr Gln Leu Leu Pro Gly Thr Ala Pro Lys Leu
        35                  40                  45

Leu Ile Ser Thr Asn Asn Arg Pro Ser Gly Val Pro Asp Arg Phe
    50                  55                  60

Ser Gly Ser Gln Phe Gly Ala Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser

```
                  85                  90                  95
Leu Ser Gly Val Ile Phe Gly Gly Gly Thr Lys Leu Thr Val Leu Gly
        100                 105                 110

<210> SEQ ID NO 18
<211> LENGTH: 336
<212> TYPE: DNA
<213> ORGANISM: Homo sapiens

<400> SEQUENCE: 18
cagtctgtgt tgacgcagcc gccctcagtg tctggggccc cagggcagag ggtcaccatc     60
tcctgcactg ggagcagctc aacatcgggg caggttatg ctgtaaattg gtaccagctt    120
cttccaggaa cagcccccaa actcctcatc tctactaaca caatcggcc ctcaggggtc    180 cctgaccgat tctctggctc ccagtttggc gcctctgcct ccctggccat cactggactc    240
caggctgagg atgaggctga ttattactgc cagtcctatg acagtagtct gagtggtgtg    300
atattcggcg agggaccaa gctgaccgtc ctaggt                               336

<210> SEQ ID NO 19
<211> LENGTH: 116
<212> TYPE: PRT
<213> ORGANISM: Homo sapiens

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Tyr Tyr Gly Phe Asp Gln Trp Gly Gln Gly Thr Leu Val
            100                 105                 110

Thr Val Ser Ser
        115

<210> SEQ ID NO 20
<211> LENGTH: 348
<212> TYPE: DNA
<213> ORGANISM: Homo sapiens

<400> SEQUENCE: 20
gaagtgcagc tggtgcagtc tggggctgag gtgaagaagc tggggcctc agtgaaggtc      60 tcctgcaagg tttccggata cccctcact gaattatcca tgcactgggt gcgacaggct    120
cctggaaaag gcttgagtg gatgggaggt tttgatcctg aagatggtga aacaatctac    180
gcacagaagt tccagggcag agtcaccatg accgaggaca catctacaga cacagcctac    240
atggagctga gcagcctgag gtctgaggac actgccgtgt attactgtgc gcgcgcttac    300
tacggtttcg atcagtgggg tcaaggtact ctggtgaccg tctcctca                 348

<210> SEQ ID NO 21
```

```
<211> LENGTH: 257
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Ser Glu Val Gln Leu Val
            115                 120                 125

Gln Ser Gly Ala Glu Val Lys Lys Pro Gly Ala Ser Val Lys Val Ser
    130                 135                 140

Cys Lys Val Ser Gly Tyr Thr Leu Thr Glu Leu Ser Met His Trp Val
145                 150                 155                 160

Arg Gln Ala Pro Gly Lys Gly Leu Glu Trp Met Gly Gly Phe Asp Pro
                165                 170                 175

Glu Asp Gly Glu Thr Ile Tyr Ala Gln Lys Phe Gln Gly Arg Val Thr
            180                 185                 190

Met Thr Glu Asp Thr Ser Thr Asp Thr Ala Tyr Met Glu Leu Ser Ser
        195                 200                 205

Leu Arg Ser Glu Asp Thr Ala Val Tyr Tyr Cys Ala Arg Ala Tyr Tyr
    210                 215                 220

Gly Phe Asp Gln Trp Gly Gln Gly Thr Leu Val Thr Val Ser Ser His
225                 230                 235                 240

His His His His His Gly Ala Tyr Pro Tyr Asp Val Pro Asp Tyr Ala
                245                 250                 255

Ser

<210> SEQ ID NO 22
<211> LENGTH: 729
<212> TYPE: PRT
<213> ORGANISM: Homo sapiens

<400> SEQUENCE: 22

Cys Ala Gly Thr Cys Thr Gly Thr Gly Thr Thr Gly Ala Cys Gly Cys
1               5                   10                  15

Ala Gly Cys Cys Gly Cys Cys Cys Thr Cys Ala Gly Thr Gly Thr Cys
            20                  25                  30

Thr Gly Gly Gly Gly Cys Cys Cys Ala Gly Gly Gly Cys Ala Gly Ala
            35                  40                  45

Ala Gly Gly Gly Thr Cys Ala Cys Ala Thr Cys Thr Cys Cys Thr
    50                  55                  60

Gly Cys Ala Cys Thr Gly Gly Gly Ala Gly Cys Ala Gly Cys Thr Cys
65                  70                  75                  80
```

```
Cys Ala Ala Cys Ala Thr Cys Gly Gly Gly Cys Ala Gly Gly Thr
                85                  90                  95

Thr Ala Thr Gly Cys Thr Gly Thr Ala Ala Thr Thr Gly Gly Thr
                100                 105                 110

Ala Cys Cys Ala Gly Cys Thr Thr Cys Thr Thr Cys Cys Ala Gly Gly
                115                 120                 125

Ala Ala Cys Ala Gly Cys Cys Cys Cys Ala Ala Ala Cys Thr Cys
                130                 135                 140

Cys Thr Cys Ala Thr Cys Thr Cys Thr Ala Cys Thr Ala Ala Cys Ala
145                 150                 155                 160

Ala Cys Ala Ala Thr Cys Gly Gly Cys Cys Cys Thr Cys Ala Gly Gly
                165                 170                 175

Gly Gly Thr Cys Cys Cys Thr Gly Ala Cys Cys Gly Ala Thr Thr Cys
                180                 185                 190

Thr Cys Thr Gly Gly Cys Thr Cys Cys Cys Ala Gly Thr Thr Thr Gly
                195                 200                 205

Gly Cys Gly Cys Cys Thr Cys Thr Gly Cys Cys Thr Cys Cys Cys Thr
                210                 215                 220

Gly Gly Cys Cys Ala Thr Cys Ala Cys Thr Gly Gly Ala Cys Thr Cys
225                 230                 235                 240

Cys Ala Gly Gly Cys Thr Gly Ala Gly Gly Ala Thr Gly Ala Gly Gly
                245                 250                 255

Cys Thr Gly Ala Thr Thr Ala Thr Thr Ala Cys Thr Gly Cys Cys Ala
                260                 265                 270

Gly Thr Cys Cys Thr Ala Thr Gly Ala Cys Ala Gly Cys Ala Gly Thr
                275                 280                 285

Cys Thr Gly Ala Gly Thr Gly Gly Thr Gly Thr Gly Ala Thr Ala Thr
                290                 295                 300

Thr Cys Gly Gly Cys Gly Gly Ala Gly Gly Gly Ala Cys Cys Ala Ala
305                 310                 315                 320

Gly Cys Thr Gly Ala Cys Cys Gly Thr Cys Cys Thr Ala Gly Gly Thr
                325                 330                 335

Gly Gly Thr Gly Gly Thr Gly Gly Thr Gly Gly Thr Ala Gly Cys Gly
                340                 345                 350

Gly Cys Gly Gly Cys Gly Gly Cys Gly Gly Cys Thr Cys Thr Gly Gly
                355                 360                 365

Thr Gly Gly Thr Gly Gly Thr Gly Gly Ala Thr Cys Cys Gly Ala Ala
                370                 375                 380

Gly Thr Gly Cys Ala Gly Cys Thr Gly Gly Thr Gly Cys Ala Gly Thr
385                 390                 395                 400

Cys Thr Gly Gly Gly Gly Cys Thr Gly Ala Gly Gly Thr Gly Ala Ala
                405                 410                 415

Gly Ala Ala Gly Cys Cys Thr Gly Gly Gly Cys Cys Thr Cys Ala
                420                 425                 430

Gly Thr Gly Ala Ala Gly Gly Thr Cys Thr Cys Cys Thr Gly Cys Ala
                435                 440                 445

Ala Gly Gly Thr Thr Thr Cys Cys Gly Gly Ala Thr Ala Cys Ala Cys
450                 455                 460

Cys Cys Thr Cys Ala Cys Thr Gly Ala Ala Thr Ala Thr Cys Cys
465                 470                 475                 480

Ala Thr Gly Cys Ala Cys Thr Gly Gly Gly Thr Gly Cys Gly Ala Cys
                485                 490                 495

Ala Gly Gly Cys Thr Cys Cys Thr Gly Gly Ala Ala Ala Ala Gly Gly
```

```
                500             505                 510
Gly Cys Thr Thr Gly Ala Gly Thr Gly Ala Thr Gly Gly Ala
            515                 520                 525
Gly Gly Thr Thr Thr Thr Gly Ala Thr Cys Cys Thr Gly Ala Ala Gly
            530                 535                 540
Ala Thr Gly Gly Thr Gly Ala Ala Ala Cys Ala Ala Thr Cys Thr Ala
545                 550                 555                 560
Cys Gly Cys Ala Cys Ala Gly Ala Ala Gly Thr Thr Cys Cys Ala Gly
                565                 570                 575
Gly Gly Cys Ala Gly Ala Gly Thr Cys Ala Cys Cys Ala Thr Gly Ala
                580                 585                 590
Cys Cys Gly Ala Gly Ala Cys Ala Cys Ala Thr Cys Thr Ala Cys
                595                 600                 605
Ala Gly Ala Cys Ala Cys Ala Gly Cys Cys Thr Ala Cys Ala Thr Gly
            610                 615                 620
Gly Ala Gly Cys Thr Gly Ala Gly Cys Ala Gly Cys Cys Thr Gly Ala
625                 630                 635                 640
Gly Gly Thr Cys Thr Gly Ala Gly Gly Ala Cys Ala Cys Thr Gly Cys
                645                 650                 655
Cys Gly Thr Gly Thr Ala Thr Ala Cys Thr Gly Thr Gly Cys Gly
                660                 665                 670
Cys Gly Cys Gly Cys Thr Thr Ala Cys Thr Ala Cys Gly Gly Thr Thr
            675                 680                 685
Thr Cys Gly Ala Thr Cys Ala Gly Thr Gly Gly Gly Thr Cys Ala
            690                 695                 700
Ala Gly Gly Thr Ala Cys Thr Cys Thr Gly Gly Thr Gly Ala Cys Cys
705                 710                 715                 720
Gly Thr Cys Thr Cys Cys Thr Cys Ala
                725

<210> SEQ ID NO 23
<211> LENGTH: 8
<212> TYPE: PRT
<213> ORGANISM: Homo sapiens

<400> SEQUENCE: 23

Ser Ser Asn Ile Gly Asn Asn Ala
1               5

<210> SEQ ID NO 24
<211> LENGTH: 11
<212> TYPE: PRT
<213> ORGANISM: Homo sapiens

<400> SEQUENCE: 24

Ala Ala Trp Asp Asp Ser Val Asn Gly Tyr Val
1               5                   10

<210> SEQ ID NO 25
<211> LENGTH: 8
<212> TYPE: PRT
<213> ORGANISM: Homo sapiens

<400> SEQUENCE: 25

Gly Tyr Thr Phe Thr Arg Phe Gly
1               5

<210> SEQ ID NO 26
```

<211> LENGTH: 8
<212> TYPE: PRT
<213> ORGANISM: Homo sapiens

<400> SEQUENCE: 26

Ile Ser Val Asn Asn Gly Asn Thr
1               5

<210> SEQ ID NO 27
<211> LENGTH: 10
<212> TYPE: PRT
<213> ORGANISM: Homo sapiens

<400> SEQUENCE: 27

Ala Arg Tyr Met Tyr Gly Arg Arg Asp Ser
1               5                   10

<210> SEQ ID NO 28
<211> LENGTH: 111
<212> TYPE: PRT
<213> ORGANISM: Homo sapiens

<400> SEQUENCE: 28

Gln Ala Val Leu Thr Gln Pro Pro Ser Met Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asn Asp Leu Leu Ser Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Val
                85                  90                  95

Asn Gly Tyr Val Phe Gly Thr Gly Thr Lys Val Thr Val Leu Gly
            100                 105                 110

<210> SEQ ID NO 29
<211> LENGTH: 333
<212> TYPE: DNA
<213> ORGANISM: Homo sapiens

<400> SEQUENCE: 29
caggctgtgc tgactcagcc accctcgatg tctgaagccc ccaggcagag ggtcaccatc     60
tcctgttctg gaagcagctc caacatcgga ataatgctg taaactggta ccagcagctc    120
ccaggaaagg ctcccaaact cctcatctat tataatgatc tgctgtcctc agggg tctct    180 gaccgattct ctggctccaa gtctggcacc tcagcctccc tggccatcag tgggctccag    240
tctgaggatg aggctgatta ttactgtgca gcatgggatg acagtgtgaa tggttatgtc    300
ttcggaactg ggaccaaggt caccgtccta ggt                                 333

<210> SEQ ID NO 30
<211> LENGTH: 117
<212> TYPE: PRT
<213> ORGANISM: Homo sapiens

<400> SEQUENCE: 30

Glu Val Gln Leu Val Gln Ser Gly Ala Glu Val Lys Lys Pro Gly Asp
1               5                   10                  15

```
Ser Val Lys Val Ser Cys Lys Ala Ser Gly Tyr Thr Phe Thr Arg Phe
            20                  25                  30

Gly Phe Ser Trp Val Arg Gln Ala Pro Gly Gln Gly Leu Glu Trp Met
        35                  40                  45

Gly Trp Ile Ser Val Asn Asn Gly Asn Thr Lys Tyr Ala Gln Lys Tyr
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Met Tyr Gly Arg Arg Asp Ser Trp Gly Gly Gly Thr Leu
            100                 105                 110

Val Thr Val Ser Ser
            115

<210> SEQ ID NO 31
<211> LENGTH: 351
<212> TYPE: DNA
<213> ORGANISM: Homo sapiens

<400> SEQUENCE: 31
gaggtccagc tggtgcagtc tggagctgag gtgaagaagc ctggggactc agtgaaggtc      60
tcctgcaagg cttctggtta cacctttacc agatttggtt tcagctgggt gcgacaggcc     120
cctggacaag ggcttgagtg gatgggatgg atcagcgtta ataatggtaa cacaaagtat     180
gcacagaagt accagggcag agtcaccatg accacagaca catccacgag cacagcctac     240
atggagctga ggagcctgag gtctgacgac actgccgtgt attactgtgc gcgctacatg     300
tacggtcgtc gtgattcttg gggtcaaggt actctggtga ccgtctcctc a              351

<210> SEQ ID NO 32
<211> LENGTH: 266
<212> TYPE: PRT
<213> ORGANISM: Homo sapiens

<400> SEQUENCE: 32

Gln Ala Val Leu Thr Gln Pro Pro Ser Met Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asn Asp Leu Leu Ser Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Val
                85                  90                  95

Asn Gly Tyr Val Phe Gly Thr Gly Thr Lys Val Thr Val Leu Gly Gly
            100                 105                 110

Ser Arg Gly Gly Gly Gly Ser Gly Gly Gly Gly Ser Gly Gly Gly Gly
            115                 120                 125

Ser Glu Val Gln Leu Val Gln Ser Gly Ala Glu Val Lys Lys Pro Gly
            130                 135                 140

Asp Ser Val Lys Val Ser Cys Lys Ala Ser Gly Tyr Thr Phe Thr Arg
145                 150                 155                 160
```

Phe Gly Phe Ser Trp Val Arg Gln Ala Pro Gly Gln Gly Leu Glu Trp
                165                 170                 175

Met Gly Trp Ile Ser Val Asn Asn Gly Asn Thr Lys Tyr Ala Gln Lys
            180                 185                 190

Tyr Gln Gly Arg Val Thr Met Thr Thr Asp Thr Ser Thr Ser Thr Ala
        195                 200                 205

Tyr Met Glu Leu Arg Ser Leu Arg Ser Asp Asp Thr Ala Val Tyr Tyr
    210                 215                 220

Cys Ala Arg Tyr Met Tyr Gly Arg Arg Asp Ser Trp Gly Gln Gly Thr
225                 230                 235                 240

Leu Val Thr Val Ser Ser Gly Gln His His His His His His Gly Ala
                245                 250                 255

Tyr Pro Tyr Asp Val Pro Asp Tyr Ala Ser
            260                 265

<210> SEQ ID NO 33
<211> LENGTH: 804
<212> TYPE: DNA
<213> ORGANISM: Homo sapiens

<400> SEQUENCE: 33
caggctgtgc tgactcagcc accctcgatg tctgaagccc caggcagag ggtcaccatc    60
tcctgttctg gaagcagctc caacatcgga ataatgctg taaactggta ccagcagctc   120
ccaggaaagg ctcccaaact cctcatctat tataatgatc tgctgtcctc agggtctct   180
gaccgattct ctggctccaa gtctggcacc tcagcctccc tggccatcag tgggctccag   240
tctgaggatg aggctgatta ttactgtgca gcatgggatg acagtgtgaa tggttatgtc   300
ttcggaactg ggaccaaggt caccgtccta ggtggttcta gaggtggtgg tggtagcggc   360
ggcggcggct ctggtggtgg tggatccgag gtccagctgg tgcagtctgg agctgaggtg   420
aagaagcctg ggactcagt gaaggtctcc tgcaaggctt ctggttacac ctttaccaga   480
tttggttca gctgggtgcg acaggcccct ggacaagggc ttgagtggat gggatggatc   540
agcgttaata atggtaacac aaagtatgca cagaagtacc agggcagagt caccatgacc   600
acagacacat ccacgagcac agcctacatg gagctgagga gcctgaggtc tgacgacact   660
gccgtgtatt actgtgcgcg ctacatgtac ggtcgtcgtg attcttgggg tcaaggtact   720
ctggtgaccg tctcctcagc cggccagcac catcaccatc accatggcgc ataccgtac   780
gacgttccgg actacgcttc ttag                                          804

<210> SEQ ID NO 34
<211> LENGTH: 6
<212> TYPE: PRT
<213> ORGANISM: Homo sapiens

<400> SEQUENCE: 34

Asn Ile Gly Ser Lys Ser
1               5

<210> SEQ ID NO 35
<211> LENGTH: 10
<212> TYPE: PRT
<213> ORGANISM: Homo sapiens

<400> SEQUENCE: 35

Gln Val Trp Asp Asn His Ser Asp Val Val
1               5                   10

<210> SEQ ID NO 36
<211> LENGTH: 8
<212> TYPE: PRT
<213> ORGANISM: Homo sapiens

<400> SEQUENCE: 36

Arg Asn Lys Phe Ser Ser Tyr Ala
1               5

<210> SEQ ID NO 37
<211> LENGTH: 8
<212> TYPE: PRT
<213> ORGANISM: Homo sapiens

<400> SEQUENCE: 37

Ile Ser Gly Ser Gly Gly Thr Thr
1               5

<210> SEQ ID NO 38
<211> LENGTH: 10
<212> TYPE: PRT
<213> ORGANISM: Homo sapiens

<400> SEQUENCE: 38

Ala Arg Trp Tyr Ser Ser Tyr Tyr Asp Val
1               5                   10

<210> SEQ ID NO 39
<211> LENGTH: 108
<212> TYPE: PRT
<213> ORGANISM: Homo sapiens

<400> SEQUENCE: 39

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asn His Ser Asp Val
                85                  90                  95

Val Phe Gly Gly Gly Thr Lys Leu Thr Val Leu Gly
            100                 105

<210> SEQ ID NO 40
<211> LENGTH: 324
<212> TYPE: DNA
<213> ORGANISM: Homo sapiens

<400> SEQUENCE: 40
cagtctgtgc tgactcagcc accctcagtg tcagtggccc caggaaagac ggccaggatt       60
acctgtgggg gaaacaacat tggaagtaaa agtgtgcact ggtaccagca gaagccaggc      120
caggcccctg tgctggtcat ctattatgat agcgaccggc cctcagggat ccctgagcga      180
ttctctggct ccaactctgg gaacacggcc accctgacca tcagcagggt cgaagccggg      240

```
gatgaggccg actattactg tcaggtctgg gataatcata gtgatgtggt attcggcgga    300
gggaccaagc tgaccgtcct aggt                                          324
```

<210> SEQ ID NO 41
<211> LENGTH: 120
<212> TYPE: PRT
<213> ORGANISM: Homo sapiens

<400> SEQUENCE: 41

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Arg Asn Lys Phe
            20                  25                  30

Ser Ser Tyr Ala Met Ser Trp Val Arg Gln Ala Pro Gly Lys Gly Leu
        35                  40                  45

Glu Trp Val Ser Gly Ile Ser Gly Ser Gly Gly Thr Thr Tyr Tyr Ala
    50                  55                  60

Asp Ser Val Lys Gly Arg Phe Thr Ile Ser Arg Asp Asn Ser Lys Asn
65                  70                  75                  80

Thr Gln Tyr Leu Gln Leu Asp Ser Leu Arg Ala Glu Asp Thr Ala Val
                85                  90                  95

Tyr Tyr Cys Ala Arg Trp Tyr Ser Ser Tyr Tyr Asp Val Trp Gly Gln
            100                 105                 110

Gly Thr Leu Val Thr Val Ser Ser
        115                 120
```

<210> SEQ ID NO 42
<211> LENGTH: 360
<212> TYPE: DNA
<213> ORGANISM: Homo sapiens

<400> SEQUENCE: 42

```
caggtgcagc tggtggagtc tgggggaggc ttggtacagc ctgggggtc cctgagactc     60 tcctgtgcag cctctggata cacccgtaac aaatttagca gctatgccat gagctgggtc    120
cgccaggctc cagggaaggg cctggaatgg gtctcaggta ttagtggtag tggtggtact    180
acatactatg cagactccgt gaagggccgg ttcaccatct ccagagacaa ttccaagaac    240
acgcagtatc tgcaattgga cagcctgaga gccgaggaca cggccgtata ttactgtgcg    300
cgctggtact cttcttacta cgatgtttgg ggtcaaggta ctctggtgac cgtctcctca    360
```

<210> SEQ ID NO 43
<211> LENGTH: 261
<212> TYPE: PRT
<213> ORGANISM: Homo sapiens

<400> SEQUENCE: 43

```
Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80
```

Asp Glu Ala Asp Tyr Tyr Cys Gln Val Trp Asp Asn His Ser Asp Val
            85                  90                  95

Val Phe Gly Gly Gly Thr Lys Leu Thr Val Leu Gly Gly Gly Gly Gly
        100                 105                 110

Ser Gly Gly Gly Gly Ser Gly Gly Gly Gly Ser Gln Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Tyr Thr Arg Asn Lys Phe Ser Ser Tyr Ala Met
145                 150                 155                 160

Ser Trp Val Arg Gln Ala Pro Gly Lys Gly Leu Glu Trp Val Ser Gly
                165                 170                 175

Ile Ser Gly Ser Gly Gly Thr Thr Tyr Tyr Ala Asp Ser Val Lys Gly
                180                 185                 190

Arg Phe Thr Ile Ser Arg Asp Asn Ser Lys Asn Thr Gln Tyr Leu Gln
                195                 200                 205

Leu Asp Ser Leu Arg Ala Glu Asp Thr Ala Val Tyr Tyr Cys Ala Arg
    210                 215                 220

Trp Tyr Ser Ser Tyr Tyr Asp Val Trp Gly Gln Gly Thr Leu Val Thr
225                 230                 235                 240

Val Ser Ser His His His His His His Gly Ala Tyr Pro Tyr Asp Val
                245                 250                 255

Pro Asp Tyr Ala Ser
            260

<210> SEQ ID NO 44
<211> LENGTH: 786
<212> TYPE: DNA
<213> ORGANISM: Homo sapiens

<400> SEQUENCE: 44

```
cagtctgtgc tgactcagcc accctcagtg tcagtggccc caggaaagac ggccaggatt        60
acctgtgggg gaaacaacat tggaagtaaa agtgtgcact ggtaccagca gaagccaggc       120
caggcccctg tgctggtcat ctattatgat agcgaccggc cctcaggat ccctgagcga        180
ttctctggct ccaactctgg gaacacggcc accctgacca tcagcagggt cgaagccggg       240
gatgaggccg actattactg tcaggtctgg gataatcata gtgatgtggt attcggcgga       300
gggaccaagc tgaccgtcct aggtggtggt ggtggtagcg gcggcggcgg ctctggtggt       360
ggtggatccc aggtgcagct ggtggagtct gggggaggct tggtacagcc tgggggtcc        420
ctgagactct cctgtgcagc ctctggatac acccgtaaca aatttagcag ctatgccatg       480
agctgggtcc gccaggctcc agggaagggc ctggaatggg tctcaggtat tagtggtagt       540
ggtggtacta catactatgc agactccgtg aagggccggt tcaccatctc cagagacaat       600
tccaagaaca cgcagtatct gcaattggac agcctgagag ccgaggacac ggccgtatat       660
tactgtgcgc gctggtactc ttcttactac gatgtttggg gtcaaggtac tctggtgacc       720
gtctcctcac accatcacca tcaccatggc gcatacccgt acgacgttcc ggactacgct       780
tcttag                                                                  786
```

<210> SEQ ID NO 45
<211> LENGTH: 10
<212> TYPE: PRT
<213> ORGANISM: Homo sapiens

<400> SEQUENCE: 45

```
<210> SEQ ID NO 46
<211> LENGTH: 8
<212> TYPE: PRT
<213> ORGANISM: Homo sapiens

<400> SEQUENCE: 46

Gly Phe Thr Phe Ser Ser Tyr Ala
1               5

<210> SEQ ID NO 47
<211> LENGTH: 8
<212> TYPE: PRT
<213> ORGANISM: Homo sapiens

<400> SEQUENCE: 47

Ile Ser Gly Ser Gly Gly Ser Thr
1               5

<210> SEQ ID NO 48
<211> LENGTH: 10
<212> TYPE: PRT
<213> ORGANISM: Homo sapiens

<400> SEQUENCE: 48

Ala Arg Asn Tyr Ile Ser Met Phe Asp Ser
1               5                   10

<210> SEQ ID NO 49
<211> LENGTH: 108
<212> TYPE: PRT
<213> ORGANISM: Homo sapiens

<400> SEQUENCE: 49
```

Gln Val Trp Asp Ser Ser Asp Tyr Val
1               5                   10

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp Tyr
                85                  90                  95

Val Phe Gly Ile Gly Thr Lys Val Thr Val Leu Gly
            100                 105

```
<210> SEQ ID NO 50
<211> LENGTH: 324
<212> TYPE: DNA
<213> ORGANISM: Homo sapiens

<400> SEQUENCE: 50
cagtctgtgc tgactcagcc accctcagtg tcagtggccc caggaaagac ggccaggatt     60
acctgtgggg gaaacaacat tggaagtaaa agtgtgcact ggtaccagca gaggccaggc    120
caggcccctg tgctggtcat ctattatgat agcgaccggc cctcaggat ccctgagcga    180
```

```
ttctctggct ccaactctgg gaacacggcc accctgacca tcagcagggt cgaagccggg    240
gatgaggccg actattactg tcaggtgtgg gatagtagta gtgattatgt cttcggaatt    300
gggaccaagg tcaccgtcct aggt                                           324
```

<210> SEQ ID NO 51
<211> LENGTH: 117
<212> TYPE: PRT
<213> ORGANISM: Homo sapiens

<400> SEQUENCE: 51

```
Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Tyr Ile Ser Met Phe Asp Ser Trp Gly Gln Gly Thr Leu
            100                 105                 110

Val Thr Val Ser Ser
        115
```

<210> SEQ ID NO 52
<211> LENGTH: 351
<212> TYPE: DNA
<213> ORGANISM: Homo sapiens

<400> SEQUENCE: 52

```
gaggtgcagc tggtggagtc tggaggaggc ttgatccagc ctgggggtc cctgagactc     60 tcctgtgcag cctctggatt cacctttagc agctatgcca tgagctgggt ccgccaggct   120
ccagggaagg gctggagtg gtctcagct attagtggta gtggtggtag cacatactac    180
gcagactccg tgaagggccg gttcaccatc tccagagaca attccaagaa cacgctgtat   240
ctgcaaatga acagcctgag agccgaggac acggccgtat attactgtgc gcgcaactac   300
atctctatgt tcgattcttg gggtcaaggt actctggtga ccgtctcctc a            351
```

<210> SEQ ID NO 53
<211> LENGTH: 258
<212> TYPE: PRT
<213> ORGANISM: Homo sapiens

<400> SEQUENCE: 53

```
Gln Ser Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60
```

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp Tyr
                 85                  90                  95

Val Phe Gly Ile Gly Thr Lys Val Thr Val Leu Gly Gly Gly Gly
            100                 105                 110

Ser Gly Gly Gly Gly Ser Gly Gly Gly Ser Glu Val Gln Leu Val
            115                 120                 125

Glu Ser Gly Gly Gly Leu Ile Gln Pro Gly Gly Ser Leu Arg Leu Ser
        130                 135                 140

Cys Ala Ala Ser Gly Phe Thr Phe Ser Ser Tyr Ala Met Ser Trp Val
145                 150                 155                 160

Arg Gln Ala Pro Gly Lys Gly Leu Glu Trp Val Ser Ala Ile Ser Gly
                165                 170                 175

Ser Gly Gly Ser Thr Tyr Tyr Ala Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Arg Ala Glu Asp Thr Ala Val Tyr Tyr Cys Ala Arg Asn Tyr Ile
    210                 215                 220

Ser Met Phe Asp Ser Trp Gly Gln Gly Thr Leu Val Thr Val Ser Ser
225                 230                 235                 240

His His His His His His Gly Ala Tyr Pro Tyr Asp Val Pro Asp Tyr
                245                 250                 255

Ala Ser

<210> SEQ ID NO 54
<211> LENGTH: 777
<212> TYPE: DNA
<213> ORGANISM: Homo sapiens

<400> SEQUENCE: 54
cagtctgtgc tgactcagcc accctcagtg tcagtggccc aggaaagac ggccaggatt        60 acctgtgggg gaaacaacat tggaagtaaa agtgtgcact ggtaccagca gaggccaggc      120
caggcccctg tgctggtcat ctattatgat agcgaccggc cctcagggat ccctgagcga      180
ttctctggct ccaactctgg gaacacggcc accctgacca tcagcagggt cgaagccggg      240
gatgaggccg actattactg tcaggtgtgg gatagtagta gtgattatgt cttcggaatt      300
gggaccaagg tcaccgtcct aggtggtggt ggtggtagcg gcggcggcgg ctctggtggt      360
ggtggatccg aggtgcagct ggtggagtct ggaggaggct tgatccagcc tgggggtcc      420 ctgagactct cctgtgcagc ctctggattc acctttagca gctatgccat gagctgggtc      480
cgccaggctc cagggaaggg gctggagtgg gtctcagcta ttagtggtag tggtggtagc      540
acatactacg cagactccgt gaagggccgg ttcaccatct ccagagacaa ttccaagaac      600
acgctgtatc tgcaaatgaa cagcctgaga gccgaggaca cggccgtata ttactgtgcg      660
cgcaactaca tctctatgtt cgattcttgg ggtcaaggta ctctggtgac cgtctcctca      720
caccatcacc atcaccatgg cgcatacccg tacgacgttc cggactacgc ttcttag       777

<210> SEQ ID NO 55
<211> LENGTH: 10
<212> TYPE: PRT
<213> ORGANISM: Homo sapiens

<400> SEQUENCE: 55
```

Gln Val Trp Asp Ser Ser Asp His Val
1               5                   10

<210> SEQ ID NO 56
<211> LENGTH: 10
<212> TYPE: PRT
<213> ORGANISM: Homo sapiens

<400> SEQUENCE: 56

Ala Arg Gly Tyr Ser Ser Tyr Tyr Asp Ala
1               5                   10

<210> SEQ ID NO 57
<211> LENGTH: 108
<212> TYPE: PRT
<213> ORGANISM: Homo sapiens

<400> SEQUENCE: 57

Gln Ala Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Val Phe Gly Thr Gly Thr Lys Val Thr Val Leu Gly
            100                 105

<210> SEQ ID NO 58
<211> LENGTH: 324
<212> TYPE: DNA
<213> ORGANISM: Homo sapiens

<400> SEQUENCE: 58
caggctgtgc tgactcagcc accctcagtg tcagtggccc caggaaagac ggccaggatt      60
acctgtgggg gaaacaacat tggaagtaaa agtgtgcact ggtaccagca gaagccaggc     120
caggcccctg tgctggtcat ctattatgat agcgaccggc cctcaggcat ccctgagcga     180
ttctctggct ccaactctgg gaacacggcc accctgacca tcagcagggt cgaagccggg     240
gatgaggccg actattactg tcaggtgtgg gatagtagta gtgatcatgt cttcggaact     300
gggaccaagg tcaccgtcct aggt                                             324

<210> SEQ ID NO 59
<211> LENGTH: 117
<212> TYPE: PRT
<213> ORGANISM: Homo sapiens

<400> SEQUENCE: 59

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                    35                  40                  45
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Ser Tyr Tyr Asp Ala Trp Gly Gln Gly Thr Leu
            100                 105                 110

Val Thr Val Ser Ser
            115

<210> SEQ ID NO 60
<211> LENGTH: 351
<212> TYPE: DNA
<213> ORGANISM: Homo sapiens

<400> SEQUENCE: 60
caggtgcagc tggtggagtc tgggggaggc ttggtacagc ctggggggtc cctgagactc       60
tcctgtgcag cctctggatt cacctttagc agctatgcca tgagctgggt ccgccaggct      120
ccagggaagg gctggagtg gtctcagct attagtggta gtggtggtag cacatactac        180
gcagactccg tgaagggccg gttcaccatc tccagagaca attccaagaa cacgctgtat      240
ctgcaaatga acagcctgag agccgaggac acggccgtat attactgtgc gcgcggttac      300
tcttcttact acgatgcttg gggtcaaggt actctggtga ccgtctcctc a               351

<210> SEQ ID NO 61
<211> LENGTH: 258
<212> TYPE: PRT
<213> ORGANISM: Homo sapiens

<400> SEQUENCE: 61

Gln Ala Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Phe Gly Thr Gly Thr Lys Val Thr Val Leu Gly Gly Gly Gly Gly
            100                 105                 110

Ser Gly Gly Gly Gly Ser Gly Gly Gly Gly Ser Gln Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Phe Ser Ser Tyr Ala Met Ser Trp Val
145                 150                 155                 160

Arg Gln Ala Pro Gly Lys Gly Leu Glu Trp Val Ser Ala Ile Ser Gly
                165                 170                 175

Ser Gly Gly Ser Thr Tyr Tyr Ala Asp Ser Val Lys Gly Arg Phe Thr
```

```
            180                 185                 190
Ile Ser Arg Asp Asn Ser Lys Asn Thr Leu Tyr Leu Gln Met Asn Ser
            195                 200                 205
Leu Arg Ala Glu Asp Thr Ala Val Tyr Tyr Cys Ala Arg Gly Tyr Ser
            210                 215                 220
Ser Tyr Tyr Asp Ala Trp Gly Gln Gly Thr Leu Val Thr Val Ser Ser
225                 230                 235                 240
His His His His His His Gly Ala Tyr Pro Tyr Asp Val Pro Asp Tyr
                    245                 250                 255
Ala Ser

<210> SEQ ID NO 62
<211> LENGTH: 777
<212> TYPE: DNA
<213> ORGANISM: Homo sapiens

<400> SEQUENCE: 62
caggctgtgc tgactcagcc accctcagtg tcagtggccc caggaaagac ggccaggatt      60
acctgtgggg gaaacaacat tggaagtaaa agtgtgcact ggtaccagca gaagccaggc     120
caggcccctg tgctggtcat ctattatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgatcatgt cttcggaact     300
gggaccaagg tcaccgtcct aggtggtggt ggtggtagcg gcggcggcgg ctctggtggt     360
ggtggatccc aggtgcagct ggtggagtct gggggaggct tggtacagcc tggggggtcc     420
ctgagactct cctgtgcagc ctctggattc acctttagca gctatgccat gagctgggtc     480
cgccaggctc cagggaaggg gctggagtgg gtctcagcta ttagtggtag tggtggtagc     540
acatactacg cagactccgt gaagggccgg ttcaccatct ccagagacaa ttccaagaac     600
acgctgtatc tgcaaatgaa cagcctgaga gccgaggaca cggccgtata ttactgtgcg     660
cgcggttact cttcttacta cgatgcttgg ggtcaaggta ctctggtgac cgtctcctca     720
caccatcacc atcaccatgg cgcatacccg tacgacgttc cggactacgc ttcttag       777

<210> SEQ ID NO 63
<211> LENGTH: 8
<212> TYPE: PRT
<213> ORGANISM: Homo sapiens

<400> SEQUENCE: 63

Arg Ser Asn Ile Gly Glu Asn Thr
1               5

<210> SEQ ID NO 64
<211> LENGTH: 11
<212> TYPE: PRT
<213> ORGANISM: Homo sapiens

<400> SEQUENCE: 64

Ala Ala Trp Asp Asp Arg Leu Asn Gly Tyr Val
1               5                   10

<210> SEQ ID NO 65
<211> LENGTH: 8
<212> TYPE: PRT
<213> ORGANISM: Homo sapiens

<400> SEQUENCE: 65
```

```
Gly Tyr Thr Phe Thr Asn Tyr Gly
1               5
```

<210> SEQ ID NO 66
<211> LENGTH: 8
<212> TYPE: PRT
<213> ORGANISM: Homo sapiens

<400> SEQUENCE: 66

```
Ile Gly Ala Gln Lys Gly Asp Thr
1               5
```

<210> SEQ ID NO 67
<211> LENGTH: 10
<212> TYPE: PRT
<213> ORGANISM: Homo sapiens

<400> SEQUENCE: 67

```
Ala Arg Ser Gln Gly Val Pro Phe Asp Ser
1               5                   10
```

<210> SEQ ID NO 68
<211> LENGTH: 111
<212> TYPE: PRT
<213> ORGANISM: Homo sapiens

<400> SEQUENCE: 68

```
Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Glu Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu His
65                  70                  75                  80

Ser Asp Asp Glu Ala Asp Tyr Phe Cys Ala Ala Trp Asp Asp Arg Leu
                85                  90                  95

Asn Gly Tyr Val Phe Gly Thr Gly Thr Lys Val Thr Val Leu Gly
            100                 105                 110
```

<210> SEQ ID NO 69
<211> LENGTH: 333
<212> TYPE: DNA
<213> ORGANISM: Homo sapiens

<400> SEQUENCE: 69

```
cagtctgtgt tgactcagcc accctcagcg tctgggaccc ccgggcagag agtcaccatc      60
tcttgttctg gaagcaggtc caacatcgga gaaatactg tcaactggta ccagcagctc     120
ccaggaacgg cccccaaact cctcatctac agtaataatc agcggccctc agggggtccct    180 gaccgattct ctggctccaa gtctggcacc tcagcctccc tggccatcag tgggcttcac    240
tctgacgatg aggctgacta ttttgtgca gcatgggatg accgcctcaa tggttatgtc    300
ttcggaactg ggaccaaggt caccgtccta ggt                                 333
```

<210> SEQ ID NO 70
<211> LENGTH: 117
<212> TYPE: PRT

<213> ORGANISM: Homo sapiens

<400> SEQUENCE: 70

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Phe Thr Trp Val Arg Gln Ala Pro Gly Gln Gly Leu Glu Trp Met
        35                  40                  45

Gly Trp Ile Gly Ala Gln Lys Gly Asp Thr Glu Tyr Ala Gln Lys Phe
    50                  55                  60

Gln Gly Arg Val Thr Met Thr Thr Asp Thr Ser Thr Ser Thr Val Tyr
65                  70                  75                  80

Leu Glu Leu Arg Ser Leu Arg Ser Asp Asp Thr Ala Val Tyr Tyr Cys
                85                  90                  95

Ala Arg Ser Gln Gly Val Pro Phe Asp Ser Trp Gly Gln Gly Thr Leu
            100                 105                 110

Val Thr Val Ser Ser
            115

<210> SEQ ID NO 71
<211> LENGTH: 351
<212> TYPE: DNA
<213> ORGANISM: Homo sapiens

<400> SEQUENCE: 71
caggtgcagc tggtgcaatc tggacctgag gtgaagaagc ctggggcctc ggtgaaggtc      60
tcctgcaagg cttctggtta cacctttacc aactatggtt tcacctgggt gcgacaggcc    120
cctggacaag gtcttgagtg gatgggatgg atcggcgctc aaaagggtga cacagagtat    180
gcacaaaaat tccagggcag agtcaccatg acgacagaca tccacgag cacagtctac      240 ttggagttga ggagcctgag gtctgacgac acggccgtgt attactgtgc gcgctctcag    300
ggtgttccgt tcgattcttg gggtcaaggt actctggtga ccgtctcctc a            351

<210> SEQ ID NO 72
<211> LENGTH: 261
<212> TYPE: PRT
<213> ORGANISM: Homo sapiens

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Glu Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu His
65                  70                  75                  80

Ser Asp Asp Glu Ala Asp Tyr Phe Cys Ala Ala Trp Asp Asp Arg Leu
                85                  90                  95

Asn Gly Tyr Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gln Val
            115                 120                 125

```
Gln Leu Val Gln Ser Gly Pro Glu Val Lys Lys Pro Gly Ala Ser Val
    130                 135                 140
Lys Val Ser Cys Lys Ala Ser Gly Tyr Thr Phe Thr Asn Tyr Gly Phe
145                 150                 155                 160
Thr Trp Val Arg Gln Ala Pro Gly Gln Gly Leu Glu Trp Met Gly Trp
                165                 170                 175
Ile Gly Ala Gln Lys Gly Asp Thr Glu Tyr Ala Gln Lys Phe Gln Gly
            180                 185                 190
Arg Val Thr Met Thr Thr Asp Thr Ser Thr Ser Thr Val Tyr Leu Glu
        195                 200                 205
Leu Arg Ser Leu Arg Ser Asp Asp Thr Ala Val Tyr Tyr Cys Ala Arg
    210                 215                 220
Ser Gln Gly Val Pro Phe Asp Ser Trp Gly Gln Gly Thr Leu Val Thr
225                 230                 235                 240
Val Ser Ser His His His His His His Gly Ala Tyr Pro Tyr Asp Val
                245                 250                 255
Pro Asp Tyr Ala Ser
            260
```

```
<210> SEQ ID NO 73
<211> LENGTH: 786
<212> TYPE: DNA
<213> ORGANISM: Homo sapiens

<400> SEQUENCE: 73
cagtctgtgt tgactcagcc accctcagcg tctgggaccc ccgggcagag agtcaccatc    60
tcttgttctg gaagcaggtc caacatcgga gaaaatactg tcaactggta ccagcagctc   120
ccaggaacgg ccccaaaact cctcatctac agtaataatc agcggccctc aggggtccct   180
gaccgattct ctggctccaa gtctggcacc tcagcctccc tggccatcag tgggcttcac   240
tctgacgatg aggctgacta ttttgtgca gcatgggatg accgcctcaa tggttatgtc   300
ttcggaactg ggaccaaggt caccgtccta ggtggtggtg gtggtagcgg cggcggcggc   360
tctggtggtg gtggatccca ggtgcagctg gtgcaatctg gacctgaggt gaagaagcct   420
ggggcctcgg tgaaggtctc ctgcaaggct tctggttaca cctttaccaa ctatggtttc   480
acctgggtgc gacaggcccc tggacaaggt cttgagtgga tgggatggat cggcgctcaa   540
aagggtgaca cagagtatgc acaaaaattc cagggcagag tcaccatgac gacagacaca   600
tccacgagca cagtctactt ggagttgagg agcctgaggt ctgacgacac ggccgtgtat   660
tactgtgcgc gctctcaggg tgttccgttc gattcttggg gtcaaggtac tctggtgacc   720
gtctcctcac accatcacca tcaccatggc gcatacccgt acgacgttcc ggactacgct   780
tcttag                                                              786
```

```
<210> SEQ ID NO 74
<211> LENGTH: 8
<212> TYPE: PRT
<213> ORGANISM: Homo sapiens

<400> SEQUENCE: 74

Arg Ser Asn Ile Gly Ser Asn Thr
1               5
```

```
<210> SEQ ID NO 75
<211> LENGTH: 11
<212> TYPE: PRT
```

<213> ORGANISM: Homo sapiens

<400> SEQUENCE: 75

Ala Thr Trp Asp Asp Ser Leu Asn Glu Tyr Val
1               5                   10

<210> SEQ ID NO 76
<211> LENGTH: 8
<212> TYPE: PRT
<213> ORGANISM: Homo sapiens

<400> SEQUENCE: 76

Gly Tyr Thr Phe Thr Arg Tyr Gly
1               5

<210> SEQ ID NO 77
<211> LENGTH: 8
<212> TYPE: PRT
<213> ORGANISM: Homo sapiens

<400> SEQUENCE: 77

Ile Ser Gly Tyr Asn Gly Asn Thr
1               5

<210> SEQ ID NO 78
<211> LENGTH: 10
<212> TYPE: PRT
<213> ORGANISM: Homo sapiens

<400> SEQUENCE: 78

Ala Arg His Gly Tyr Gly Tyr His Gly Asp
1               5                   10

<210> SEQ ID NO 79
<211> LENGTH: 111
<212> TYPE: PRT
<213> ORGANISM: Homo sapiens

<400> SEQUENCE: 79

Gln Ser Val Leu Thr Gln Pro Pro Ser Ala Ser Ala Thr Pro Gly Gln
1               5                   10                  15

Arg Gly Thr Ile Ser Cys Ser Gly Arg Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asn Asn Asn Leu Arg Pro Ser Gly Val Pro Asp Arg Phe Ser
    50                  55                  60

Gly Ser Lys Ser Gly Thr Ser Ala Ser Leu Ala Ile Arg Gly Leu Gln
65                  70                  75                  80

Ser Glu Asp Glu Ala Asp Tyr Tyr Cys Ala Thr Trp Asp Asp Ser Leu
                85                  90                  95

Asn Glu Tyr Val Phe Gly Thr Gly Thr Lys Val Thr Val Leu Gly
                100                 105                 110

<210> SEQ ID NO 80
<211> LENGTH: 333
<212> TYPE: DNA
<213> ORGANISM: Homo sapiens

<400> SEQUENCE: 80
cagtctgtgt tgactcagcc accctcagcg tctgcgaccc ccgggcagag gggcaccatt      60

```
tcgtgttctg gaggcaggtc caacatcgga agtaacactg ttaactggta ccagcagctc    120
ccaggaacgg ccccaaact cctcatctat aataataatc tgcggcctc agggtccct      180 gaccgattct ctggctccaa gtctggcacc tcagcctccc tggccatcag ggggctccag    240
tctgaggatg aggctgatta ttactgtgca acatgggatg acagcctgaa tgaatatgtc    300
ttcggaactg ggaccaaggt caccgtccta ggt                                  333
```

<210> SEQ ID NO 81
<211> LENGTH: 117
<212> TYPE: PRT
<213> ORGANISM: Homo sapiens

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Gly Tyr Gly Tyr His Gly Asp Trp Gly Gln Gly Thr Leu
            100                 105                 110

Val Thr Val Ser Ser
        115

<210> SEQ ID NO 82
<211> LENGTH: 351
<212> TYPE: DNA
<213> ORGANISM: Homo sapiens

<400> SEQUENCE: 82

```
caggtgcagc tggtgcaatc tggagctgag gtgaagaagc ctggggcctc agtgaaggtc    60
tcctgcaagg cttctggtta cacctttacc agatatggta tcagctgggt gcgacaggcc    120
cctggacaag gcttgagtg gatgggatgg atcagcggtt acaacggtaa cacaaactat    180
gcacagaagc tccagggcag agtcaccatg accacagaca catccacgag cacagcctac    240
atggagctga ggagcctgag gtctgacgac acggccgtgt attactgtgc gcgccatggt    300
tacggttacc atggtgattg gggtcaaggt actctggtga ccgtctcctc a              351
```

<210> SEQ ID NO 83
<211> LENGTH: 261
<212> TYPE: PRT
<213> ORGANISM: Homo sapiens

<400> SEQUENCE: 83

Gln Ser Val Leu Thr Gln Pro Pro Ser Ala Ser Ala Thr Pro Gly Gln
1               5                   10                  15

Arg Gly Thr Ile Ser Cys Ser Gly Gly Arg Ser Asn Ile Gly Ser Asn
            20                  25                  30

Thr Val Asn Trp Tyr Gln Gln Leu Pro Gly Thr Ala Pro Lys Leu Leu
        35                  40                  45

```
Ile Tyr Asn Asn Asn Leu Arg Pro Ser Gly Val Pro Asp Arg Phe Ser
 50                  55                  60
Gly Ser Lys Ser Gly Thr Ser Ala Ser Leu Ala Ile Arg Gly Leu Gln
 65                  70                  75                  80
Ser Glu Asp Glu Ala Asp Tyr Tyr Cys Ala Thr Trp Asp Asp Ser Leu
                 85                  90                  95
Asn Glu Tyr Val Phe Gly Thr Gly Thr Lys Val Thr Val Leu Gly Gly
            100                 105                 110
Gly Gly Gly Ser Gly Gly Gly Ser Gly Gly Gly Ser Gln Val
            115                 120                 125
Gln Leu Val Gln Ser Gly Ala Glu Val Lys Lys Pro Gly Ala Ser Val
130                 135                 140
Lys Val Ser Cys Lys Ala Ser Gly Tyr Thr Phe Thr Arg Tyr Gly Ile
145                 150                 155                 160
Ser Trp Val Arg Gln Ala Pro Gly Gln Gly Leu Glu Trp Met Gly Trp
                165                 170                 175
Ile Ser Gly Tyr Asn Gly Asn Thr Asn Tyr Ala Gln Lys Leu Gln Gly
            180                 185                 190
Arg Val Thr Met Thr Thr Asp Thr Ser Thr Ser Thr Ala Tyr Met Glu
            195                 200                 205
Leu Arg Ser Leu Arg Ser Asp Asp Thr Ala Val Tyr Tyr Cys Ala Arg
210                 215                 220
His Gly Tyr Gly Tyr His Gly Asp Trp Gly Gln Gly Thr Leu Val Thr
225                 230                 235                 240
Val Ser Ser His His His His His Gly Ala Tyr Pro Tyr Asp Val
                245                 250                 255
Pro Asp Tyr Ala Ser
            260
```

<210> SEQ ID NO 84
<211> LENGTH: 786
<212> TYPE: DNA
<213> ORGANISM: Homo sapiens

<400> SEQUENCE: 84

```
cagtctgtgt tgactcagcc accctcagcg tctgcgaccc ccgggcagag gggcaccatt      60
tcgtgttctg gaggcaggtc caacatcgga agtaacactg ttaactgtta ccagcagctc     120
ccaggaacgg cccccaaact cctcatctat aataataatc tgcggccctc aggggtccct     180
gaccgattct ctggctccaa gtctggcacc tcagcctccc tggccatcag ggggctccag     240
tctgaggatg aggctgatta ttactgtgca acatgggatg acagcctgaa tgaatatgtc     300
ttcggaactg ggaccaaggt caccgtccta ggtggtggtg gtggtagcgg cggcggcggc     360
tctggtggtg gtggatccca ggtgcagctg gtgcaatctg gagctgaggt gaagaagcct     420
ggggcctcag tgaaggtctc ctgcaaggct tctggttaca cctttaccag atatggtatc     480
agctgggtgc gacaggcccc tggacaaggg cttgagtgga tggatggat cagcggttac     540
aacggtaaca caaactatgc acagaagctc cagggcagag tcaccatgac cacagacaca     600
tccacgagca gcctacat ggagctgagg agcctgaggt ctgacgacac ggccgtgtat     660
tactgtgcgc gccatggtta cggttaccat ggtgattggg gtcaaggtac tctggtgacc     720
gtctcctcac accatcacca tcaccatggc gcatacccgt acgacgttcc ggactacgct     780
tcttag                                                                 786
```

<210> SEQ ID NO 85
<211> LENGTH: 9
<212> TYPE: PRT
<213> ORGANISM: Homo sapiens

<400> SEQUENCE: 85

Ser Ser Asn Ile Gly Ala Gly Tyr Val
1               5

<210> SEQ ID NO 86
<211> LENGTH: 11
<212> TYPE: PRT
<213> ORGANISM: Homo sapiens

<400> SEQUENCE: 86

Gln Ser Tyr Asp Ser Ser Leu Ser Gly Trp Val
1               5                   10

<210> SEQ ID NO 87
<211> LENGTH: 8
<212> TYPE: PRT
<213> ORGANISM: Homo sapiens

<400> SEQUENCE: 87

Gly Phe Thr Phe Lys Asp Tyr Tyr
1               5

<210> SEQ ID NO 88
<211> LENGTH: 8
<212> TYPE: PRT
<213> ORGANISM: Homo sapiens

<400> SEQUENCE: 88

Ile Ser Thr Ser Gly Asn Ser Val
1               5

<210> SEQ ID NO 89
<211> LENGTH: 11
<212> TYPE: PRT
<213> ORGANISM: Homo sapiens

<400> SEQUENCE: 89

Ala Arg Ser Pro Gly His Ser Asp Tyr Asp Ser
1               5                   10

<210> SEQ ID NO 90
<211> LENGTH: 112
<212> TYPE: PRT
<213> ORGANISM: Homo sapiens

<400> SEQUENCE: 90

Gln Ser Val Leu Thr Gln Pro Pro Ser Val Ser Ala Pro Gly Gln
1               5                   10                  15

Arg Val Thr Ile Ser Cys Thr Gly Ser Ser Ser Asn Ile Gly Ala Gly
                20                  25                  30

Tyr Val Val Gln Trp Tyr Gln Gln Leu Pro Gly Thr Ala Pro Lys Leu
            35                  40                  45

Leu Ile Tyr His Asn Asn Asp Arg Pro Ser Gly Val Pro Tyr Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

-continued

Leu Ser Gly Trp Val Phe Gly Gly Gly Thr Lys Leu Thr Val Leu Gly
        100                 105                 110

<210> SEQ ID NO 91
<211> LENGTH: 336
<212> TYPE: DNA
<213> ORGANISM: Homo sapiens

<400> SEQUENCE: 91
cagtctgtgc tgacgcagcc gccctcagtg tctggggccc cagggcagag ggtcaccatc      60
tcctgtactg ggagcagctc caacatcggg gcaggttatg ttgtacagtg gtatcagcag     120
cttccaggaa cagcccccaa actcctcatc tatcataaca acgatcggcc ctcaggggtc     180
ccttaccgat tctctggctc caagtctggc acctcagcct ccctggccat cactgggctc     240
caggctgagg atgaggctga ttattactgc agtcctatg acagcagcct gagtggttgg     300
gtgttcggcg agggaccaa gctgaccgtc ctaggt                               336

<210> SEQ ID NO 92
<211> LENGTH: 118
<212> TYPE: PRT
<213> ORGANISM: Homo sapiens

<400> SEQUENCE: 92

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asp Tyr
            20                  25                  30

Tyr Met Asn Trp Ile Arg Gln Ala Pro Gly Lys Gly Leu Glu Trp Ile
        35                  40                  45

Ser His Ile Ser Thr Ser Gly Asn Ser Val Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Gly His Ser Asp Tyr Asp Ser Trp Gly Gln Gly Thr
            100                 105                 110

Leu Val Thr Val Ser Ser
        115

<210> SEQ ID NO 93
<211> LENGTH: 354
<212> TYPE: DNA
<213> ORGANISM: Homo sapiens

<400> SEQUENCE: 93
gaggtgcagc tggtggagtc tgggggaggc ctagtcaagc ctggagggtc cctgagactc      60
tcctgtgcag cctctggatt caccttaaa gactactaca tgaactggat ccgccaggct     120
ccagggaagg gcctggagtg gatttcacac attagtacca gcggtaatag tgtagattat     180
gcagactctg tcaagggccg gttcaccatc tccagggaca acgccaagaa ttcactgtac     240
ctgcaaatga acagcctgag agccgaggac acggccgtat attactgtgc gcgctctccg     300
ggtcattctg actacgattc ttggggtcaa ggtactctgg tgaccgtctc ctca           354

<210> SEQ ID NO 94
<211> LENGTH: 263

<212> TYPE: PRT
<213> ORGANISM: Homo sapiens

<400> SEQUENCE: 94

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Val Val Gln Trp Tyr Gln Gln Leu Pro Gly Thr Ala Pro Lys Leu
        35                  40                  45

Leu Ile Tyr His Asn Asn Asp Arg Pro Ser Gly Val Pro Tyr Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu Gly
            100                 105                 110

Gly Gly Gly Gly Ser Gly Gly Gly Ser Gly Gly Gly Gly Ser Glu
        115                 120                 125

Val Gln Leu Val Glu Ser Gly Gly Gly Leu Val Lys Pro Gly Gly Ser
    130                 135                 140

Leu Arg Leu Ser Cys Ala Ala Ser Gly Phe Thr Phe Lys Asp Tyr Tyr
145                 150                 155                 160

Met Asn Trp Ile Arg Gln Ala Pro Gly Lys Gly Leu Glu Trp Ile Ser
                165                 170                 175

His Ile Ser Thr Ser Gly Asn Ser Val Asp Tyr Ala Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Ser Pro Gly His Ser Asp Tyr Asp Ser Trp Gly Gln Gly Thr Leu
225                 230                 235                 240

Val Thr Val Ser Ser His His His His His Gly Ala Tyr Pro Tyr
                245                 250                 255

Asp Val Pro Asp Tyr Ala Ser
            260

<210> SEQ ID NO 95
<211> LENGTH: 792
<212> TYPE: DNA
<213> ORGANISM: Homo sapiens

<400> SEQUENCE: 95
cagtctgtgc tgacgcagcc gccctcagtg tctggggccc cagggcagag ggtcaccatc        60
tcctgtactg ggagcagctc caacatcggg gcaggttatg ttgtacagtg gtatcagcag       120
cttccaggaa cagcccccaa actcctcatc tatcataaca acgatcggcc ctcaggggtc       180
ccttaccgat tctctggctc caagtctggc acctcagcct ccctggccat cactgggctc       240
caggctgagg atgaggctga ttattactgc cagtcctatg acagcagcct gagtggttgg       300
gtgttcggcg gagggaccaa gctgaccgtc ctaggtggtg gtggtggtag cggcggcggc       360
ggctctggtg gtggtggatc cgaggtgcag ctggtggagt ctggggagg cctagtcaag       420 cctggagggt ccctgagact ctcctgtgca gcctctggat tcacctttaa agactactac       480

```
atgaactgga tccgccaggc tccagggaag ggcctggagt ggatttcaca cattagtacc    540
agcggtaata gtgtagatta tgcagactct gtcaagggcc ggttcaccat ctccagggac    600
aacgccaaga attcactgta cctgcaaatg aacagcctga gagccgagga cacggccgta    660
tattactgtg cgcgctctcc gggtcattct gactacgatt cttggggtca aggtactctg    720
gtgaccgtct cctcacacca tcaccatcac catggcgcat acccgtacga cgttccggac    780
tacgcttctt ag                                                        792
```

<210> SEQ ID NO 96
<211> LENGTH: 6
<212> TYPE: PRT
<213> ORGANISM: Homo sapiens

<400> SEQUENCE: 96

Asn Ile Gly Asp Lys Ser
1               5

<210> SEQ ID NO 97
<211> LENGTH: 13
<212> TYPE: PRT
<213> ORGANISM: Homo sapiens

<400> SEQUENCE: 97

Gln Val Trp Ala Ser Gly Thr Asp His Pro Tyr Val Ile
1               5                   10

<210> SEQ ID NO 98
<211> LENGTH: 10
<212> TYPE: PRT
<213> ORGANISM: Homo sapiens

<400> SEQUENCE: 98

Ala Arg Met Tyr Gly Ser Tyr Thr Asp Met
1               5                   10

<210> SEQ ID NO 99
<211> LENGTH: 111
<212> TYPE: PRT
<213> ORGANISM: Homo sapiens

<400> SEQUENCE: 99

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Asp Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ala Ser Gly Thr Asp His
                85                  90                  95

Pro Tyr Val Ile Phe Gly Gly Gly Thr Lys Val Thr Val Leu Gly
            100                 105                 110

<210> SEQ ID NO 100
<211> LENGTH: 333
<212> TYPE: DNA

<213> ORGANISM: Homo sapiens

<400> SEQUENCE: 100

```
tcctatgtgc tgactcagcc accctcagtg tcagtggccc caggaaagac ggccaggatt    60
acctgtgggg gaaacaacat tggagataaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gacgaggccg actattactg tcaggtgtgg gctagtggta ctgatcatcc ctatgtgata   300
ttcggcggag ggaccaaggt caccgtccta ggt                                333
```

<210> SEQ ID NO 101
<211> LENGTH: 117
<212> TYPE: PRT
<213> ORGANISM: Homo sapiens

<400> SEQUENCE: 101

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Tyr Gly Ser Tyr Thr Asp Met Trp Gly Gln Gly Thr Leu
            100                 105                 110

Val Thr Val Ser Ser
        115
```

<210> SEQ ID NO 102
<211> LENGTH: 351
<212> TYPE: DNA
<213> ORGANISM: Homo sapiens

<400> SEQUENCE: 102

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg gtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gcgcatgtac   300
ggttcttaca ctgatatgtg gggtcaaggt actctggtga ccgtctcctc a             351
```

<210> SEQ ID NO 103
<211> LENGTH: 261
<212> TYPE: PRT
<213> ORGANISM: Homo sapiens

<400> SEQUENCE: 103

```
Ser Tyr Val Leu Thr Gln Pro Pro Ser Val Ser Val Ala Pro Gly Lys
1               5                   10                  15
```

Thr Ala Arg Ile Thr Cys Gly Gly Asn Asn Ile Gly Asp Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ala Ser Gly Thr Asp His
                85                  90                  95

Pro Tyr Val Ile Phe Gly Gly Gly Thr Lys Val Thr Val Leu Gly Gly
            100                 105                 110

Gly Gly Gly Ser Gly Gly Gly Ser Gly Gly Gly Ser Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Phe Ser Ser Tyr Ala Met
145                 150                 155                 160

Ser Trp Val Arg Gln Ala Pro Gly Lys Gly Leu Glu Trp Val Ser Ala
                165                 170                 175

Ile Ser Gly Ser Gly Gly Ser Thr Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Arg
210                 215                 220

Met Tyr Gly Ser Tyr Thr Asp Met Trp Gly Gln Gly Thr Leu Val Thr
225                 230                 235                 240

Val Ser Ser His His His His His His Gly Ala Tyr Pro Tyr Asp Val
                245                 250                 255

Pro Asp Tyr Ala Ser
            260

<210> SEQ ID NO 104
<211> LENGTH: 786
<212> TYPE: DNA
<213> ORGANISM: Homo sapiens

<400> SEQUENCE: 104
tcctatgtgc tgactcagcc accctcagtg tcagtggccc caggaaagac ggccaggatt      60
acctgtgggg gaaacaacat tggagataaa agtgtgcact ggtaccagca gaagccaggc     120
caggcccctg tgctggtcat ctattatgat agcgaccggc cctcagggat ccctgagcga     180
ttctctggct ccaactctgg gaacacggcc accctgacca tcagcagggt cgaagccggg     240
gacgaggccg actattactg tcaggtgtgg gctagtggta ctgatcatcc ctatgtgata     300
ttcggcggag ggaccaaggt caccgtccta ggtggtggtg gtggtagcgg cggcggcggc     360
tctggtggtg gtggatccga ggtgcagctg gtggagtctg ggggaggctt ggtacagcct     420
ggggggtccc tgagactctc ctgtgcagcc tctggattca cctttagcag ctatgccatg     480
agctgggtcc gccaggctcc agggaagggg ctggagtggg tctcagctat tagtggtagt     540
ggtggtagca catactacgc agactccgtg aagggccggt tcaccatctc cagagacaat     600
tccaagaaca cgctgtatct gcaaatgaac agcctgagag ccgaggacac ggccgtatat     660
tactgtgcgc gcatgtacgg ttcttacact gatatgtggg gtcaaggtac tctggtgacc     720

```
gtctcctcac accatcacca tcaccatggc gcataccccgt acgacgttcc ggactacgct    780
tcttag                                                                786
```

<210> SEQ ID NO 105
<211> LENGTH: 8
<212> TYPE: PRT
<213> ORGANISM: Homo sapiens

<400> SEQUENCE: 105

```
Ser Ser Asn Ile Gly Tyr Asn Tyr
1               5
```

<210> SEQ ID NO 106
<211> LENGTH: 11
<212> TYPE: PRT
<213> ORGANISM: Homo sapiens

<400> SEQUENCE: 106

```
Thr Ser Trp Asp Asp Ser Leu Ser Gly Tyr Val
1               5                   10
```

<210> SEQ ID NO 107
<211> LENGTH: 8
<212> TYPE: PRT
<213> ORGANISM: Homo sapiens

<400> SEQUENCE: 107

```
Gly Asn Ala Phe Thr Asn Phe Tyr
1               5
```

<210> SEQ ID NO 108
<211> LENGTH: 9
<212> TYPE: PRT
<213> ORGANISM: Homo sapiens

<400> SEQUENCE: 108

```
Ile Asn Pro Ser Gly Thr Asp Leu Thr
1               5
```

<210> SEQ ID NO 109
<211> LENGTH: 13
<212> TYPE: PRT
<213> ORGANISM: Homo sapiens

<400> SEQUENCE: 109

```
Ala Arg Gln Tyr Ala Tyr Gly Tyr Ser Gly Phe Asp Met
1               5                   10
```

<210> SEQ ID NO 110
<211> LENGTH: 111
<212> TYPE: PRT
<213> ORGANISM: Homo sapiens

<400> SEQUENCE: 110

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Tyr Asn
            20                  25                  30

Tyr Val Tyr Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60
```

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Thr Ser Trp Asp Asp Ser Leu
                85                  90                  95

Ser Gly Tyr Val Phe Gly Pro Gly Thr Lys Val Thr Val Leu Gly
            100                 105                 110

<210> SEQ ID NO 111
<211> LENGTH: 333
<212> TYPE: DNA
<213> ORGANISM: Homo sapiens

<400> SEQUENCE: 111
cagtctgtgc tgactcagcc accctcagcg tctgggaccc ccggggcagag ggtcaccatc    60 tcttgttctg gaagcagctc caacatcgga tataattatg tatactggta ccagcagctc   120
ccaggaacgg cccccaaact cctcatctct agaaataatc agcggccctc agggtccct    180 gaccgattct ctggctccaa gtctggcacc tcagcctccc tggccatcag tgggctccgg   240
tccgaggatg aggctgacta ttactgtaca tcgtgggatg acagcctgag tggttatgtc   300
ttcggacctg ggaccaaggt caccgtccta ggt                                333

<210> SEQ ID NO 112
<211> LENGTH: 121
<212> TYPE: PRT
<213> ORGANISM: Homo sapiens

<400> SEQUENCE: 112

Glu Val Gln Leu Val Gln Ser Gly Ala Glu Val Lys Lys Pro Gly Ala
1               5                   10                  15

Ser Val Lys Val Ser Cys Lys Ala Ser Gly Asn Ala Phe Thr Asn Phe
            20                  25                  30

Tyr Ile His Trp Val Arg Gln Ala Pro Gly Gln Gly Leu Glu Trp Met
        35                  40                  45

Gly Leu Ile Asn Pro Ser Gly Thr Asp Leu Thr Arg Tyr Ala Gln Lys
    50                  55                  60

Phe Gln Gly Arg Val Thr Met Thr Arg Asp Thr Pro Thr Ser Thr Val
65                  70                  75                  80

Tyr Met Glu Leu Ser Ser Leu Arg Ser Asp Asp Thr Ala Val Tyr Tyr
                85                  90                  95

Cys Ala Arg Gln Tyr Ala Tyr Gly Tyr Ser Gly Phe Asp Met Trp Gly
            100                 105                 110

Gln Gly Thr Leu Val Thr Val Ser Ser
        115                 120

<210> SEQ ID NO 113
<211> LENGTH: 363
<212> TYPE: DNA
<213> ORGANISM: Homo sapiens

<400> SEQUENCE: 113
gaagtgcagc tggtgcagtc tggggctgag gtgaagaagc ctggggcctc agtgaaggtt    60
tcctgcaagg catctggaaa cgccttcacc aacttctata cactgggt gcgacaggcc    120 cctggacaag gcttgagtg gatgggatta atcaaccctg gtggtactga cctcacaagg   180
tacgcacaga agttccaggg cagagtcacc atgaccaggg acacgccac gagcacagtc   240 tacatggagc tgagcagcct gaggtctgac gacacggctg tgtattactg tgcgcgccag   300

```
tacgcttacg gttactctgg tttcgatatg tggggtcaag gtactctggt gaccgtctcc    360
tca                                                                  363
```

<210> SEQ ID NO 114
<211> LENGTH: 265
<212> TYPE: PRT
<213> ORGANISM: Homo sapiens

<400> SEQUENCE: 114

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Tyr Asn
            20                  25                  30

Tyr Val Tyr Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Thr Ser Trp Asp Asp Ser Leu
                85                  90                  95

Ser Gly Tyr Val Phe Gly Pro Gly Thr Lys Val Thr Leu Gly Gly
            100                 105                 110

Gly Gly Gly Ser Gly Gly Gly Ser Gly Gly Gly Ser Glu Val
            115                 120                 125

Gln Leu Val Gln Ser Gly Ala Glu Val Lys Lys Pro Gly Ala Ser Val
    130                 135                 140

Lys Val Ser Cys Lys Ala Ser Gly Asn Ala Phe Thr Asn Phe Tyr Ile
145                 150                 155                 160

His Trp Val Arg Gln Ala Pro Gly Gln Gly Leu Glu Trp Met Gly Leu
                165                 170                 175

Ile Asn Pro Ser Gly Thr Asp Leu Thr Arg Tyr Ala Gln Lys Phe Gln
            180                 185                 190

Gly Arg Val Thr Met Thr Arg Asp Thr Pro Thr Ser Thr Val Tyr Met
        195                 200                 205

Glu Leu Ser Ser Leu Arg Ser Asp Asp Thr Ala Val Tyr Tyr Cys Ala
    210                 215                 220

Arg Gln Tyr Ala Tyr Gly Tyr Ser Gly Phe Asp Met Trp Gly Gln Gly
225                 230                 235                 240

Thr Leu Val Thr Val Ser Ser His His His His His Gly Ala Tyr
                245                 250                 255

Pro Tyr Asp Val Pro Asp Tyr Ala Ser
            260                 265
```

<210> SEQ ID NO 115
<211> LENGTH: 798
<212> TYPE: DNA
<213> ORGANISM: Homo sapiens

<400> SEQUENCE: 115

```
cagtctgtgc tgactcagcc accctcagcg tctgggaccc ccgggcagag ggtcaccatc     60
tcttgttctg gaagcagctc caacatcgga tataattatg tatactggta ccagcagctc    120
ccaggaacgg ccccaaaact cctcatctct agaataatc agcggccctc aggggtccct     180
gaccgattct ctggctccaa gtctggcacc tcagcctccc tggccatcag tgggctccgg    240
```

```
tccgaggatg aggctgacta ttactgtaca tcgtgggatg acagcctgag tggttatgtc    300
ttcggacctg ggaccaaggt caccgtccta ggtggtggtg gtggtagcgg cggcggcggc    360
tctggtggtg gtggatccga agtgcagctg gtgcagtctg gggctgaggt gaagaagcct    420
ggggcctcag tgaaggtttc ctgcaaggca tctggaaacg ccttcaccaa cttctatata    480
cactgggtgc gacaggcccc tggacaaggg cttgagtgga tgggattaat caaccctagt    540
ggtactgacc tcacaaggta cgcacagaag ttccagggca gagtcaccat gaccagggac    600
acgcccacga gcacagtcta catggagctg agcagcctga ggtctgacga cacggctgtg    660
tattactgtg cgcgccagta cgcttacggt tactctggtt tcgatatgtg gggtcaaggt    720
actctggtga ccgtctcctc acaccatcac catcaccatg gcgcataccc gtacgacgtt    780
ccggactacg cttcttag                                                  798
```

<210> SEQ ID NO 116
<211> LENGTH: 6
<212> TYPE: PRT
<213> ORGANISM: Homo sapiens

<400> SEQUENCE: 116

Gln Ser Val Ser Asn Trp
1               5

<210> SEQ ID NO 117
<211> LENGTH: 9
<212> TYPE: PRT
<213> ORGANISM: Homo sapiens

<400> SEQUENCE: 117

Gln Gln Ser Tyr Ser Thr Pro Ile Thr
1               5

<210> SEQ ID NO 118
<211> LENGTH: 8
<212> TYPE: PRT
<213> ORGANISM: Homo sapiens

<400> SEQUENCE: 118

Gly Tyr Thr Phe Thr Ser Tyr Tyr
1               5

<210> SEQ ID NO 119
<211> LENGTH: 8
<212> TYPE: PRT
<213> ORGANISM: Homo sapiens

<400> SEQUENCE: 119

Ile Asn Pro Asn Thr Gly Gly Ser
1               5

<210> SEQ ID NO 120
<211> LENGTH: 9
<212> TYPE: PRT
<213> ORGANISM: Homo sapiens

<400> SEQUENCE: 120

Ala Arg Gly Asp Val Thr Tyr Asp Glu
1               5

<210> SEQ ID NO 121
<211> LENGTH: 108

-continued

<212> TYPE: PRT
<213> ORGANISM: Homo sapiens

<400> SEQUENCE: 121

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Val Ser Asn Trp
            20                  25                  30

Leu Ala Trp Tyr Gln Leu Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gly Gly Thr Lys Val Glu Ile Lys Arg
            100                 105

<210> SEQ ID NO 122
<211> LENGTH: 324
<212> TYPE: DNA
<213> ORGANISM: Homo sapiens

<400> SEQUENCE: 122
gacatccaga tgacccagtc tccatcttcc gtgtctgcat ctgtaggaga cagagtcacc     60
atcacttgtc gggcgagtca gagtgttagc aactggttag cctggtatca actgaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgatcac cttcggcgga    300
gggaccaagg tggagatcaa acgt                                           324

<210> SEQ ID NO 123
<211> LENGTH: 116
<212> TYPE: PRT
<213> ORGANISM: Homo sapiens

<400> SEQUENCE: 123

Gln Val Gln Leu Val Gln Ser Gly Ala Glu Val Lys Lys Pro Gly Thr
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Asn Pro Asn Thr Gly Gly Ser Asn Phe Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Gly Asp Val Thr Tyr Asp Glu Trp Gly Gln Gly Thr Leu Val
            100                 105                 110

Thr Val Ser Ser
        115

-continued

<210> SEQ ID NO 124
<211> LENGTH: 348
<212> TYPE: DNA
<213> ORGANISM: Homo sapiens

<400> SEQUENCE: 124
caggtccagc tggtacagtc tggggctgag gtgaagaagc ctgggacctc agtgaaggtc      60
tcctgcaagg cttctggata caccttcacc tcctactata tacactgggt gcgacaggcc     120
cctggacaag gcttgagtg gatgggatgg atcaaccctaacactggtgg ctcaaacttt      180 gcacagaagt ttcagggcag ggtcaccatg accagggaca cgtccatcag cacagcctac     240
atggagctga acaggctgag gtctgacgac acggccgtgt attactgtgc gcgcggtgac     300
gttacttacg atgaatgggg tcaaggtact ctggtgaccg tctcctca                 348

<210> SEQ ID NO 125
<211> LENGTH: 257
<212> TYPE: PRT
<213> ORGANISM: Homo sapiens

<400> SEQUENCE: 125

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Val Ser Asn Trp
            20                  25                  30

Leu Ala Trp Tyr Gln Leu Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Thr Ser Val Lys Val Ser
    130                 135                 140

Cys Lys Ala Ser Gly Tyr Thr Phe Thr Ser Tyr Tyr Ile His Trp Val
145                 150                 155                 160

Arg Gln Ala Pro Gly Gln Gly Leu Glu Trp Met Gly Trp Ile Asn Pro
                165                 170                 175

Asn Thr Gly Gly Ser Asn Phe Ala Gln Lys Phe Gln Gly Arg Val Thr
            180                 185                 190

Met Thr Arg Asp Thr Ser Ile Ser Thr Ala Tyr Met Glu Leu Asn Arg
        195                 200                 205

Leu Arg Ser Asp Asp Thr Ala Val Tyr Tyr Cys Ala Arg Gly Asp Val
    210                 215                 220

Thr Tyr Asp Glu Trp Gly Gln Gly Thr Leu Val Thr Val Ser Ser His
225                 230                 235                 240

His His His His Gly Ala Tyr Pro Tyr Asp Val Pro Asp Tyr Ala
                245                 250                 255

Ser

<210> SEQ ID NO 126

```
<211> LENGTH: 774
<212> TYPE: DNA
<213> ORGANISM: Homo sapiens

<400> SEQUENCE: 126
gacatccaga tgacccagtc tccatcttcc gtgtctgcat ctgtaggaga cagagtcacc    60
atcacttgtc gggcgagtca gagtgttagc aactggttag cctggtatca actgaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgatcac cttcggcgga   300
gggaccaagg tggagatcaa acgtggtggt ggtggtagcg gcggcggcgg ctctggtggt   360
ggtggatccc aggtccagct ggtacagtct ggggctgagg tgaagaagcc tgggacctca   420
gtgaaggtct cctgcaaggc ttctggatac accttcacct cctactatat acactgggtg   480
cgacaggccc ctggacaagg gcttgagtgg atgggatgga tcaaccctaa cactggtggc   540
tcaaactttg cacagaagtt tcagggcagg gtcaccatga ccaggacac gtccatcagc    600 acagcctaca tggagctgaa caggctgagg tctgacgaca cggccgtgta ttactgtgcg   660
cgcggtgacg ttacttacga tgaatggggt caaggtactc tggtgaccgt ctcctcacac   720
catcaccatc accatggcgc atacccgtac gacgttccgg actacgcttc ttag         774

<210> SEQ ID NO 127
<211> LENGTH: 10
<212> TYPE: PRT
<213> ORGANISM: Homo sapiens

<400> SEQUENCE: 127

Gln Val Trp Asp Ile Asn Asp His Tyr Val
1               5                   10

<210> SEQ ID NO 128
<211> LENGTH: 10
<212> TYPE: PRT
<213> ORGANISM: Homo sapiens

<400> SEQUENCE: 128

Ala Arg Ser Gln Ala Ser Phe Met Asp Ile
1               5                   10

<210> SEQ ID NO 129
<211> LENGTH: 108
<212> TYPE: PRT
<213> ORGANISM: Homo sapiens

<400> SEQUENCE: 129

Ser Tyr Glu Leu Thr Gln Pro Pro Ser Val Ser Val Ala Pro Gly Lys
1               5                   10                  15

Thr Ala Ser Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Asp Met Arg Pro Ser Gly Ile Pro Glu Arg Phe Ser Gly Ser
        50                  55                  60

Ser Ser Gly Asn Thr Ala Thr Leu Thr Ile Ser Pro Val Glu Ala Gly
65                  70                  75                  80

Asp Glu Ala Asp Tyr Tyr Cys Gln Val Trp Asp Ile Asn Asp His Tyr
                85                  90                  95
```

Val Phe Ala Ser Gly Thr Lys Val Thr Val Leu Gly
            100                 105

<210> SEQ ID NO 130
<211> LENGTH: 324
<212> TYPE: DNA
<213> ORGANISM: Homo sapiens

<400> SEQUENCE: 130
tcctatgagc tgactcagcc accctcagtg tcagtggccc caggaaagac ggccagcatt      60
acctgtgggg gaaacaacat tggaagtaaa agtgtgcact ggtaccagca gaagccaggc     120
caggcccctg tgctggtcat ctattatgat gacatgcggc cctcaggtat ccctgagcga     180
ttctctggct ccagctctgg gaacacggcc accctgacca tcagcccggt cgaagccggg     240
gatgaggccg actattactg tcaggtgtgg gatattaatg atcattatgt cttcgcatcg     300
gggaccaagg tcaccgtcct aggt                                            324

<210> SEQ ID NO 131
<211> LENGTH: 117
<212> TYPE: PRT
<213> ORGANISM: Homo sapiens

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gln Ala Ser Phe Met Asp Ile Trp Gly Gln Gly Thr Leu
            100                 105                 110

Val Thr Val Ser Ser
        115

<210> SEQ ID NO 132
<211> LENGTH: 351
<212> TYPE: DNA
<213> ORGANISM: Homo sapiens

<400> SEQUENCE: 132
gaggtgcagc tggtggagtc tgggggaggc ttggtacagc ctggggggtc cctgagactc      60
tcctgtgcag cctctggatt caccttagc agctatgcca tgagctgggt ccgccaggct     120
ccagggaagg gctggagtg gtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gcgctctcag     300
gcttctttca tggatatctg gggtcaaggt actctggtga ccgtctcctc a               351

<210> SEQ ID NO 133
<211> LENGTH: 258

<212> TYPE: PRT
<213> ORGANISM: Homo sapiens

<400> SEQUENCE: 133

```
Ser Tyr Glu Leu Thr Gln Pro Pro Ser Val Ser Val Ala Pro Gly Lys
1               5                   10                  15

Thr Ala Ser Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Asp Met Arg Pro Ser Gly Ile Pro Glu Arg Phe Ser Gly Ser
    50                  55                  60

Ser Ser Gly Asn Thr Ala Thr Leu Thr Ile Ser Pro Val Glu Ala Gly
65                  70                  75                  80

Asp Glu Ala Asp Tyr Tyr Cys Gln Val Trp Asp Ile Asn Asp His Tyr
                85                  90                  95

Val Phe Ala Ser Gly Thr Lys Val Thr Val Leu Gly Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Phe Ser Ser Tyr Ala Met Ser Trp Val
145                 150                 155                 160

Arg Gln Ala Pro Gly Lys Gly Leu Glu Trp Val Ser Ala Ile Ser Gly
                165                 170                 175

Ser Gly Gly Ser Thr Tyr Tyr Ala Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Arg Ala Glu Asp Thr Ala Val Tyr Tyr Cys Ala Arg Ser Gln Ala
    210                 215                 220

Ser Phe Met Asp Ile Trp Gly Gln Gly Thr Leu Val Thr Val Ser Ser
225                 230                 235                 240

His His His His His Gly Ala Tyr Pro Tyr Asp Val Pro Asp Tyr
                245                 250                 255

Ala Ser
```

<210> SEQ ID NO 134
<211> LENGTH: 777
<212> TYPE: DNA
<213> ORGANISM: Homo sapiens

<400> SEQUENCE: 134

```
tcctatgagc tgactcagcc accctcagtg tcagtggccc caggaaagac ggccagcatt    60
acctgtgggg gaaacaacat tggaagtaaa agtgtgcact ggtaccagca gaagccaggc   120
caggcccctg tgctggtcat ctattatgat gacatgcggc cctcaggtat ccctgagcga   180
ttctctggct ccagctctgg gaacacggcc accctgacca tcagcccggt cgaagccggg   240
gatgaggccg actattactg tcaggtgtgg gatattaatg atcattatgt cttcgcatcg   300
gggaccaagg tcaccgtcct aggtggtggt ggtggtagcg gcggcggcgg ctctggtggt   360
ggtggatccg aggtgcagct ggtggagtct gggggaggct tggtacagcc tggggggtcc   420
ctgagactct cctgtgcagc ctctggattc acctttagca gctatgccat gagctgggtc   480
```

```
cgccaggctc cagggaaggg gctggagtgg gtctcagcta ttagtggtag tggtggtagc    540
acatactacg cagactccgt gaagggccgg ttcaccatct ccagagacaa ttccaagaac    600
acgctgtatc tgcaaatgaa cagcctgaga gccgaggaca cggccgtata ttactgtgcg    660
cgctctcagg cttctttcat ggatatctgg ggtcaaggta ctctggtgac cgtctcctca    720
caccatcacc atcaccatgg cgcatacccg tacgacgttc cggactacgc ttcttag      777
```

<210> SEQ ID NO 135
<211> LENGTH: 11
<212> TYPE: PRT
<213> ORGANISM: Homo sapiens

<400> SEQUENCE: 135

Gln Val Trp Asp Ser Ser Ser Asp Gln Gly Val
1               5                   10

<210> SEQ ID NO 136
<211> LENGTH: 7
<212> TYPE: PRT
<213> ORGANISM: Homo sapiens

<400> SEQUENCE: 136

Ile Gly Thr Gly Gly Gly Thr
1               5

<210> SEQ ID NO 137
<211> LENGTH: 10
<212> TYPE: PRT
<213> ORGANISM: Homo sapiens

<400> SEQUENCE: 137

Ala Arg Gly Thr Gly Tyr Asp Gly Asp Gln
1               5                   10

<210> SEQ ID NO 138
<211> LENGTH: 109
<212> TYPE: PRT
<213> ORGANISM: Homo sapiens

<400> SEQUENCE: 138

Leu Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Gln
                85                  90                  95

Gly Val Phe Gly Thr Gly Thr Lys Val Thr Val Leu Gly
            100                 105

<210> SEQ ID NO 139
<211> LENGTH: 327
<212> TYPE: DNA
<213> ORGANISM: Homo sapiens

<400> SEQUENCE: 139

```
ctgcctgtgc tgactcagcc accctcggtg tcagtggccc caggacagac ggccaggatc    60
acctgtgggg gaaacaacat tggaagtaaa agtgtgcact ggtaccagca gaagccaggc   120
caggcccctg tgctggtcgt ctatgatgat agcgaccggc cctcagggat ccctgagcga   180
ttctctggct ccaattctgg gaacacggcc accctgacca tcagcagggt cgaagccggg   240
gatgaggccg actattactg tcaggtgtgg gatagtagta gtgatcaggg cgtcttcgga   300
actgggacca aggtcaccgt cctaggt                                      327
```

<210> SEQ ID NO 140
<211> LENGTH: 116
<212> TYPE: PRT
<213> ORGANISM: Homo sapiens

<400> SEQUENCE: 140

Glu Val Gln Leu Val Gln Ser Gly Gly Gly Leu Val Gln Pro Arg Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Met Tyr Tyr Cys Ala
                85                  90                  95

Arg Gly Thr Gly Tyr Asp Gly Asp Gln Trp Gly Gln Gly Thr Leu Val
                100                 105                 110

Thr Val Ser Ser
        115

<210> SEQ ID NO 141
<211> LENGTH: 348
<212> TYPE: DNA
<213> ORGANISM: Homo sapiens

<400> SEQUENCE: 141

```
gaagtgcagc tggtgcagtc tggggaggc ttggtacagc ctaggggtc cctgagactc    60 tcctgtgcag gctctggatt caccttcagt agctatgcta tgcactgggt tcgccaggct   120
ccaggaaaag gtctggagtg gtatcagct attggtactg gtggtggcac atactatgca   180
gactccgtga agggccgatt caccatctcc agggacaatg ccaagaactc cttgtatctt   240
caaatgaaca gcctgagagc cgaggacacc gccatgtatt actgtgcgcg cggtactggt   300
tacgacggtg atcagtgggg tcaaggtact ctggtgaccg tctcctca              348
```

<210> SEQ ID NO 142
<211> LENGTH: 258
<212> TYPE: PRT
<213> ORGANISM: Homo sapiens

<400> SEQUENCE: 142

Leu Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
             35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp Gln
                 85                  90                  95

Gly Val Phe Gly Thr Gly Thr Lys Val Thr Val Leu Gly Gly Gly
                100                 105                 110

Gly Ser Gly Gly Gly Ser Gly Gly Gly Ser Glu Val Gln Leu
             115                 120                 125

Val Gln Ser Gly Gly Gly Leu Val Gln Pro Gly Ser Leu Arg Leu
         130                 135                 140

Ser Cys Ala Gly Ser Gly Phe Thr Phe Ser Ser Tyr Ala Met His Trp
145                 150                 155                 160

Val Arg Gln Ala Pro Gly Lys Gly Leu Glu Trp Val Ser Ala Ile Gly
                165                 170                 175

Thr Gly Gly Gly Thr Tyr Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Met Tyr Tyr Cys Ala Arg Gly Thr Gly
    210                 215                 220

Tyr Asp Gly Asp Gln Trp Gly Gln Gly Thr Leu Val Thr Val Ser Ser
225                 230                 235                 240

His His His His His His Gly Ala Tyr Pro Tyr Asp Val Pro Asp Tyr
                245                 250                 255

Ala Ser

<210> SEQ ID NO 143
<211> LENGTH: 777
<212> TYPE: DNA
<213> ORGANISM: Homo sapiens

<400> SEQUENCE: 143
ctgcctgtgc tgactcagcc accctcggtg tcagtggccc caggacagac ggccaggatc      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaattctgg gaacacggcc accctgacca tcagcagggt cgaagcgggg     240
gatgaggccg actattactg tcaggtgtgg gatagtagta gtgatcaggg cgtcttcgga     300
actgggacca aggtcaccgt cctaggtggt ggtggtggta gcggcggcgg cggctctggt     360
ggtggtggat ccgaagtgca gctggtgcag tctgggggag gcttggtaca gcctaggggg     420
tccctgagac tctcctgtgc aggctctgga ttcaccttca gtagctatgc tatgcactgg     480
gttcgccagg ctccaggaaa aggtctggag tgggtatcag ctattggtac tggtggtggc     540
acatactatg cagactccgt gaagggccga ttcaccatct ccaggacaa tgccaagaac     600 tccttgtatc ttcaaatgaa cagcctgaga gccgaggaca ccgccatgta ttactgtgcg     660
cgcggtactg gttacgacgg tgatcagtgg ggtcaaggta ctctggtgac cgtctcctca     720
caccatcacc atcaccatgg cgcatacccg tacgacgttc cggactacgc ttcttag       777

UNITED STATES PATENT AND TRADEMARK OFFICE
CERTIFICATE OF CORRECTION

PATENT NO. : 11,136,392 B2  
APPLICATION NO. : 15/849107  
DATED : October 5, 2021  
INVENTOR(S) : Brentjens et al.

Page 1 of 1

It is certified that error appears in the above-identified patent and that said Letters Patent is hereby corrected as shown below:

In the Claims

Column 131, Line 52: Claim 16, Delete "of claim 14." and insert -- of claim 1. --

Column 131, Line 56: Claim 17, Delete "of claim 14" and insert -- of claim 1 --

Column 131, Line 64: Claim 19, Delete "of claim 14" and insert -- of claim 1 --

Column 132, Line 3: Claim 21, Delete "of claim 14" and insert -- of claim 1 --

Column 132, Line 8: Claim 22, Delete "of claim 14" and insert -- of claim 1 --

Column 132, Line 13: Claim 23, Delete "of claim 14" and insert -- of claim 1 --

Column 132, Line 51: Claim 34, Delete "of claim 14" and insert -- of claim 1 --

Column 132, Line 57: Claim 36, Delete "of claim 14" and insert -- of claim 1 --

Signed and Sealed this  
Eighth Day of February, 2022

Drew Hirshfeld  
*Performing the Functions and Duties of the*  
*Under Secretary of Commerce for Intellectual Property and*  
*Director of the United States Patent and Trademark Office*